(12) United States Patent
Shelton, IV et al.

(10) Patent No.: US 12,426,879 B2
(45) Date of Patent: Sep. 30, 2025

(54) SURGICAL SYSTEM COMPRISING CONTROL CIRCUIT TO SET VELOCITY OF CLOSURE DRIVER BASED ON SENSOR DATA

(71) Applicant: Cilag GmbH International, Zug (CH)

(72) Inventors: Frederick E. Shelton, IV, Hillsboro, OH (US); Jason L. Harris, Lebanon, OH (US); David C. Yates, Morrow, OH (US); Gregory J. Bakos, Mason, OH (US); Sarah A. Worthington, Cincinnati, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/543,853

(22) Filed: Dec. 18, 2023

(65) Prior Publication Data

US 2024/0156454 A1    May 16, 2024

Related U.S. Application Data

(63) Continuation of application No. 17/181,740, filed on Feb. 22, 2021, now Pat. No. 11,890,005, which is a
(Continued)

(51) Int. Cl.
*A61B 17/068* (2006.01)
*A61B 17/072* (2006.01)
(Continued)

(52) U.S. Cl.
CPC ........ *A61B 17/068* (2013.01); *A61B 17/0682* (2013.01); *A61B 17/07207* (2013.01); *A61B 17/07292* (2013.01); *A61B 34/30* (2016.02); *A61B 2017/00017* (2013.01); *A61B 2017/00022* (2013.01); *A61B 2017/00026* (2013.01); *A61B 2017/00084* (2013.01); *A61B 2017/00309* (2013.01); *A61B 2017/00477* (2013.01); *A61B 2017/07257* (2013.01); *A61B 2017/07271* (2013.01); *A61B 2017/07285* (2013.01); *A61B 2017/2927* (2013.01); *A61B 2090/064* (2016.02)

(58) Field of Classification Search
CPC .............. A61B 17/068; A61B 17/0682; A61B 17/07207; A61B 17/07292; A61B 2017/07257; A61B 2017/07271; A61B 2017/07285; A61B 2017/2927
See application file for complete search history.

(56) References Cited

U.S. PATENT DOCUMENTS 6,132,368 A    10/2000    Cooper
7,524,320 B2   4/2009     Tierney et al.
(Continued)

*Primary Examiner* — Michelle Lopez

(57) ABSTRACT

A surgical system comprising an end effector, a closure driver, a force sensor, and a control circuit is disclosed. The end effector comprises a first jaw and a second jaw rotatable relative to the first jaw between an open position and a closed position. The closure driver is configured to apply a closure force to the second jaw to rotate the second jaw toward the closed position. The force sensor is to measure a parameter indicative of the closure force. The control circuit is to receive an output of the force sensor indicative of the parameter and set a velocity of the closure driver based on the received output and a force threshold.

20 Claims, 46 Drawing Sheets

Related U.S. Application Data continuation of application No. 15/636,829, filed on Jun. 29, 2017, now Pat. No. 10,932,772.

(51) Int. Cl.
*A61B 34/30* (2016.01)
*A61B 17/00* (2006.01)
*A61B 17/29* (2006.01)
*A61B 90/00* (2016.01)

(56) References Cited

U.S. PATENT DOCUMENTS

| | | |
|---|---|---|
| 8,855,822 B2 | 10/2014 | Bartol et al. |
| 8,955,732 B2 | 2/2015 | Zemlok et al. |
| 9,113,880 B2 | 8/2015 | Zemlok et al. |
| 9,808,246 B2 | 11/2017 | Shelton, IV et al. |
| 9,839,428 B2 | 12/2017 | Baxter, III et al. |
| 9,913,642 B2 | 3/2018 | Leimbach et al. |
| 10,111,679 B2 | 10/2018 | Baber et al. |
| 10,258,418 B2 | 4/2019 | Shelton, IV et al. |
| 10,398,434 B2 | 9/2019 | Shelton, IV et al. |
| 10,524,787 B2 | 1/2020 | Shelton, IV et al. |
| 10,687,806 B2 | 6/2020 | Shelton, IV et al. |
| 10,898,183 B2 | 1/2021 | Shelton, IV et al. |
| 10,932,772 B2 | 3/2021 | Shelton, IV et al. |
| 11,007,022 B2 | 5/2021 | Shelton, IV et al. |
| 11,890,005 B2 | 2/2024 | Shelton, IV et al. |
| 2007/0175949 A1* | 8/2007 | Shelton ............... A61B 17/285 227/176.1 |
| 2014/0001231 A1 | 1/2014 | Shelton, IV et al. |
| 2019/0201018 A1* | 7/2019 | Shelton, IV ........... G16H 40/20 |
| 2019/0201019 A1* | 7/2019 | Shelton, IV ........... A61B 34/25 |

\* cited by examiner

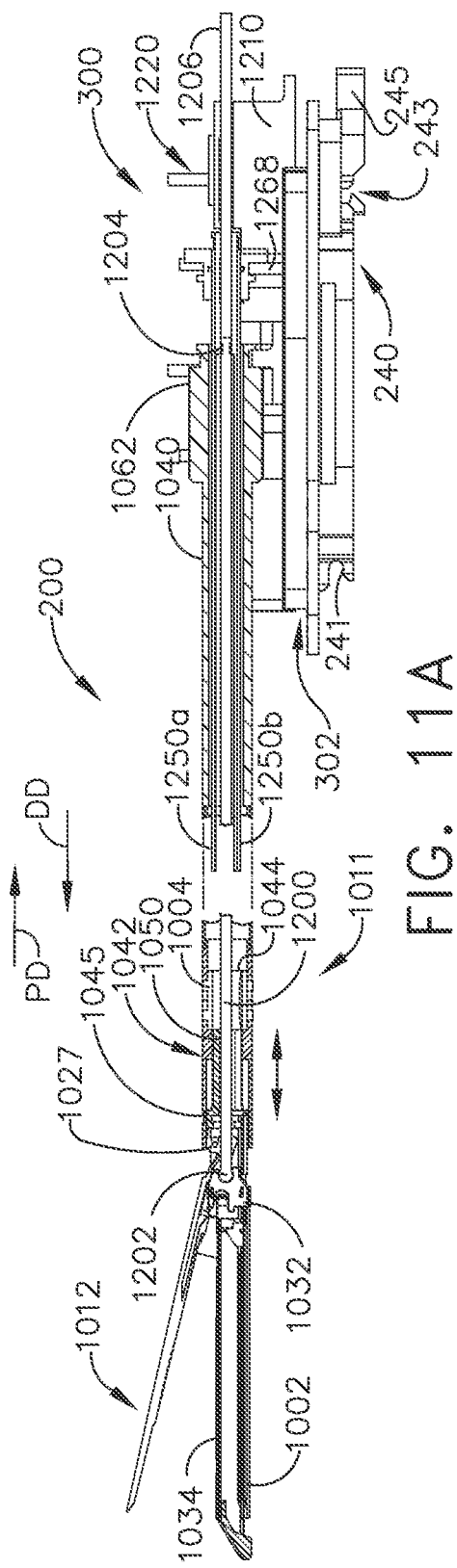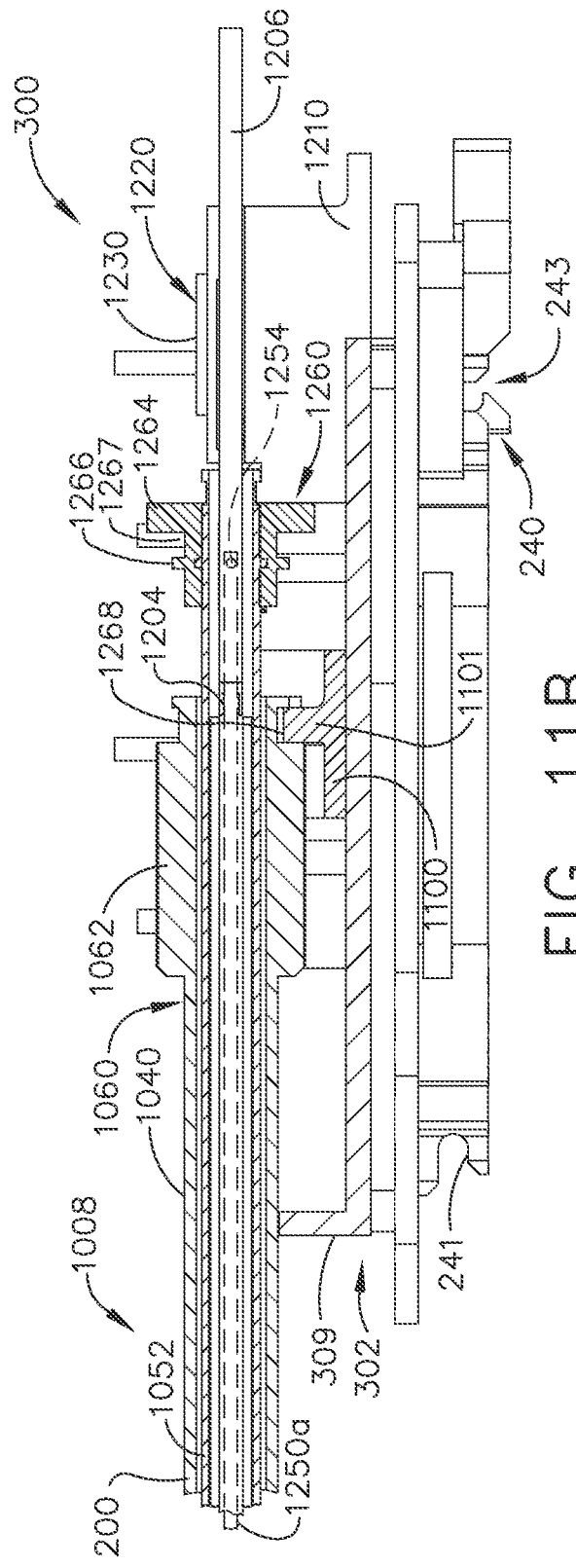
FIG. 11A
FIG. 11B

| FIRING | FROM CLOSURE | | FROM FIRING | |
|---|---|---|---|---|
| | INITIAL VELOCITY SELECTION | | FIRING VELOCITY UPDATES | |
| VARIABLE | SLOW | FAST | DECREASE | INCREASE |
| GAP | ++ | — | + | — |
| F2F/C | ++ | — | ++ | — |
| KNIFE VELOCITY | / | / | — | + |
| IMPEDANCE | ++ | — | + | + |
| CARTRIDGE COVERAGE | + | — | + | + |

FIG. 31

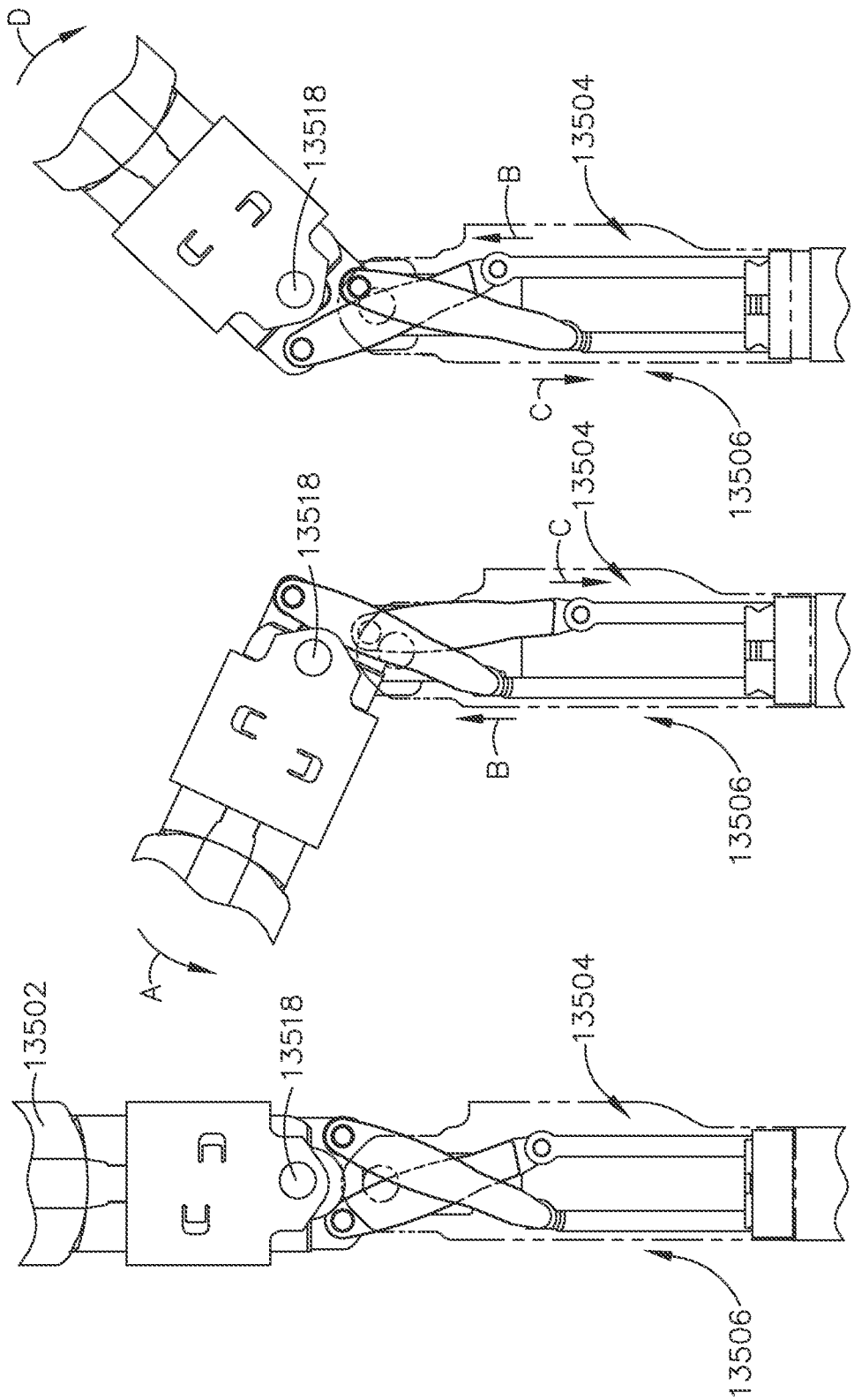

SURGICAL SYSTEM COMPRISING CONTROL CIRCUIT TO SET VELOCITY OF CLOSURE DRIVER BASED ON SENSOR DATA

CROSS-REFERENCE TO RELATED APPLICATIONS

This application is a continuation patent application claiming priority under 35 U.S.C. § 120 to U.S. patent application Ser. No. 17/181,740, titled METHODS FOR CLOSED LOOP VELOCITY CONTROL FOR ROBOTIC SURGICAL INSTRUMENT, filed Feb. 22, 2021, now U.S. Patent Application Publication No. 2021/0244407, which is a continuation patent application claiming priority under 35 U.S.C. § 120 to U.S. patent application Ser. No. 15/636,829, titled METHODS FOR CLOSED LOOP VELOCITY CONTROL FOR ROBOTIC SURGICAL INSTRUMENT, filed Jun. 29, 2017, which issued on Mar. 2, 2021 as U.S. Pat. No. 10,932,772, the entire disclosures of which are hereby incorporated by reference herein.

TECHNICAL FIELD

The present disclosure relates to robotic surgical instruments and, in various circumstances, to robotic surgical stapling and cutting instruments and staple cartridges therefor that are designed to staple and cut tissue.

BACKGROUND

In a motorized robotic surgical stapling and cutting instrument it may be useful to measure the position and velocity of a cutting member in an initial predetermined time or displacement to control speed. Measurement of position or velocity over an initial predetermined time or displacement may be useful to evaluate tissue thickness and to adjust the speed of the remaining stroke based on this comparison against a threshold.

In a motorized robotic surgical stapling and cutting instrument it may be useful to measure the position and velocity of a cutting member in an initial predetermined time or displacement to control speed. Measurement of position or velocity over an initial predetermined time or displacement may be useful to evaluate tissue thickness and to adjust the speed of the remaining stroke based on this comparison against a threshold.

In a motorized robotic surgical stapling and cutting instrument it may be useful to measure the position and velocity of a cutting member in an initial predetermined time or displacement to control speed. Measurement of position or velocity over an initial predetermined time or displacement may be useful to evaluate tissue thickness and to adjust the speed of the remaining stroke based on this comparison against a threshold.

Robotic surgical tools may be useful in providing stable and reliable application for surgical procedures. Various components may be interchangeable such that a single support apparatus may be used to attach to different modular robotic surgical arms. Some of these robotic systems employ multiple motors to control individual components that may move independently but still involve a degree of interrelationship.

SUMMARY

In one aspect, a method of controlling velocity of a firing member in a robotic surgical system is provided. The method comprises detecting, by a control circuit, a condition at an end effector during a closure phase; setting, by the control circuit, command velocity of a motor coupled to a displacement member coupled to the end effector based on the detected condition at the end effector during the closure phase; firing, by the control circuit, the displacement member at the set command velocity; detecting, by the control circuit, a condition at the end effector during a firing phase; and setting, by the control circuit, command velocity of the motor based on the condition detected at the end effector during the firing phase.

In another aspect, a method of controlling velocity of a firing member in a robotic surgical system comprises receiving, by a control circuit, actual closure force of a closure member from a force sensor coupled to the closure member and the control circuit; comparing, by the control circuit, the actual closure force to a threshold closure force; determining, by the control circuit, a set point velocity to displace the closure member based on the comparison; and controlling, by the control circuit, the actual velocity of the closure member based on the set point velocity.

In another aspect a method of controlling velocity of a firing member in a robotic surgical system comprises receiving, by a control circuit, actual closure force of a closure member from a force sensor coupled to the closure member and the control circuit; receiving, by the control circuit, actual position of a firing member from a position sensor coupled to the firing member and the control circuit; and setting, by the control circuit, a new closure force based on the actual closure force applied to the closure member and the actual position of the firing member.

In another aspect, a robotic surgical system is provided. The robotic surgical system comprises a control circuit configured to: detect a condition at an end effector during a closure phase; set command velocity of a motor coupled to a displacement member coupled to the end effector based on the detected condition at the end effector during the closure phase; fire the displacement member at the set command velocity; detect a condition at the end effector during a firing phase; and set command velocity of the motor based on the condition detected at the end effector during the firing phase.

In another aspect, the robotic surgical system comprises a control circuit coupled to a motor and configured to set a command velocity of the motor during a closure phase or a firing phase, wherein the motor is configured to drive a displacement member at the command velocity, wherein the control circuit is configured to: detect a first condition at the end effector; detect a second condition at the end effector; set the command velocity of the motor based on the detected first and second conditions at the end effector; and fire the displacement member at the set command velocity.

In another aspect, the robotic surgical system comprises a first motor to drive a displacement member coupled to a cutting member; a second motor to drive a closure tube coupled to an anvil portion of an end effector, wherein the closure tube is configured to close or open the anvil; and a control circuit coupled to the first and second motor, wherein control circuit is configured to set a command velocity of the first motor during a closure phase or a firing phase and set a command velocity of the second motor to apply a closure force to the closure tube coupled to the anvil, wherein the control circuit is configured to: detect a first condition at the end effector; detect a second condition at the end effector; set the first command velocity of the motor based on the detected first and second conditions at the end effector; and fire the displacement member at the first set command velocity.

In another aspect, a control system for a robotic surgical system is provided. The control system comprises a control circuit configured to: determine actual closure force of a closure member; compare the actual closure force to a threshold closure force; determine a set point velocity to displace the closure member based on the comparison; and control the actual velocity of the closure member based on the set point velocity.

In another aspect, the control system comprises a first motor configured to couple to a closure member; a force sensor configured to measure closure force applied to the closure member; a closed loop feedback control system comprising a control circuit coupled to the first motor and the force sensor, wherein the control circuit is configured to: receive, from the force sensor, actual closure force the closure member; compare the actual closure force to a threshold closure force; determine a set point velocity of the first motor to displace the closure member based on the comparison; and control the actual velocity of the closure member based on the set point velocity.

In another aspect, the control system comprises a proportional, integral, and derivative (PID) feedback control system, the control circuit configured to: determine actual closure force of a closure member; compare the actual closure force to a threshold closure force; determine a set point velocity to displace the closure member based on the comparison; and control the actual velocity of the closure member based on the set point velocity; a force sensor coupled to the control circuit, the force sensor configured measure the closure force; and a motor coupled to the control circuit and to the closure member, wherein the control circuit is configured to advance the closure member during at least a portion of a firing stroke; wherein the threshold closure force comprises an upper threshold and a lower threshold, wherein the set point velocity is configured to advance the closure member distally when the actual closure force is less than the lower threshold, and wherein the set point velocity is configured to retract the closure member proximally when the actual closure force is greater than the lower threshold.

In another aspect, a control system for a robotic surgical system is provided. The control system for a robotic surgical system, the control system comprising: a control circuit configured to: determine a closure force applied to a closure member; determine a position of a firing member; and set a new closure force based on the closure force applied to the closure member and the position of the firing member.

In another aspect, the control system for a robotic surgical system comprises a first motor configured to couple to a closure member; a force sensor configured to measure closure force applied to the closure member; a control circuit coupled to the first motor and the force sensor, wherein the control circuit is configured to: receive, from the force sensor, actual closure force applied to the closure member; receive, from the position sensor, a position of a firing member; and set a new closure force based on the actual closure force applied to the closure member and the position of the firing member.

In another aspect, the control system for a robotic surgical system comprises a control circuit configured to: apply a closure force to a closure member during a closure period; increase the closure force during a waiting period following the closure period; determine a closure force applied to the closure member; determine a position of a firing member during a firing stroke; and set a new closure force of the closure member based on the closure force and the position of the firing member.

In another aspect, a system for a robotic surgical instrument is presented. The system may include: a control circuit; a first motor and a second motor, both communicatively coupled to the control circuit; a first articulation arm communicatively coupled to the first motor; a second articulation arm communicatively coupled to the second motor; an end effector coupled to the first articulation arm via a first hinge and the second articulation arm via a second hinge. The control circuit may be configured to cause the first motor to apply a first force to the first articulation arm. The control circuit may be configured to cause the second motor to apply a second force to the second articulation arm, wherein the second force is antagonistic to the first force such that the first and second forces apply counteracting forces at the end effector. The first and second forces may cause the end effector to articulate via the first and second hinges.

In another aspect, the end effector is configured to articulate to a prescribed angle based on a ratio of magnitudes between the first force and the second force. In some aspects, the system further includes an articulation pivot coupled to the end effector, wherein the end effector is further configured to articulate about the articulation pivot. In some aspects, the articulation pivot is positioned off of a center axis running longitudinally in between and equidistant from at least a portion of the first and second articulation arms.

In another aspect, a method of a robotic surgical instrument comprising a control circuit, a first motor, a second motor, a first articulation arm, a second articulation arm, and an end effector is presented. The method may include: instructing, by the control circuit, the first motor to apply a first force to the first articulation arm; instructing, by the control circuit, the second motor to apply a second force to the second articulation arm, wherein the second force is antagonistic to the first force such that the first and second forces apply counteracting forces at the end effector; and causing the end effector to articulate via first and second hinges based on the first and second forces applied to the first and second articulation arms, respectively.

FIGURES

The novel features of the aspects described herein are set forth with particularity in the appended claims. These aspects, however, both as to organization and methods of operation may be better understood by reference to the following description, taken in conjunction with the accompanying drawings.

FIG. 11A is a partial cross-sectional side view of the surgical tool of FIG. 6 according to one aspect of this disclosure.

FIG. 11B is an enlarged cross-sectional view of a portion of the surgical tool depicted in FIG. 11A according to one aspect of this disclosure.

FIG. 31 is a chart illustrating techniques for controlling the advancement or retraction velocity of a displacement member of a robotic surgical instrument according to one aspect of this disclosure.

FIG. 35A is a detail view of a section of the first graph shown in FIG. 35.

FIG. 45 shows the anvil in a neutral or straight position relative to the articulation arms.

FIG. 46 shows the left articulation arm moved up along a first direction, while simultaneously the right articulation arm is moved down along an opposite direction.

FIG. 47 shows reverse movements by the articulation arms that cause the anvil to move in the reverse, i.e., clockwise, direction.

DESCRIPTION

Applicant of the present application owns the following patent applications filed Jun. 29, 2017 and which are each herein incorporated by reference in their respective entireties:

U.S. patent application Ser. No. 15/636,837, titled CLOSED LOOP VELOCITY CONTROL TECHNIQUES BASED ON SENSED TISSUE PARAMETERS FOR ROBOTIC SURGICAL INSTRUMENT, by inventors Frederick E. Shelton, I V et al., filed Jun. 29, 2017, now U.S. Patent Application Publication No. 2019/0000565.

U.S. patent application Ser. No. 15/636,844, titled CLOSED LOOP VELOCITY CONTROL OF CLOSURE MEMBER FOR ROBOTIC SURGICAL INSTRUMENT, by inventors Frederick E. Shelton, I V et al., filed Jun. 29, 2017, now U.S. Pat. No. 10,398,434.

U.S. patent application Ser. No. 15/636,854, titled ROBOTIC SURGICAL INSTRUMENT WITH CLOSED LOOP FEEDBACK TECHNIQUES FOR ADVANCEMENT OF CLOSURE MEMBER DURING FIRING, by inventors Frederick E. Shelton, I V et al., filed Jun. 29, 2017, now U.S. Pat. No. 10,898,183.

U.S. patent application Ser. No. 15/636,858, titled SYSTEM FOR CONTROLLING ARTICULATION FORCES, by inventors Frederick E. Shelton, I V et al., filed Jun. 29, 2017, now U.S. Pat. No. 10,258,418.

Figure 1:
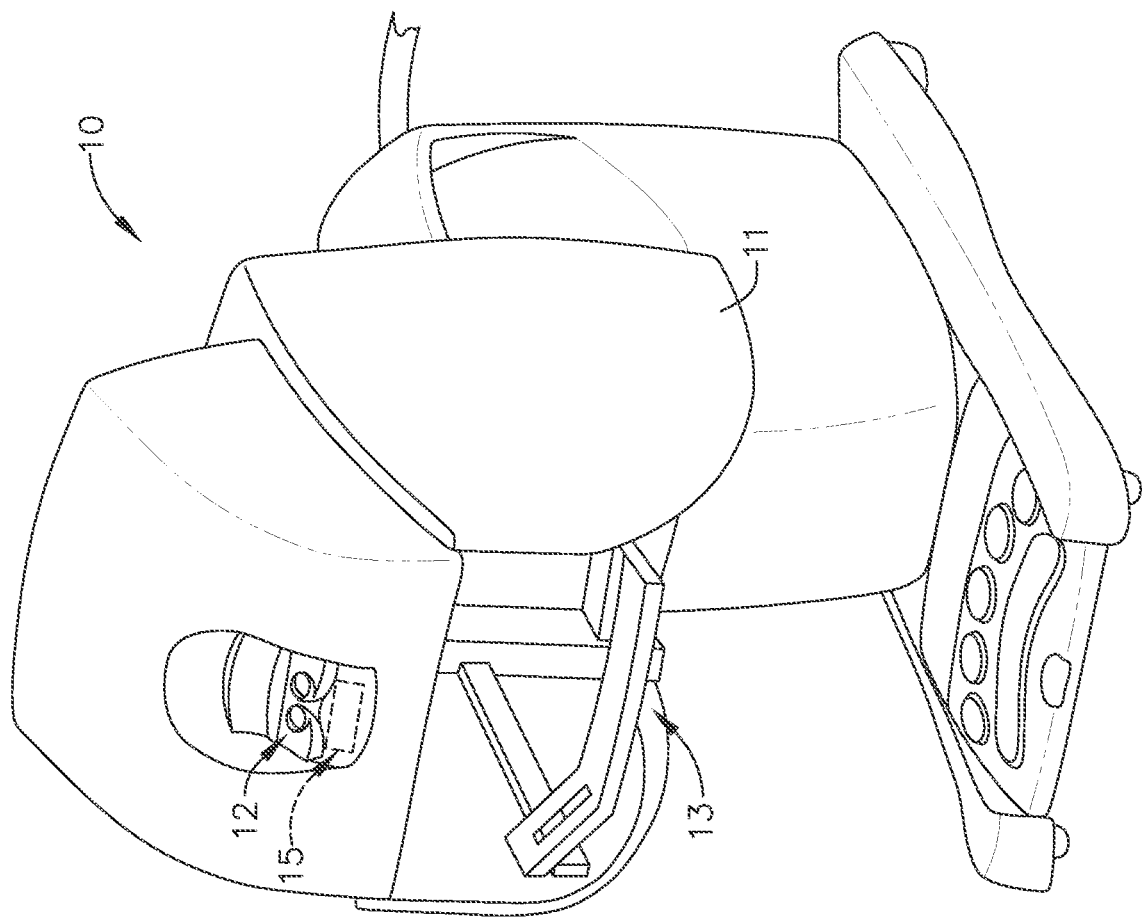
FIG. 1 is a perspective view of one robotic controller according to one aspect of this disclosure.
Figure 2:
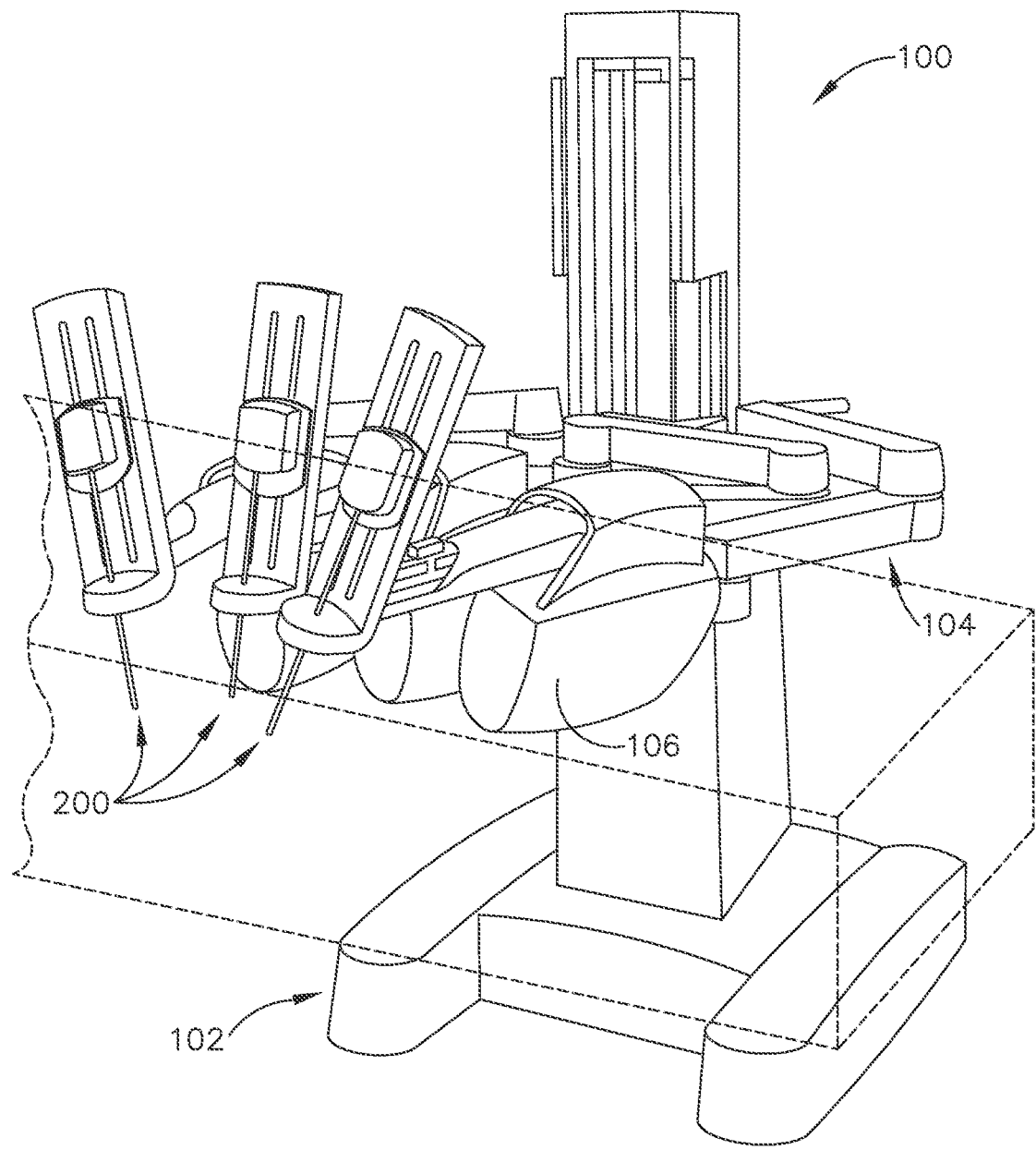
FIG. 2 is a perspective view of one robotic surgical arm cart/manipulator of a robotic surgical system operably supporting a plurality of surgical tool according to one aspect of this disclosure.

FIG. 1 depicts one aspect of a master robotic controller 11 that may be used in connection with a robotic arm slave cart 100 of the type depicted in FIG. 2. The master controller 11 and robotic arm slave cart 100, as well as their respective components and control systems are collectively referred to herein as a robotic surgical system 10. Examples of such systems and devices are disclosed in U.S. Pat. No. 7,524,320, which is incorporated herein by reference. The master controller 11 generally includes master controllers (generally represented as 13 in FIG. 1) which are grasped by the surgeon and manipulated in space while the surgeon views the procedure via a stereo display 12. The master controllers 11 generally comprise manual input devices which preferably move with multiple degrees of freedom, and which often further have an actuatable handle for actuating tools (for example, for closing grasping saws, applying an electrical potential to an electrode, or the like). Other arrangements may provide the surgeon with a feed back meter 15 that may be viewed through the display 12 and provide the surgeon with a visual indication of the amount of force being applied to the cutting instrument or dynamic clamping member. Additional examples are disclosed in U.S. Pat. No. 9,237,891, which is incorporated herein by reference.

As can be seen in FIG. 2, in one form, the robotic arm cart 100 is configured to actuate a plurality of surgical tools, generally designated as 200. Various robotic surgery systems and methods employing master controller and robotic arm cart arrangements are disclosed in U.S. Pat. No. 6,132,368, titled MULTI-COMPONENT TELEPRESENCE SYSTEM AND METHOD, the full disclosure of which is incorporated herein by reference. In various forms, the robotic arm cart 100 includes a base 102 from which, in the illustrated aspect, three surgical tools 200 are supported. In various forms, the surgical tools 200 are each supported by a series of manually articulatable linkages, generally referred to as set-up joints 104, and a robotic manipulator 106.

Figure 3:
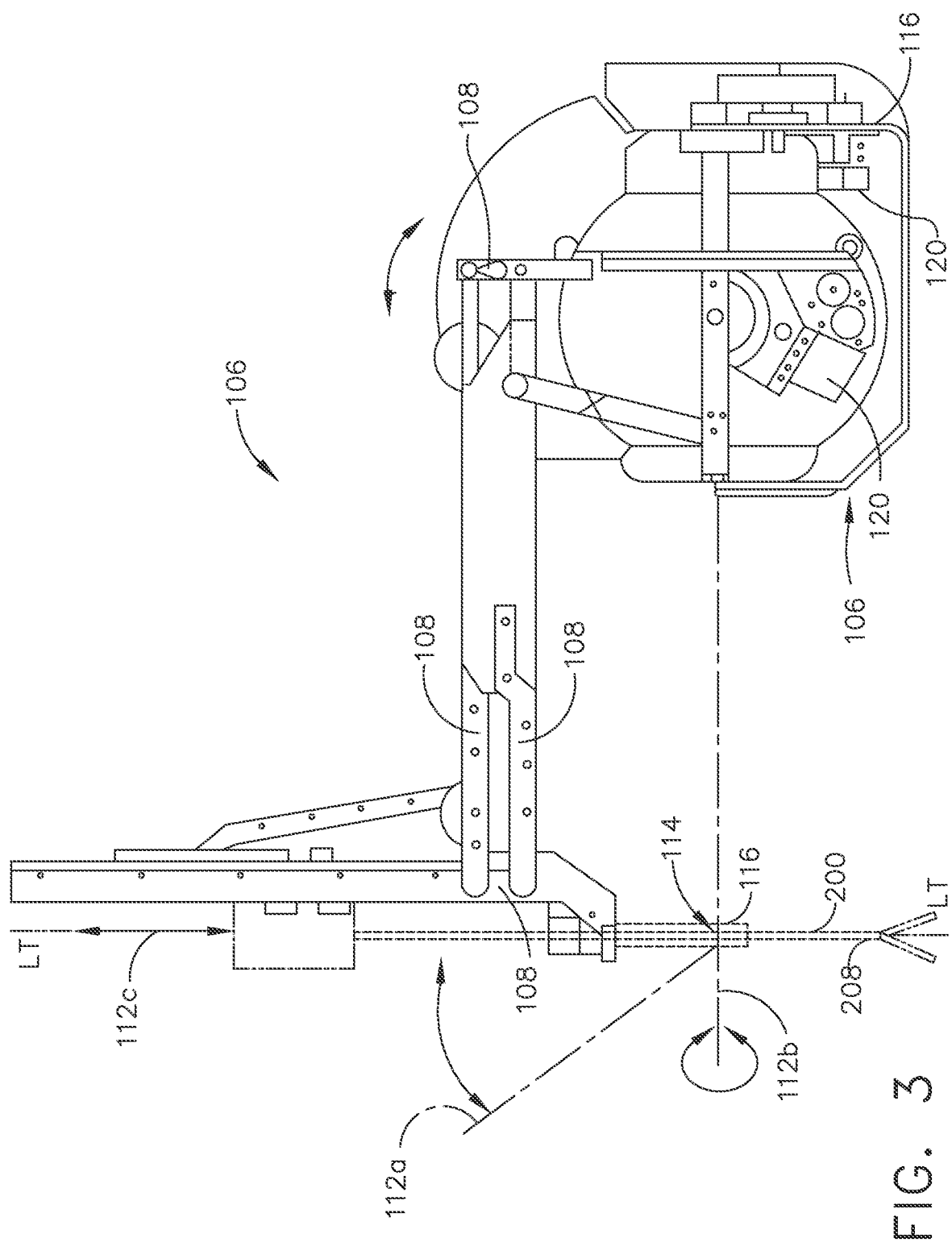
FIG. 3 is a side view of the robotic surgical arm cart/manipulator depicted in FIG. 2 according to one aspect of this disclosure.

Referring now to FIG. 3, in at least one form, robotic manipulators 106 may include a linkage 108 that constrains movement of the surgical tool 200. In various aspects, linkage 108 includes rigid links coupled together by rotational joints in a parallelogram arrangement so that the surgical tool 200 rotates around a point in space 110, as more fully described in issued U.S. Pat. No. 5,817,084, the full disclosure of which is herein incorporated by reference. The parallelogram arrangement constrains rotation to pivoting about an axis 112a, sometimes called the pitch axis. The links supporting the parallelogram linkage are pivotally mounted to set-up joints 104 (FIG. 2) so that the surgical tool 200 further rotates about an axis 112b, sometimes called the yaw axis. The pitch and yaw axes 112a, 112b intersect at the remote center 114, which is aligned along a shaft 208 of the surgical tool 200. The surgical tool 200 may have further degrees of driven freedom as supported by manipulator 106, including sliding motion of the surgical tool 200 along the longitudinal tool axis "LT-LT". As the surgical tool 200 slides along the tool axis LT-LT relative to manipulator 106 (arrow 112c), remote center 114 remains fixed relative to base 116 of manipulator 106. Hence, the entire manipulator is generally moved to re-position remote center 114. Linkage 108 of manipulator 106 is driven by a series of motors 120. These motors actively move linkage 108 in response to commands from a processor of a control system. As will be discussed in further detail below, motors 120 are also employed to manipulate the surgical tool 200.

Figure 4:
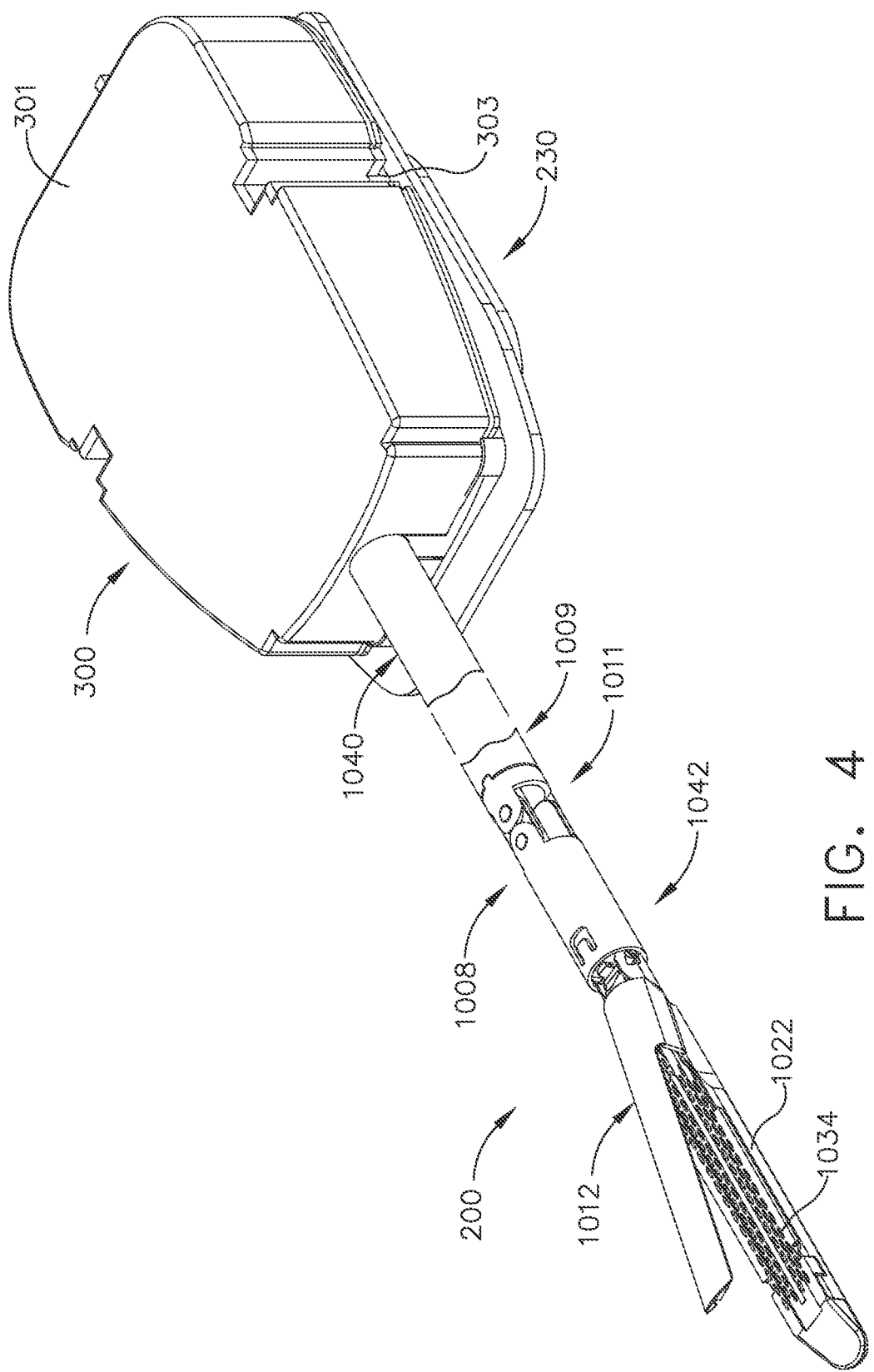
FIG. 4 is a perspective view of a surgical tool according to one aspect of this disclosure.
Figure 6:
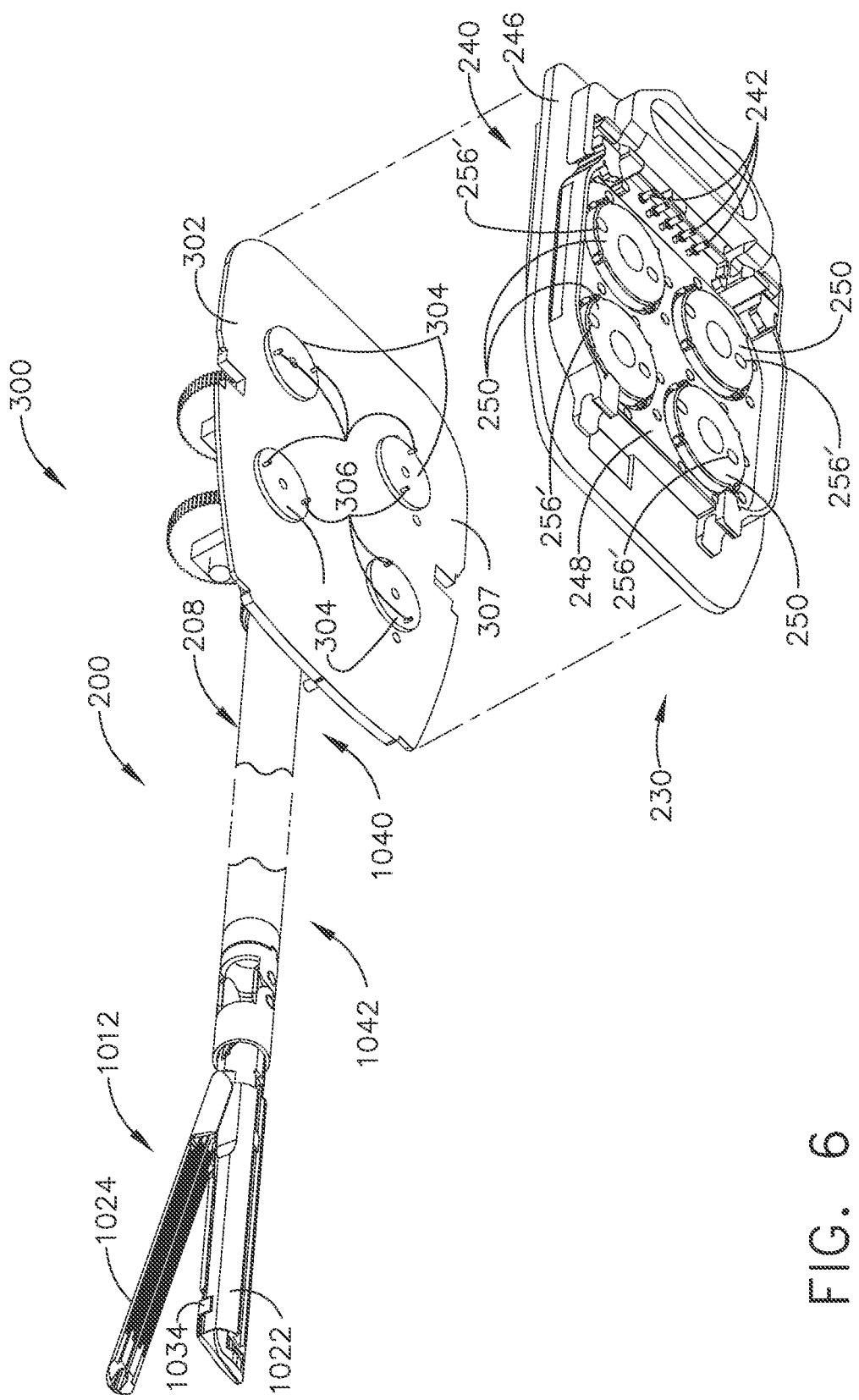
FIG. 6 is a partial bottom perspective view of the surgical tool aspect of FIG. 4 according to one aspect of this disclosure.
Figure 7:
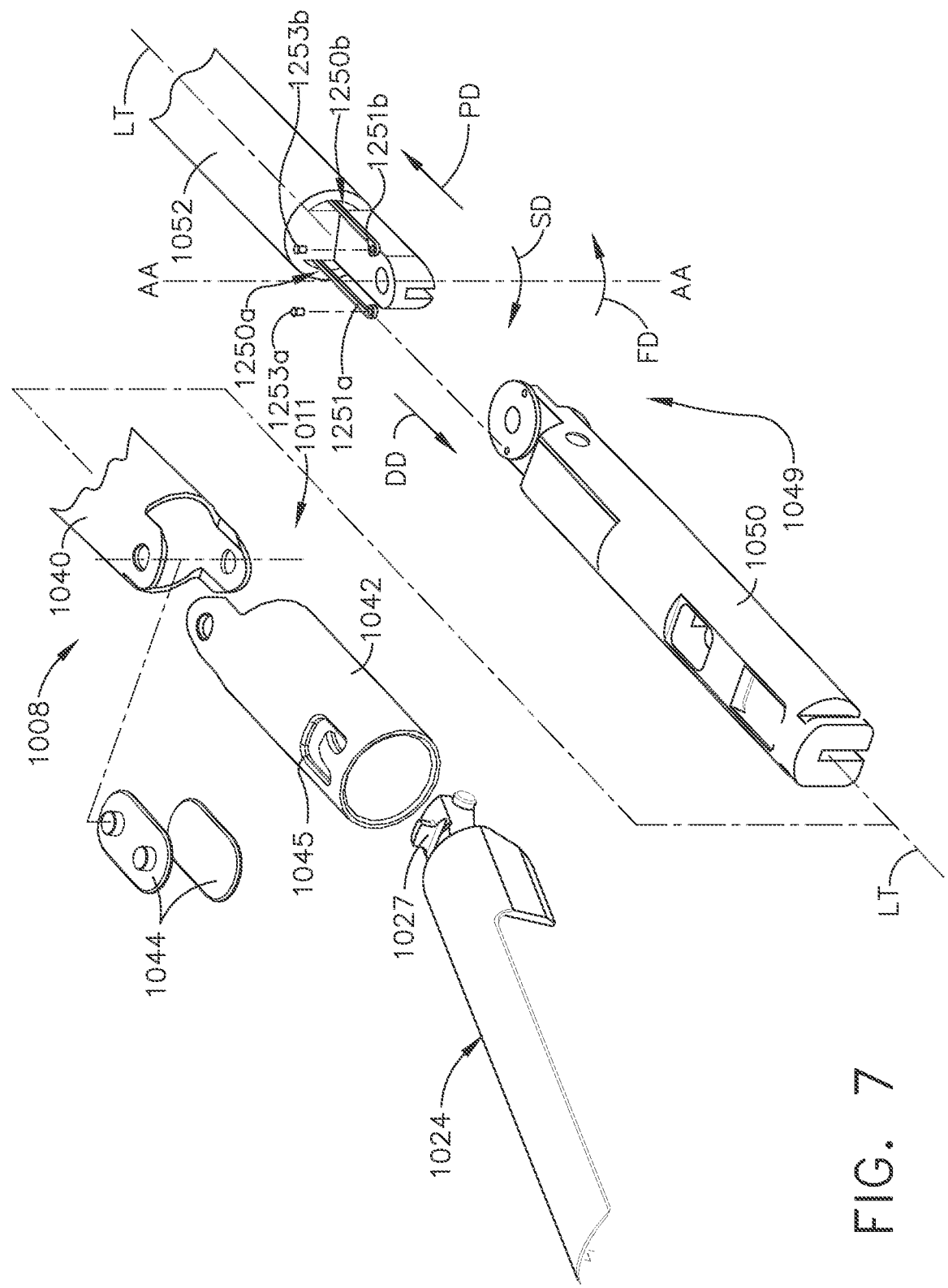
FIG. 7 is a partial exploded view of a portion of an articulatable surgical end effector according to one aspect of this disclosure.

FIG. 4 is a perspective view of a surgical tool 200 that is adapted for use with a robotic surgical system 10 that has a tool drive assembly that is operatively coupled to a master controller 11 that is operable by inputs from an operator (i.e., a surgeon) is depicted in FIG. 4. As can be seen in that Figure, the surgical tool 200 includes a surgical end effector 1012 that comprises an endocutter. In at least one form, the surgical tool 200 generally includes an elongated shaft assembly 1008 that has a proximal closure tube 1040 and a distal closure tube 1042 that are coupled together by an articulation joint 1011. The surgical tool 200 is operably coupled to the manipulator by a tool mounting portion, generally designated as 300. The surgical tool 200 further includes an interface 230 which mechanically and electrically couples the tool mounting portion 300 to the manipulator. In various aspects, the tool mounting portion 300 includes a tool mounting plate 302 that operably supports a plurality of (four are shown in FIG. 6) rotatable body portions, driven discs or elements 304, that each include a pair of pins 306 that extend from a surface of the driven element 304. One pin 306 is closer to an axis of rotation of each driven elements 304 than the other pin 306 on the same driven element 304, which helps to ensure positive angular alignment of the driven element 304. Interface 230 includes an adaptor portion 240 that is configured to mountingly engage the mounting plate 302 as will be further discussed below. The adaptor portion 240 may include an array of electrical connecting pins which may be coupled to a memory structure by a circuit board within the tool mounting portion 300. While interface 230 is described herein with reference to mechanical, electrical, and magnetic coupling elements, it should be understood that a wide variety of telemetry modalities might be used, including infrared, inductive coupling, or the like.

Figure 5:
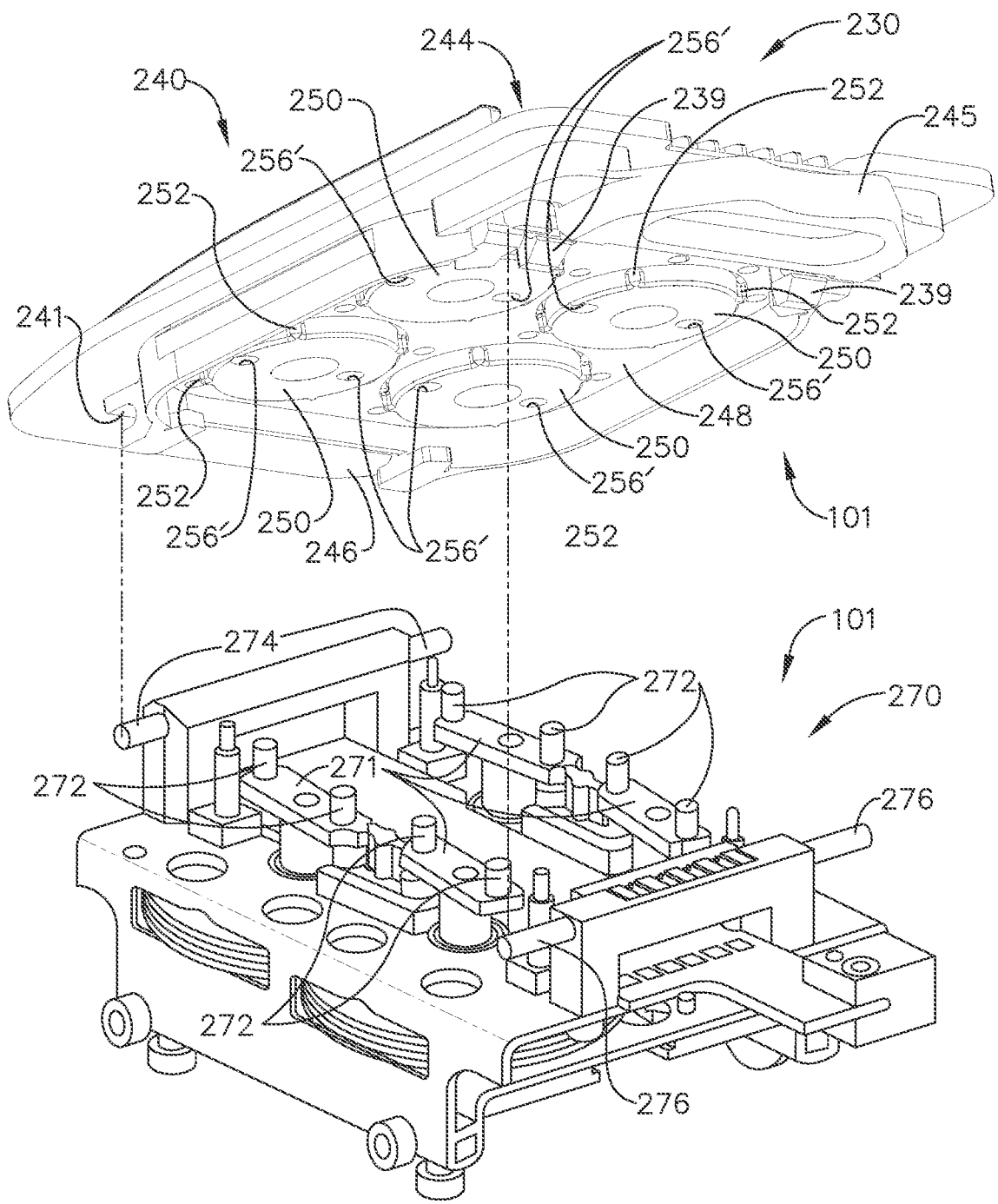
FIG. 5 is an exploded assembly view of an adapter and tool holder arrangement for attaching various surgical tools according to one aspect of this disclosure.

FIG. 5 is an exploded assembly view of an adapter and tool holder arrangement for attaching various surgical tools according to one aspect of this disclosure. A detachable latch arrangement 239 may be employed to releasably affix the adaptor 240 to the tool holder 270. As used herein, the term "tool drive assembly" when used in the context of the robotic surgical system 10, at least encompasses various aspects of the adapter 240 and tool holder 270 and which has been generally designated as 101 in FIG. 5. For example, as can be seen in FIG. 5, the tool holder 270 may include a first latch pin arrangement 274 that is sized to be received in corresponding clevis slots 241 provided in the adaptor 240. In addition, the tool holder 270 may further have second latch pins 276 that are sized to be retained in corresponding latch devises in the adaptor 240. In at least one form, a latch assembly 245 is movably supported on the adapter 240 and is biasable between a first latched position wherein the latch pins 276 are retained within their respective latch clevis and an unlatched position wherein the second latch pins 276 may be into or removed from the latch devises. A spring or springs (not shown) are employed to bias the latch assembly into the latched position. A lip on the tool side 244 of adaptor 240 may slidably receive laterally extending tabs of tool mounting housing 301. The adaptor portion 240 may include an array of electrical connecting pins 242 which may be coupled to a memory structure by a circuit board within the tool mounting portion 300. While interface 230 is described herein with reference to mechanical, electrical, and magnetic coupling elements, it should be understood that a wide variety of telemetry modalities might be used, including infrared, inductive coupling, or the like.

As shown in FIGS. 4-6 the adapter portion 240 generally includes a tool side 244 and a holder side 246. In various forms, a plurality of rotatable bodies 250 are mounted to a floating plate 248 which has a limited range of movement relative to the surrounding adaptor structure normal to the major surfaces of the adaptor 240. Axial movement of the floating plate 248 helps decouple the rotatable bodies 250 from the tool mounting portion 300 when the levers 303 along the sides of the tool mounting portion housing 301 are actuated. Other mechanisms/arrangements may be employed for releasably coupling the tool mounting portion 300 to the adaptor 240. In at least one form, rotatable bodies 250 are resiliently mounted to floating plate 248 by resilient radial members which extend into a circumferential indentation about the rotatable bodies 250. The rotatable bodies 250 can move axially relative to plate 248 by deflection of these resilient structures. When disposed in a first axial position (toward tool side 244) the rotatable bodies 250 are free to rotate without angular limitation. However, as the rotatable bodies 250 move axially toward tool side 244, tabs 252 (extending radially from the rotatable bodies 250) laterally engage detents on the floating plates so as to limit angular rotation of the rotatable bodies 250 about their axes. This limited rotation can be used to help drivingly engage the rotatable bodies 250 with drive pins 272 of a corresponding tool holder portion 270 of the robotic system 10, as the drive pins 272 will push the rotatable bodies 250 into the limited rotation position until the pins 11234 are aligned with (and slide into) openings 256'. Openings 256 on the tool side 244 and openings 256' on the holder side 246 of rotatable bodies 250 are configured to accurately align the driven elements 304 of the tool mounting portion 300 with the drive elements 271 of the tool holder 270. As described above regarding inner and outer pins 306 of driven elements 304, the openings 256, 256' are at differing distances from the axis of rotation on their respective rotatable bodies 250 so as to ensure that the alignment is not 180 degrees from its intended position. Additionally, each of the openings 256 is slightly radially elongated so as to fittingly receive the pins 306 in the circumferential orientation. This allows the pins 306 to slide radially within the openings 256, 256' and accommodate some axial misalignment between the tool 200 and tool holder 270, while minimizing any angular misalignment and backlash between the drive and driven elements. Openings 256 on the tool side 244 are offset by about 90 degrees from the openings 256' (shown in broken lines) on the holder side 246.

FIG. 6 is a partial bottom perspective view of the surgical tool aspect of FIG. 4. As shown in FIGS. 6-10, the surgical end effector 1012 is attached to the tool mounting portion 300 by an elongated shaft assembly 1008 according to various aspects. As shown in the illustrated aspect, the shaft assembly 1008 includes an articulation joint generally indicated as 1011 that enables the surgical end effector 1012 to be selectively articulated about an articulation axis AA-AA that is substantially transverse to a longitudinal tool axis LT-LT. See FIG. 7. In other aspects, the articulation joint is omitted. In various aspects, the shaft assembly 1008 may include a closure tube assembly 1009 that comprises a proximal closure tube 1040 and a distal closure tube 1042 that are pivotably linked by a pivot links 1044 and operably supported on a spine assembly generally depicted as 1049. In the illustrated aspect, the spine assembly 1049 comprises a distal spine portion 1050 that is attached to the elongated channel 1022 and is pivotally coupled to the proximal spine portion 1052. The closure tube assembly 1009 is configured to axially slide on the spine assembly 1049 in response to actuation motions applied thereto. The distal closure tube 1042 includes an opening 1045 into which the tab 1027 on the anvil 1024 is inserted in order to facilitate opening of the anvil 1024 as the distal closure tube 1042 is moved axially in the proximal direction "PD". The closure tubes 1040, 1042 may be made of electrically conductive material (such as metal) so that they may serve as part of the antenna, as described above. Components of the main drive shaft assembly (e.g., the drive shafts 1048, 1050) may be made of a nonconductive material (such as plastic). The anvil 1024 may be pivotably opened and closed at a pivot point 1025 located at the proximal end of the elongated channel 1022.

Figure 8:
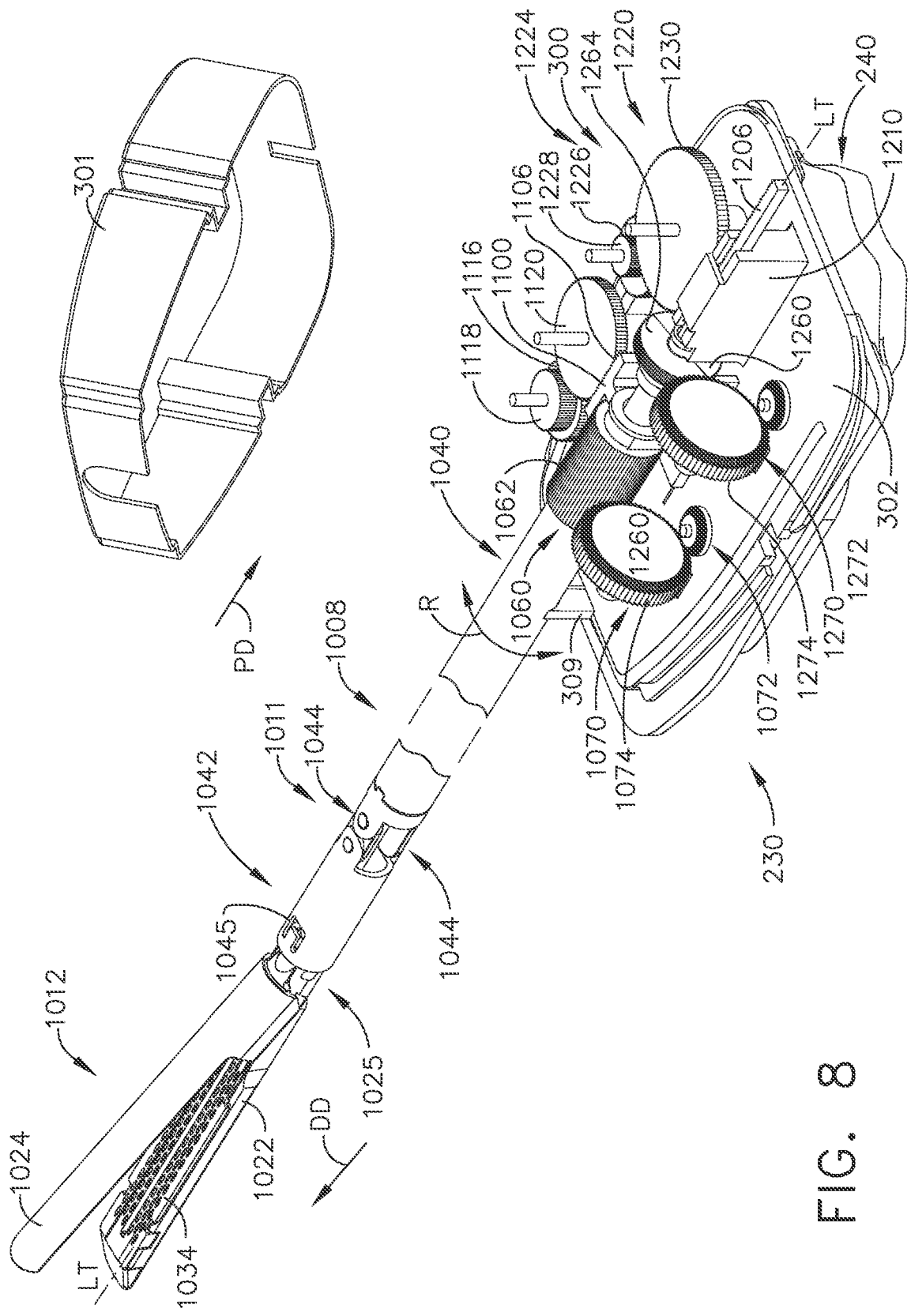
FIG. 8 is a rear perspective view of the surgical tool of FIG. 105 with the tool mounting housing removed according to one aspect of this disclosure.

In use, it may be desirable to rotate the surgical end effector 1012 about the longitudinal tool axis LT-LT. In at least one aspect, the tool mounting portion 300 includes a rotational transmission assembly 1069 that is configured to receive a corresponding rotary output motion from the tool drive assembly 101 of the robotic surgical system 10 and convert that rotary output motion to a rotary control motion for rotating the elongated shaft assembly 1008 (and surgical end effector 1012) about the longitudinal tool axis LT-LT. In various aspects, for example, the proximal end 1060 of the proximal closure tube 1040 is rotatably supported on the tool mounting plate 302 of the tool mounting portion 300 by a forward support cradle 309 and a closure sled 1100 that is also movably supported on the tool mounting plate 302. In at least one form, the rotational transmission assembly 1069 includes a tube gear segment 1062 that is formed on (or attached to) the proximal end 1060 of the proximal closure tube 1040 for operable engagement by a rotational gear assembly 1070 that is operably supported on the tool mounting plate 302. As shown in FIG. 8, the rotational gear assembly 1070, in at least one aspect, comprises a rotation drive gear 1072 that is coupled to a corresponding first one of the driven discs or elements 304 on the adapter side 307 of the tool mounting plate 302 when the tool mounting portion 300 is coupled to the tool drive assembly 101. See FIG. 6. The rotational gear assembly 1070 further comprises a rotary driven gear 1074 that is rotatably supported on the tool mounting plate 302 in meshing engagement with the tube gear segment 1062 and the rotation drive gear 1072. Application of a first rotary output motion from the tool drive assembly 101 of the robotic surgical system 10 to the corresponding driven element 304 will thereby cause rotation of the rotation drive gear 1072. Rotation of the rotation drive gear 1072 ultimately results in the rotation of the elongated shaft assembly 1008 (and the surgical end effector 1012) about the longitudinal tool axis LT-LT (represented by arrow "R" in FIG. 8). It will be appreciated that the application of a rotary output motion from the tool drive assembly 101 in one direction will result in the rotation of the elongated shaft assembly 1008 and surgical end effector 1012 about the longitudinal tool axis LT-LT in a first direction and an application of the rotary output motion in an opposite direction will result in the rotation of the elongated shaft assembly 1008 and surgical end effector 1012 in a second direction that is opposite to the first direction.

Figure 10:
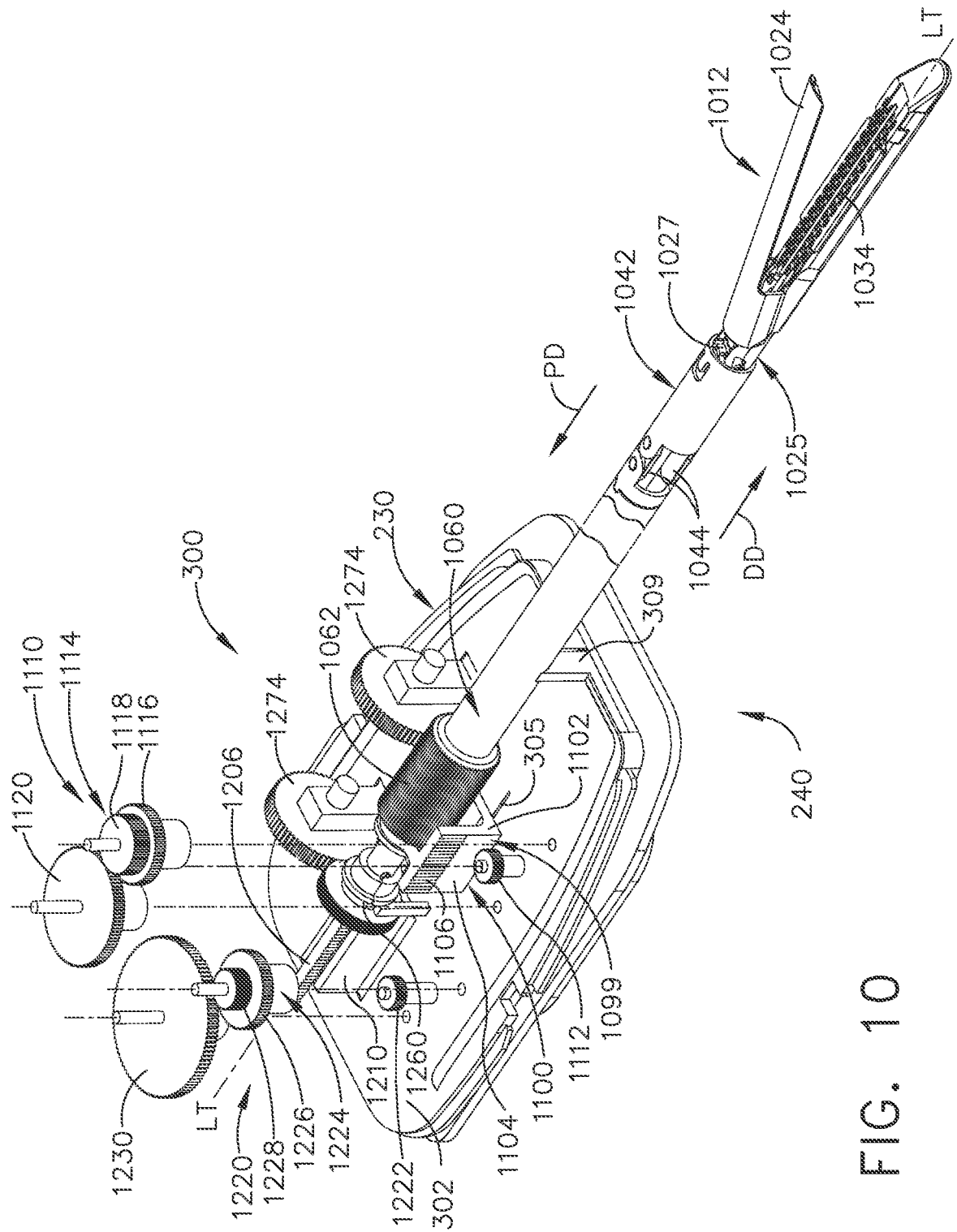
FIG. 10 is a partial exploded perspective view of the surgical tool of FIG. 6 according to one aspect of this disclosure.

In at least one aspect, the closure of the anvil 1024 relative to the staple cartridge 1034 is accomplished by axially moving the closure tube assembly 1009 in the distal direction "DD" on the spine assembly 1049. As indicated above, in various aspects, the proximal end 1060 of the proximal closure tube 1040 is supported by the closure sled 1100 which comprises a portion of a closure transmission, generally depicted as 1099. In at least one form, the closure sled 1100 is configured to support the closure tube 1009 on the tool mounting plate 320 such that the proximal closure tube 1040 can rotate relative to the closure sled 1100, yet travel axially with the closure sled 1100. In particular, the closure sled 1100 has an upstanding tab 1101 that extends into a radial groove 1063 in the proximal end portion of the proximal closure tube 1040. In addition, as can be seen in FIG. 10, the closure sled 1100 has a tab portion 1102 that extends through a slot 305 in the tool mounting plate 302. The tab portion 1102 is configured to retain the closure sled 1100 in sliding engagement with the tool mounting plate 302. In various aspects, the closure sled 1100 has an upstanding portion 1104 that has a closure rack gear 1106 formed thereon. The closure rack gear 1106 is configured for driving engagement with a closure gear assembly 1110. The knife rack gear 1106 is slidably supported within a rack housing 1210 that is attached to the tool mounting plate 302 such that the knife rack gear 1106 is retained in meshing engagement with a knife gear assembly 1220.

Figure 9:
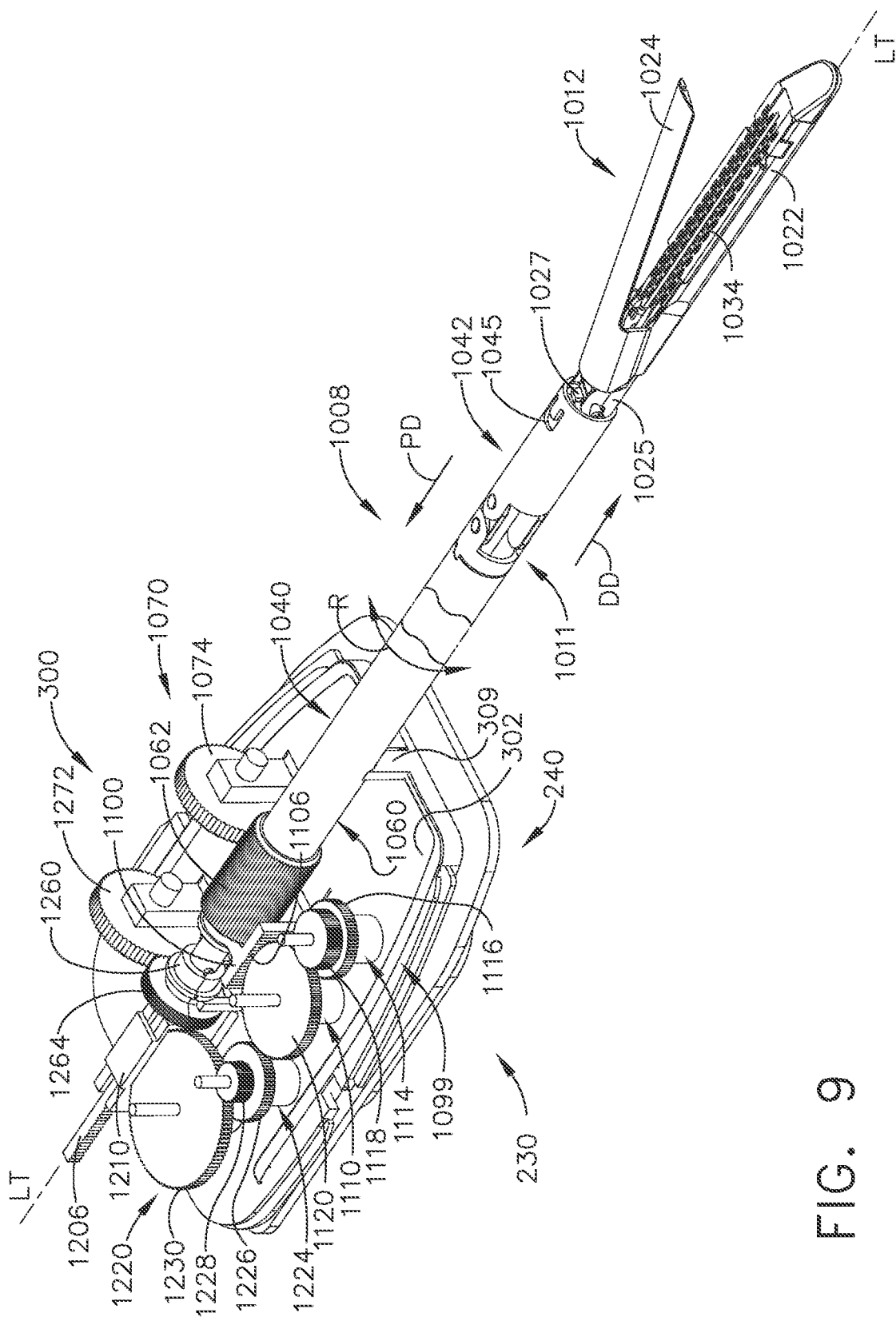
FIG. 9 is a front perspective view of the surgical tool of FIG. 6 with the tool mounting housing removed according to one aspect of this disclosure.

In various forms, the closure gear assembly 1110 includes a closure spur gear 1112 that is coupled to a corresponding second one of the driven discs or elements 304 on the adapter side 307 of the tool mounting plate 302. See FIG. 6. Thus, application of a second rotary output motion from the tool drive assembly 101 of the robotic surgical system 10 to the corresponding second driven element 304 will cause rotation of the closure spur gear 1112 when the tool mounting portion 300 is coupled to the tool drive assembly 101. The closure gear assembly 1110 further includes a closure reduction gear set 1114 that is supported in meshing engagement with the closure spur gear 1112. As can be seen in FIGS. 9 and 10, the closure reduction gear set 1114 includes a driven gear 1116 that is rotatably supported in meshing engagement with the closure spur gear 1112. The closure reduction gear set 1114 further includes a first closure drive gear 1118 that is in meshing engagement with a second closure drive gear 1120 that is rotatably supported on the tool mounting plate 302 in meshing engagement with the closure rack gear 1106. Thus, application of a second rotary output motion from the tool drive assembly 101 of the robotic surgical system 10 to the corresponding second driven element 11304 will cause rotation of the closure spur gear 1112 and the closure transmission 1110 and ultimately drive the closure sled 1100 and closure tube assembly 1009 axially. The axial direction in which the closure tube assembly 1009 moves ultimately depends upon the direction in which the second driven element 304 is rotated. For example, in response to one rotary output motion received from the tool drive assembly 101 of the robotic surgical system 10, the closure sled 1100 will be driven in the distal direction "DD" and ultimately drive the closure tube assembly 101 in the distal direction. As the distal closure tube 1042 is driven distally, the end of the closure tube segment 1042 will engage a portion of the anvil 1024 and cause the anvil 1024 to pivot to a closed position. Upon application of an "opening" out put motion from the tool drive assembly 101 of the robotic surgical system 10, the closure sled 1100 and shaft assembly 1008 will be driven in the proximal direction "PD". As the distal closure tube 1042 is driven in the proximal direction, the opening 1045 therein interacts with the tab 1027 on the anvil 1024 to facilitate the opening thereof. In various aspects, a spring (not shown) may be employed to bias the anvil to the open position when the distal closure tube 1042 has been moved to its starting position. In various aspects, the various gears of the closure gear assembly 1110 are sized to generate the necessary closure forces needed to satisfactorily close the anvil 1024 onto the tissue to be cut and stapled by the surgical end effector 1012. For example, the gears of the closure transmission 1110 may be sized to generate approximately 70-120 pounds.

FIG. 11A is a partial cross-sectional side view of the surgical tool 200 of FIG. 6 and FIG. 11B is an enlarged cross-sectional view of a portion of the surgical tool depicted in FIG. 11A according to one aspect of this disclosure. With reference to FIGS. 11A and 11B, the distal end 1202 of the knife bar 1200 is attached to the cutting instrument 1032. The proximal end 1204 of the knife bar 1200 is rotatably affixed to a knife rack gear 1206 such that the knife bar 1200 is free to rotate relative to the knife rack gear 1206. The knife rack gear 1206 is slidably supported within a rack housing 1210 that is attached to the tool mounting plate 302 such that the knife rack gear 1206 is retained in meshing engagement with a knife gear assembly 1220. More specifically and with reference to FIG. 10, in at least one aspect, the knife gear assembly 1220 includes a knife spur gear 1222 that is coupled to a corresponding third one of the driven discs or elements 304 on the adapter side 307 of the tool mounting plate 302. See FIG. 6. Thus, application of another rotary output motion from the robotic system 10 through the tool drive assembly 101 to the corresponding third driven element 304 will cause rotation of the knife spur gear 1222. The knife gear assembly 1220 further includes a knife gear reduction set 1224 that includes a first knife drive gear 1226 and a second knife drive gear 1228. The knife gear reduction set 1224 is rotatably mounted to the tool mounting plate 302 such that the first knife drive gear 1226 is in meshing engagement with the knife spur gear 1222. Likewise, the second knife drive gear 1228 is in meshing engagement with a third knife drive gear 1230 that is rotatably supported on the tool mounting plate 302 in meshing engagement with the knife rack gear 1206. In various aspects, the gears of the knife gear assembly 1220 are sized to generate the forces needed to drive the cutting element 1032 through the tissue clamped in the surgical end effector 1012 and actuate the staples therein. For example, the gears of the knife drive assembly 1230 may be sized to generate approximately 40 to 100 pounds. It will be appreciated that the application of a rotary output motion from the tool drive assembly 101 in one direction will result in the axial movement of the cutting instrument 1032 in a distal direction and application of the rotary output motion in an opposite direction will result in the axial travel of the cutting instrument 1032 in a proximal direction.

In various aspects, the surgical tool 200 employs an articulation system that includes an articulation joint 12011 that enables the surgical end effector 1012 to be articulated about an articulation axis AA-AA that is substantially transverse to the longitudinal tool axis LT-LT. In at least one aspect, the surgical tool 200 includes first and second articulation bars 1250a, 1250b that are slidably supported within corresponding passages provided through the proximal spine portion 1052. In at least one form, the first and second articulation bars 1250a, 1250b are actuated by an articulation transmission that is operably supported on the tool mounting plate 302. Each of the articulation bars 1250a, 1250b has a proximal end that has a guide rod protruding therefrom which extend laterally through a corresponding slot in the proximal end portion of the proximal spine portion and into a corresponding arcuate slot in an articulation nut 1260 which comprises a portion of the articulation transmission. The articulation bar 1250a has a guide rod 1254 which extends laterally through a corresponding slot in the proximal end portion of the distal spine portion 1050 and into a corresponding arcuate slot in the articulation nut 1260. In addition, the articulation bar 1250a has a distal end that is pivotally coupled to the distal spine portion 1050 by, for example, a pin and articulation bar 1250b has a distal end that is pivotally coupled to the distal spine portion 1050 by a pin. In particular, the articulation bar 1250a is laterally offset in a first lateral direction from the longitudinal tool axis LT-LT and the articulation bar 1250b is laterally offset in a second lateral direction from the longitudinal tool axis LT-LT. Thus, axial movement of the articulation bars 1250a, 1250b in opposing directions will result in the articulation of the distal spine portion 1050 as well as the surgical end effector 1012 attached thereto about the articulation axis AA-AA as will be discussed in further detail below.

Articulation of the surgical end effector 1012 is controlled by rotating the articulation nut 1260 about the longitudinal tool axis LT-LT. The articulation nut 1260 is rotatably journaled on the proximal end portion of the distal spine portion 1050 and is rotatably driven thereon by an articulation gear assembly 1270. More specifically and with reference to FIG. 8, in at least one aspect, the articulation gear assembly 1270 includes an articulation spur gear 1272 that is coupled to a corresponding fourth one of the driven discs or elements 304 on the adapter side 307 of the tool mounting plate 302. Thus, application of another rotary input motion from the robotic system 10 through the tool drive assembly 101 to the corresponding fourth driven element 304 will cause rotation of the articulation spur gear 1272 when the interface 230 is coupled to the tool holder 270. An articulation drive gear 1274 is rotatably supported on the tool mounting plate 302 in meshing engagement with the articulation spur gear 1272 and a gear portion 1264 of the articulation nut 1260 as shown. The articulation nut 1260 has a shoulder 1266 formed thereon that defines an annular groove 1267 for receiving retaining posts 1268 therein. Retaining posts 1268 are attached to the tool mounting plate 302 and serve to prevent the articulation nut 1260 from moving axially on the proximal spine portion 1052 while maintaining the ability to be rotated relative thereto. Thus, rotation of the articulation nut 1260 in a first direction, will result in the axial movement of the articulation bar 1250a in a distal direction "DD" and the axial movement of the articulation bar 1250b in a proximal direction "PD" because of the interaction of the guide rods 1254 with the spiral slots in the articulation gear 1260. Similarly, rotation of the articulation nut 1260 in a second direction that is opposite to the first direction will result in the axial movement of the articulation bar 1250a in the proximal direction "PD" as well as cause articulation bar 1250b to axially move in the distal direction "DD". Thus, the surgical end effector 1012 may be selectively articulated about articulation axis "AA-AA" in a first direction "FD" by simultaneously moving the articulation bar 1250a in the distal direction "DD" and the articulation bar 1250b in the proximal direction "PD". Likewise, the surgical end effector 1012 may be selectively articulated about the articulation axis "AA-AA" in a second direction "SD" by simultaneously moving the articulation bar 1250*a* in the proximal direction "PD" and the articulation bar 1250*b* in the distal direction "DD."

The tool aspect described above employs an interface arrangement that is particularly well-suited for mounting the robotically controllable medical tool onto at least one form of robotic arm arrangement that generates at least four different rotary control motions. Those of ordinary skill in the art will appreciate that such rotary output motions may be selectively controlled through the programmable control systems employed by the robotic system/controller. For example, the tool arrangement described above may be well-suited for use with those robotic systems manufactured by Intuitive Surgical, Inc. of Sunnyvale, Calif., U.S.A., many of which may be described in detail in various patents incorporated herein by reference. The unique and novel aspects of various aspects of the present invention serve to utilize the rotary output motions supplied by the robotic system to generate specific control motions having sufficient magnitudes that enable end effectors to cut and staple tissue. Thus, the unique arrangements and principles of various aspects of the present invention may enable a variety of different forms of the tool systems disclosed and claimed herein to be effectively employed in connection with other types and forms of robotic systems that supply programmed rotary or other output motions. In addition, as will become further apparent as the present Detailed Description proceeds, various end effector aspects of the present invention that require other forms of actuation motions may also be effectively actuated utilizing one or more of the control motions generated by the robotic system.

Figure 12:
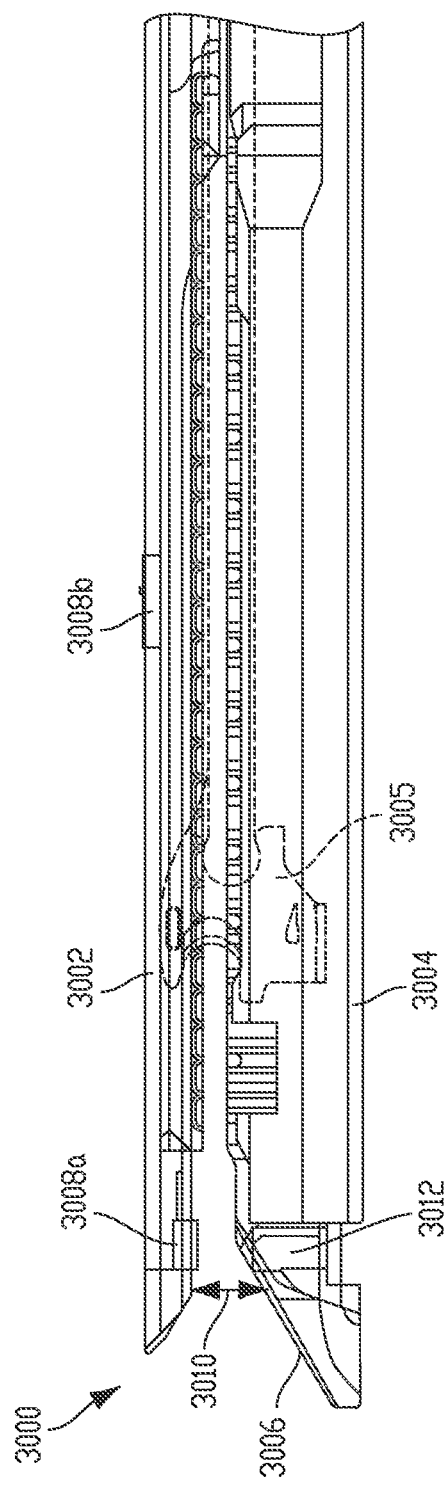
FIG. 12 illustrates one aspect of an end effector comprising a first sensor and a second according to one aspect of this disclosure.

FIG. 12 illustrates one aspect of an end effector 3000 comprising a first sensor 3008*a* and a second sensor 3008*b*. The first and second sensors 3008*a*, 3008*b* are provided on the cartridge deck to determine tissue location using segmented electrodes. Accordingly, the first and second sensors 3008*a*, 3008*b* enable sensing the load on the closure tube, the position of the closure tube, the firing member at the rack and the position of the firing member coupled to the I-beam 3005, the portion of the cartridge that contains tissue, the load and position on the articulation rods. The end effector 3000 comprises a first jaw member, or anvil, 3002 pivotally coupled to a second jaw member 3004. The second jaw member 3004 is configured to receive a staple cartridge 3006 therein. The staple cartridge 3006 comprises a plurality of staples. The plurality of staples is deployable from the staple cartridge 3006 during a surgical operation. The end effector 3000 comprises a first sensor 3008*a*. The first sensor 3008*a* is configured to measure one or more parameters of the end effector 3000. For example, in one aspect, the first sensor 3008*a* is configured to measure the gap 3010 between the anvil 3002 and the second jaw member 3004. The first sensor 3008*a* may comprise, for example, a Hall effect sensor configured to detect a magnetic field generated by a magnet 3012 embedded in the second jaw member 3004 and/or the staple cartridge 3006. As another example, in one aspect, the first sensor 3008*a* is configured to measure one or more forces exerted on the anvil 3002 by the second jaw member 3004 and/or tissue clamped between the anvil 3002 and the second jaw member 3004. The sensors 3008*a*, 3008*b* may be employed to measure tissue thickness, force, displacement, compression, tissue impedance, and tissue location within the end effector 3000.

The end effector 3000 comprises a second sensor 3008*b*. The second sensor 3008*b* is configured to measure one or more parameters of the end effector 3000. For example, in various aspects, the second sensor 3008*b* may comprise a strain gauge configured to measure the magnitude of the strain in the anvil 3002 during a clamped condition. The strain gauge provides an electrical signal whose amplitude varies with the magnitude of the strain. In various aspects, the first sensor 3008*a* and/or the second sensor 3008*b* may comprise, for example, a magnetic sensor such as, for example, a Hall effect sensor, a strain gauge, a pressure sensor, a force sensor, an inductive sensor such as, for example, an eddy current sensor, a resistive sensor, a capacitive sensor, an optical sensor, and/or any other suitable sensor for measuring one or more parameters of the end effector 3000. The first sensor 3008*a* and the second sensor 3008*b* may be arranged in a series configuration and/or a parallel configuration. In a series configuration, the second sensor 3008*b* may be configured to directly affect the output of the first sensor 3008*a*. In a parallel configuration, the second sensor 3008*b* may be configured to indirectly affect the output of the first sensor 3008*a*.

In one aspect, the first sensor 3008*a* may be configured to measure the gap 3010 between the anvil 3002 and the second jaw member 3004. The gap 3010 is representative of the thickness and/or compressibility of a tissue section clamped between the anvil 3002 and the staple cartridge 3006. The first sensor 3008*a* may comprise, for example, a Hall effect sensor configured to detect a magnetic field generated by a magnet 3012 coupled to the second jaw member 3004 and/or the staple cartridge 3006. Measuring at a single location accurately describes the compressed tissue thickness for a calibrated full bit of tissue, but may provide inaccurate results when a partial bite of tissue is placed between the anvil 3002 and the second jaw member 3004. A partial bite of tissue, either a proximal partial bite or a distal partial bite, changes the clamping geometry of the anvil 3002.

In some aspects, the second sensor 3008*b* may be configured to detect one or more parameters indicative of a type of tissue bite, for example, a full bite, a partial proximal bite, and/or a partial distal bite. In some aspects, the thickness measurement of the first sensor 3008*a* may be provided to an output device of the robotic surgical system 10 coupled to the end effector 3000. For example, in one aspect, the end effector 3000 is coupled to the robotic surgical system 10 comprising a display. The measurement of the first sensor 3008*a* is provided to a processor.

In another aspect, the end effector 3000 may comprise a plurality of second sensors configured to measure an amplitude of strain exerted on the anvil 3002 during a clamping procedure. In another aspect, the plurality of sensors allows a robust tissue thickness sensing process to be implemented. By detecting various parameters along the length of the anvil 3202, the plurality of sensors allow a surgical instrument, such as, for example, the surgical instrument 10, to calculate the tissue thickness in the jaws regardless of the bite, for example, a partial or full bite. In some aspects, the plurality of sensors comprises a plurality of strain gauges. The plurality of strain gauges is configured to measure the strain at various points on the anvil 3002. The amplitude and/or the slope of the strain at each of the various points on the anvil 3002 can be used to determine the thickness of tissue in between the anvil 3002 and the staple cartridge 3006. The plurality of strain gauges may be configured to optimize maximum amplitude and/or slope differences based on clamping dynamics to determine thickness, tissue placement, and/or material properties of the tissue. Time based monitoring of the plurality of sensors during clamping allows a processor, such as, for example, a primary processor, to utilize algorithms and look-up tables to recognize tissue characteristics and clamping positions and dynamically adjust the end effector 3000 and/or tissue clamped between the anvil 3002 and the staple cartridge 3006.

Figure 13B:
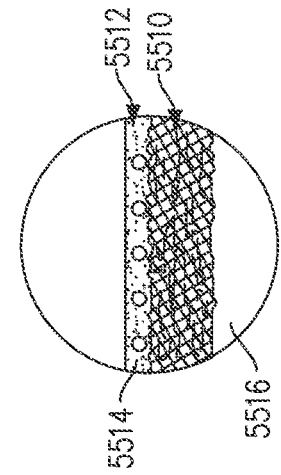
FIG. 13B illustrates a detail view of a portion of the tissue compensator shown in FIG. 13A according to one aspect of this disclosure.
Figure 13A:
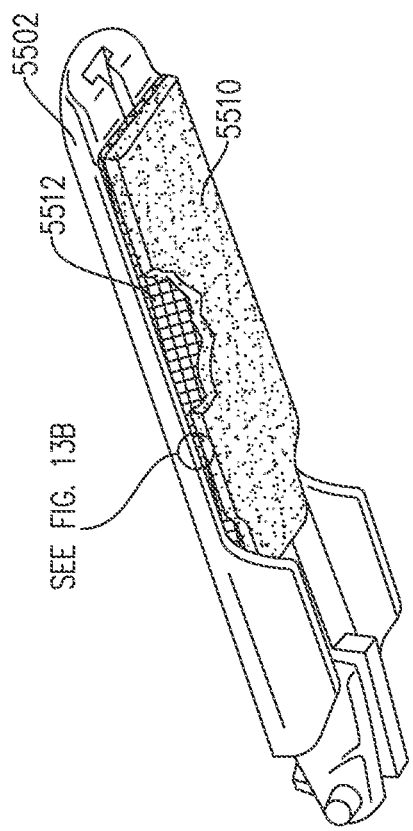
FIG. 13A illustrates an aspect wherein the tissue compensator is removably attached to the anvil portion of the end effector according to one aspect of this disclosure.

FIG. 13A illustrates an aspect of an end effector 5500 comprising a layer of conductive elements 5512. The end effector 5500 is similar to the end effector 3000 described above. The end effector 5500 comprises a first jaw member, or anvil, 5502 pivotally coupled to a second jaw member 5504. The second jaw member 5504 is configured to receive a staple cartridge 5506 therein. FIG. 13B illustrates a detail view of a portion of the tissue compensator shown in FIG. 13A. The conductive elements 5512 can comprise any combination of conductive materials in any number of configurations, such as for instance coils of wire, a mesh or grid of wires, conductive strips, conductive plates, electrical circuits, microprocessors, or any combination thereof. The layer containing conductive elements 5512 can be located on the anvil-facing surface 5514 of the tissue compensator 5510. Alternatively or additionally, the layer of conductive elements 5512 can be located on the staple cartridge-facing surface 5516 of the tissue compensator 5510. The conductive elements 5512 may be employed to measure tissue thickness, force, displacement, compression, tissue impedance, and tissue location within the end effector 5500. Additional examples are disclosed in U.S. Patent Application Publication No. 2016/0066912, now U.S. Pat. No. 10,111,679, which is incorporated herein by reference.

Figure 13C:
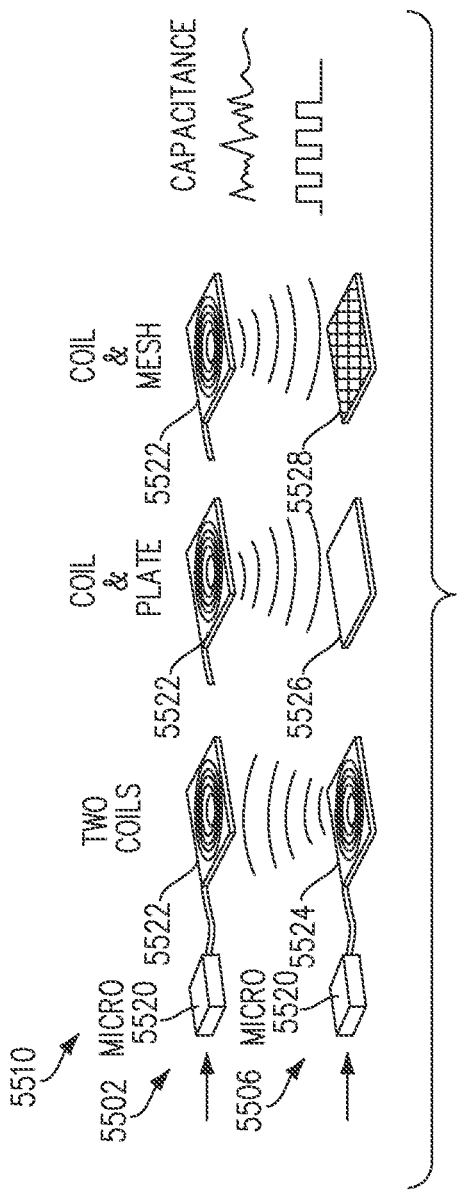
FIG. 13C illustrates various example aspects that use the layer of conductive elements and conductive elements in the staple cartridge to detect the distance between the anvil and the upper surface of the staple cartridge according to one aspect of this disclosure.

FIG. 13C illustrates various example aspects that use the layer of conductive elements 5512 and conductive elements 5524, 5526, and 5528 in the staple cartridge 5506 to detect the distance between the anvil 5502 and the upper surface of the staple cartridge 5506. The distance between the anvil 5502 and the staple cartridge 5506 indicates the amount and/or density of tissue 5518 compressed therebetween. This distance can additionally or alternatively indicate which areas of the end effector 5500 contain tissue. The tissue 5518 thickness, density, and/or location can be communicated to the operator of the surgical instrument 10.

In the illustrated example aspects, the layer of conductive elements 5512 is located on the anvil-facing surface 5514 of the tissue compensator 5510, and comprises one or more coils of wire 5522 in communication with a control circuit comprising a microprocessor 5520. The microprocessor 5500 can be located in the end effector 5500 or any component thereof, or can be located in the tool mounting housing 301 of the instrument, or can comprise any microprocessor or microcontroller previously described. In the illustrated example aspects, the staple cartridge 5506 also includes conductive elements, which can be any one of: one or more coils of wire 5524, one or more conductive plates 5526, a mesh of wires 5528, or any other convenient configuration, or any combination thereof. The conductive elements of the staple cartridge 5506 can be in communication with the same microprocessor 5520 or some other microprocessor in the robotic surgical instrument. The conductive elements 5512 may be employed to measure tissue thickness, force, displacement, compression, tissue impedance, and tissue location within the end effector 5500.

When the anvil 5502 is in a closed position and thus is compressing tissue 5518 against staple cartridge 5506, the layer of conductive elements 5512 of the tissue compensator 5510 can capacitively couple with the conductors in staple cartridge 5506. The strength of the capacitive field between the layer of conductive elements 5512 and the conductive elements of the staple cartridge 5506 can be used to determine the amount of tissue 5518 being compressed. Alternatively, the staple cartridge 5506 can comprise eddy current sensors in communication with a microprocessor 5520, wherein the eddy current sensors are operable to sense the distance between the anvil 5502 and the upper surface of the staple cartridge 5506 using eddy currents.

It is understood that other configurations of conductive elements are possible, and that the aspects of FIG. 13C are by way of example only, and not limitation. For example, in some aspects the layer of conductive elements 5512 can be located on the staple cartridge-facing surface 5516 of the tissue compensator 5510. Also, in some aspects the conductive elements 5524, 5526, and/or 5528 can be located on or within the anvil 5502. Thus in some aspects, the layer of conductive elements 5512 can capacitively couple with conductive elements in the anvil 5502 and thereby sense properties of tissue 5518 enclosed within the end effector.

It can also be recognized that a layer of conductive elements 5512 may be disposed on both the anvil-facing surface 5514 and the cartridge-facing surface 5516. A system to detect the amount, density, and/or location of tissue 5518 compressed by the anvil 5502 against the staple cartridge 5506 can comprise conductors or sensors either in the anvil 5502, the staple cartridge 5506, or both. Aspects that include conductors or sensors in both the anvil 5502 and the staple cartridge 5506 can optionally achieve enhanced results by allowing differential analysis of the signals that can be achieved by this configuration.

Figure 14A:
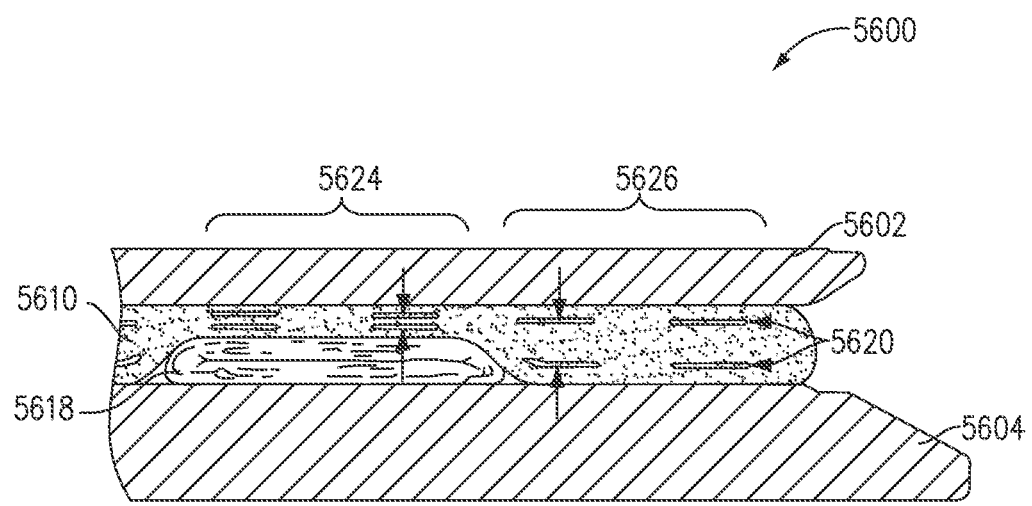
FIG. 14A illustrates an end effector comprising conductors embedded within according to one aspect of this disclosure.
Figure 14B:
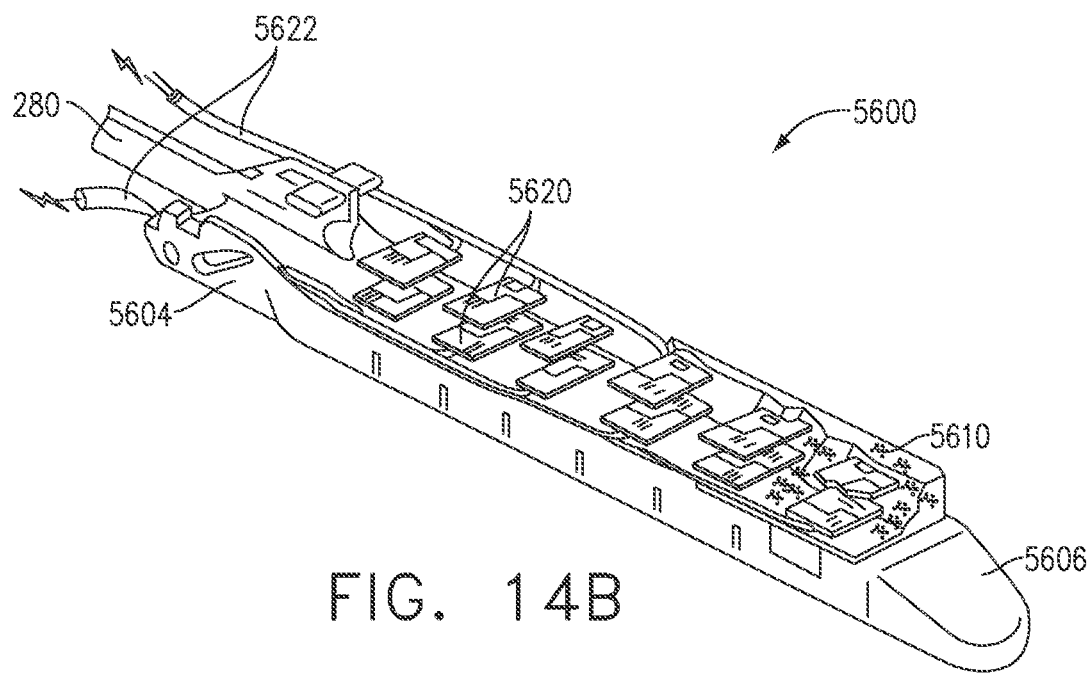
FIG. 14B illustrates an end effector comprising conductors embedded within according to one aspect of this disclosure.

Turning now to FIG. 14A, there is illustrated a close-up cutaway view of the end effector 5600 with the anvil 5602 in a closed position. FIG. 14B illustrates the end effector 5600 comprising electrical conductors 5620 embedded within according to one aspect of this disclosure. In a closed position, the anvil 5602 can compress tissue 5618 between the tissue compensator 5610 and the staple cartridge 5606. In some cases, only a part of the end effector 5600 may be enclosing the tissue 5618. In areas of the end effector 5600 that are enclosing tissue 5618, in areas of greater compression 5624, the array of conductors 5620 will also be compressed, while in uncompressed 5626 areas, the array of conductors 5620 will be further apart. Hence, the conductivity, resistance, capacitance, and/or some other electrical property between the array of conductors 5620 can indicate which areas of the end effector 5600 contain tissue. The array of conductors 5620 may be employed to measure tissue thickness, force, displacement, compression, tissue impedance, and tissue location within the end effector 5600.

With reference to FIGS. 14A and 14B, the end effector 5600 comprising a tissue compensator 5610 further comprising conductors 5620 embedded within. The end effector 5600 comprises a first jaw member, or anvil 5602 pivotally coupled to a second jaw member 5604. The second jaw member 5604 is configured to receive a staple cartridge 5606 therein. In some aspects, the end effector 5600 further comprises a tissue compensator 5610 removably positioned on the anvil 5602 or the staple cartridge 5606.

Figure 30:
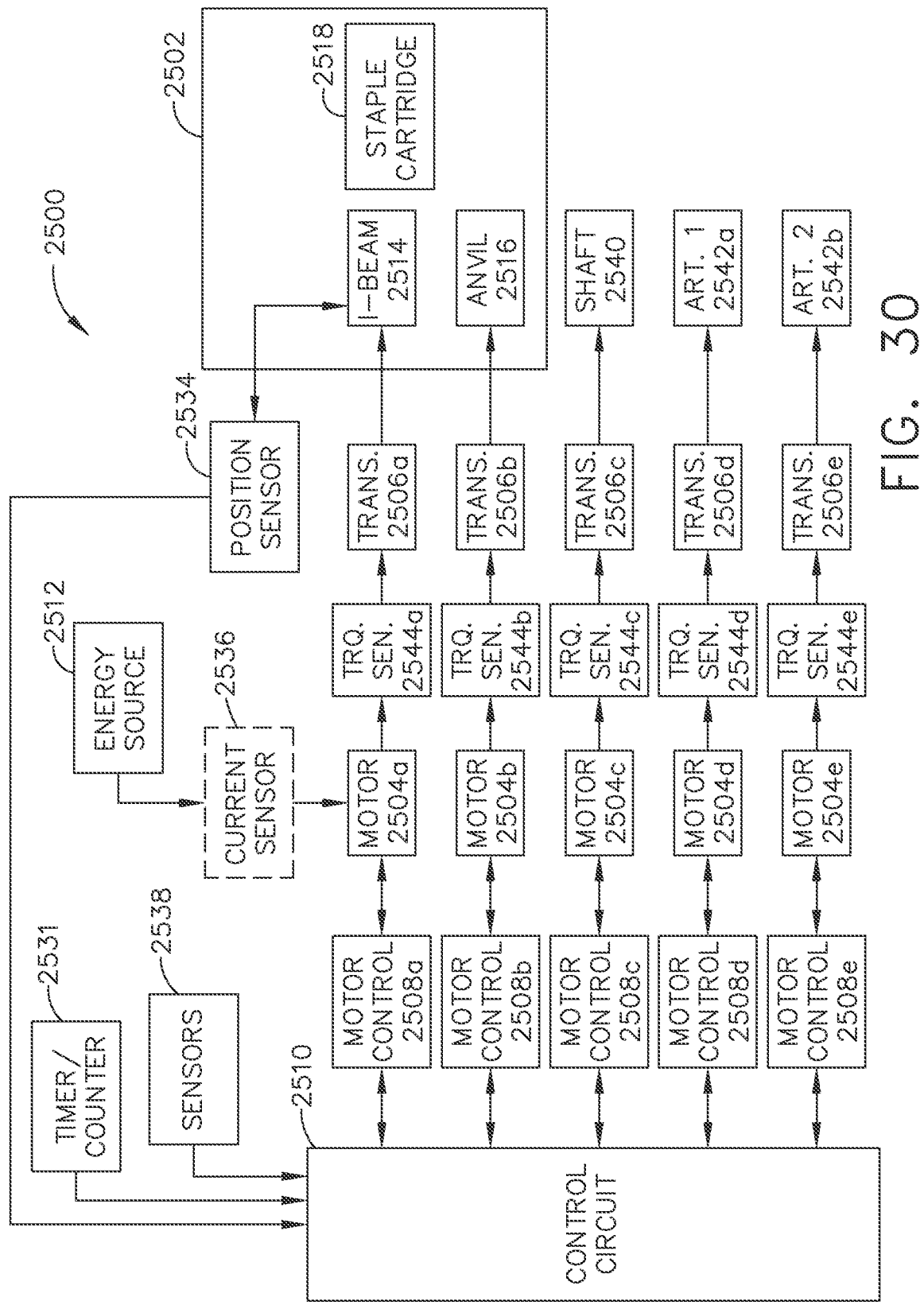
FIG. 30 is a schematic diagram of a robotic surgical instrument configured to operate the surgical tool described herein according to one aspect of this disclosure.

An array of conductors 5620 are embedded within the material that comprises the tissue compensator 5610. The array of conductors 5620 can be arranged in an opposing configuration, and the opposing elements can be separated by insulating material. The array of conductors 5620 are each coupled to one or more conductive wires 5622. The conductive wires 5622 allow the array of conductors 5620 to communicate with a microprocessor or control circuit 961 (FIG. 22), 800 (FIG. 23), 810 (FIG. 24), 820 (FIG. 25), 4420 (FIG. 26), 2510 (FIG. 30). The array of conductors 5620 may span the width of the tissue compensator 5610 such that they will be in the path of a cutting member or knife bar 280. As the knife bar 280 advances, it will sever, destroy, or otherwise disable the conductors 5620, and thereby indicate its position within the end effector 5600. The array of conductors 5610 can comprise conductive elements, electric circuits, microprocessors, or any combination thereof.

Figure 15A:
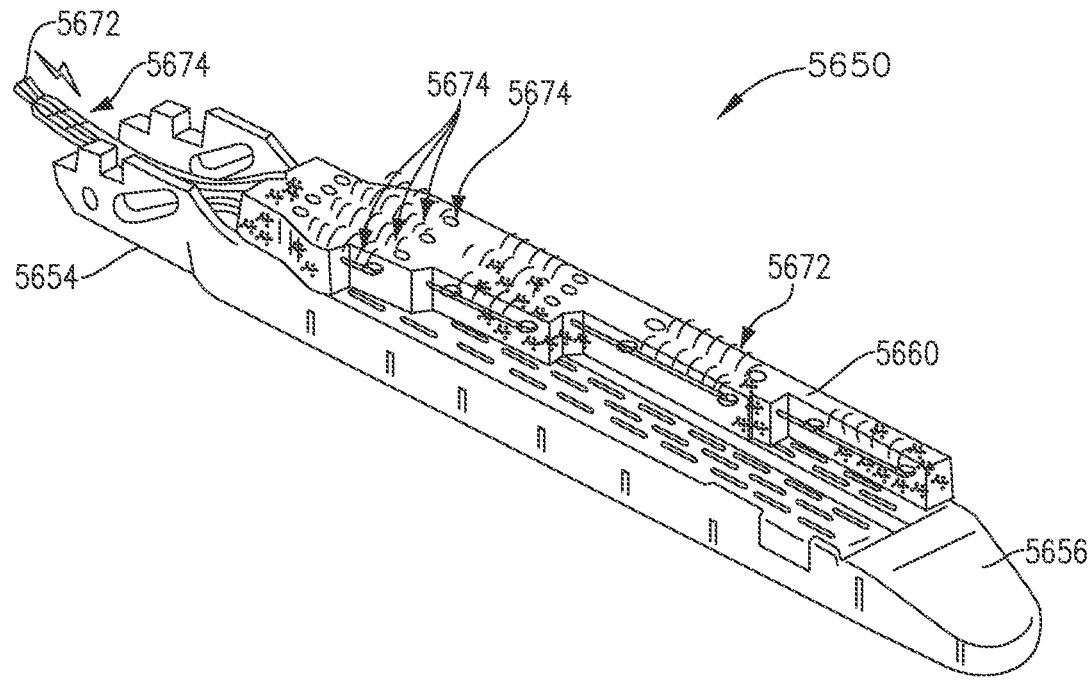
FIG. 15A illustrates a cutaway view of the staple cartridge according to one aspect of this disclosure.
Figure 15B:
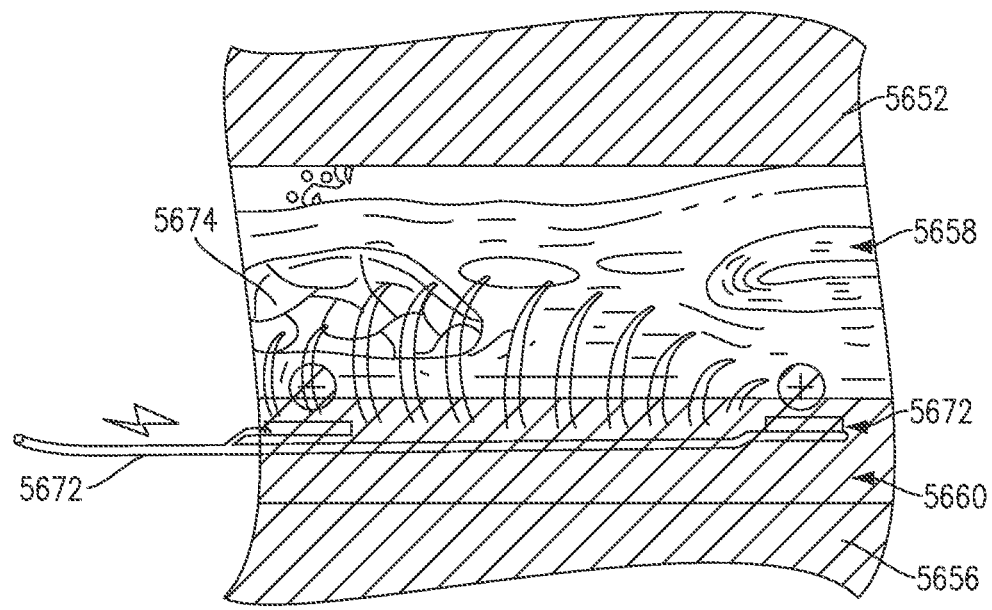
FIG. 15B illustrates a cutaway view of the staple cartridge shown in FIG. 15A illustrating conductors embedded within the end effector according to one aspect of this disclosure.

FIGS. 15A and 15B illustrate an aspect of an end effector 5650 further comprising conductors 5662 embedded therein. The end effector 5650 comprises a first jaw member, or anvil, 5652 pivotally coupled to a second jaw member 5654. The second jaw member 5654 is configured to receive a staple cartridge 5656 therein. FIG. 15A illustrates a cutaway view of the staple cartridge 5656. The cutaway view illustrates conductors 5670 embedded within the end effector. Each of the conductors 5672 is coupled to a conductive wire 5672. The conductive wires 5672 allow the array of conductors 5672 to communicate with a microprocessor. The conductors 5672 may comprise conductive elements, electric circuits, microprocessors, or any combination thereof. FIG. 15B illustrates a close-up side view of the end effector 5650 with the anvil 5652 in a closed position. In a closed position, the anvil 5652 can compress tissue 5658 against the staple cartridge 5656. The conductors 5672 embedded within the tissue compensator 5660 can be operable to apply pulses of electrical current 5674, at predetermined frequencies, to the tissue 5658. The same or additional conductors 5672 can detect the response of the tissue 5658 and transmit this response to a microprocessor or microcontroller located in the instrument. The response of the tissue 5658 to the electrical pulses 5674 can be used to determine a property of the tissue 5658. For example, the galvanic response of the tissue 5658 indicates the moisture content in the tissue 5658. As another example, measurement of the electrical impedance through the tissue 5658 could be used to determine the conductivity of the tissue 5648, which is an indicator of the tissue type. Other properties that can be determined include by way of example and not limitation: oxygen content, salinity, density, and/or the presence of certain chemicals. By combining data from several sensors, other properties could be determined, such as blood flow, blood type, the presence of antibodies, etc. The conductors 5662 may be employed to measure tissue thickness, force, displacement, compression, tissue impedance, and tissue location within the end effector 5650.

Figure 16:
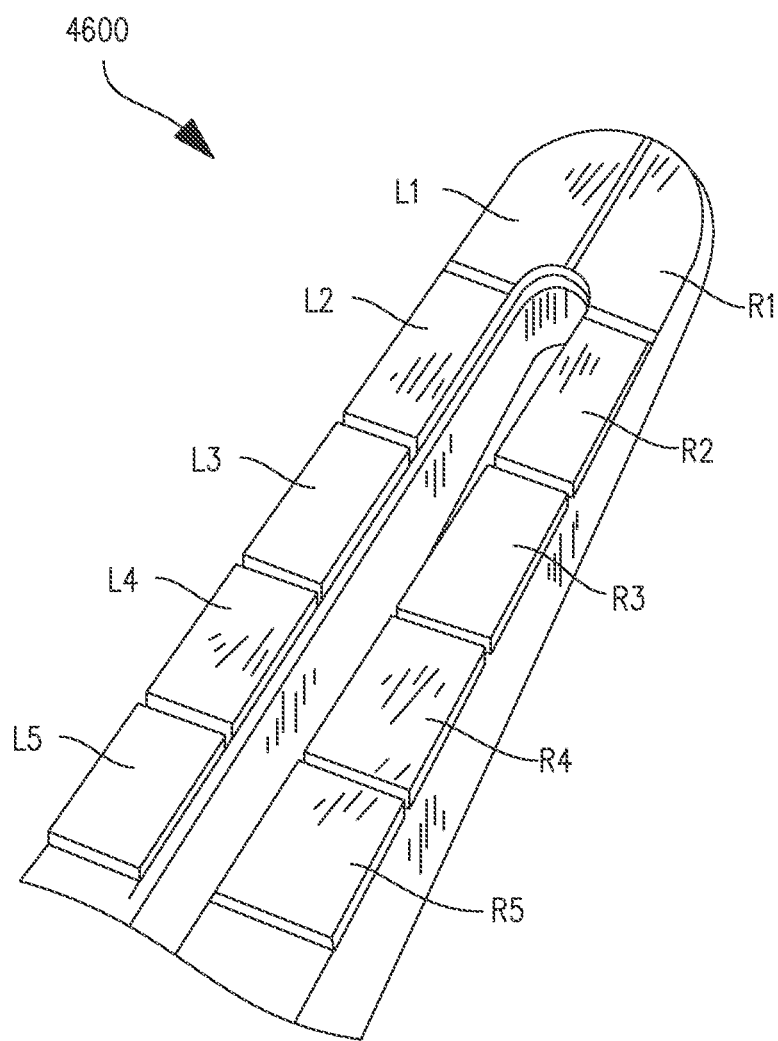
FIG. 16 illustrates one aspect of a left-right segmented flexible circuit for an end effector according to one aspect of this disclosure.

FIG. 16 illustrates one aspect of a left-right segmented flexible circuit 4600. The left-right segmented flexible circuit 4600 comprises a plurality of segments L1-L5 on the left side of the left-right segmented flexible circuit 4600 and a plurality of segments R1-R5 on the right side of the left-right segmented flexible circuit 4600. Each of the segments L1-L5 and R1-R5 comprise temperature sensors and/or force sensors to sense tissue parameters locally within each segment L1-L5 and R1-R5. The left-right segmented flexible circuit 4600 is configured to sense tissue parameters locally within each of the segments L1-L5 and R1-R5. The flexible circuit 4600 may be employed to measure tissue thickness, force, displacement, compression, tissue impedance, and tissue location within an end effector.

Figure 17:
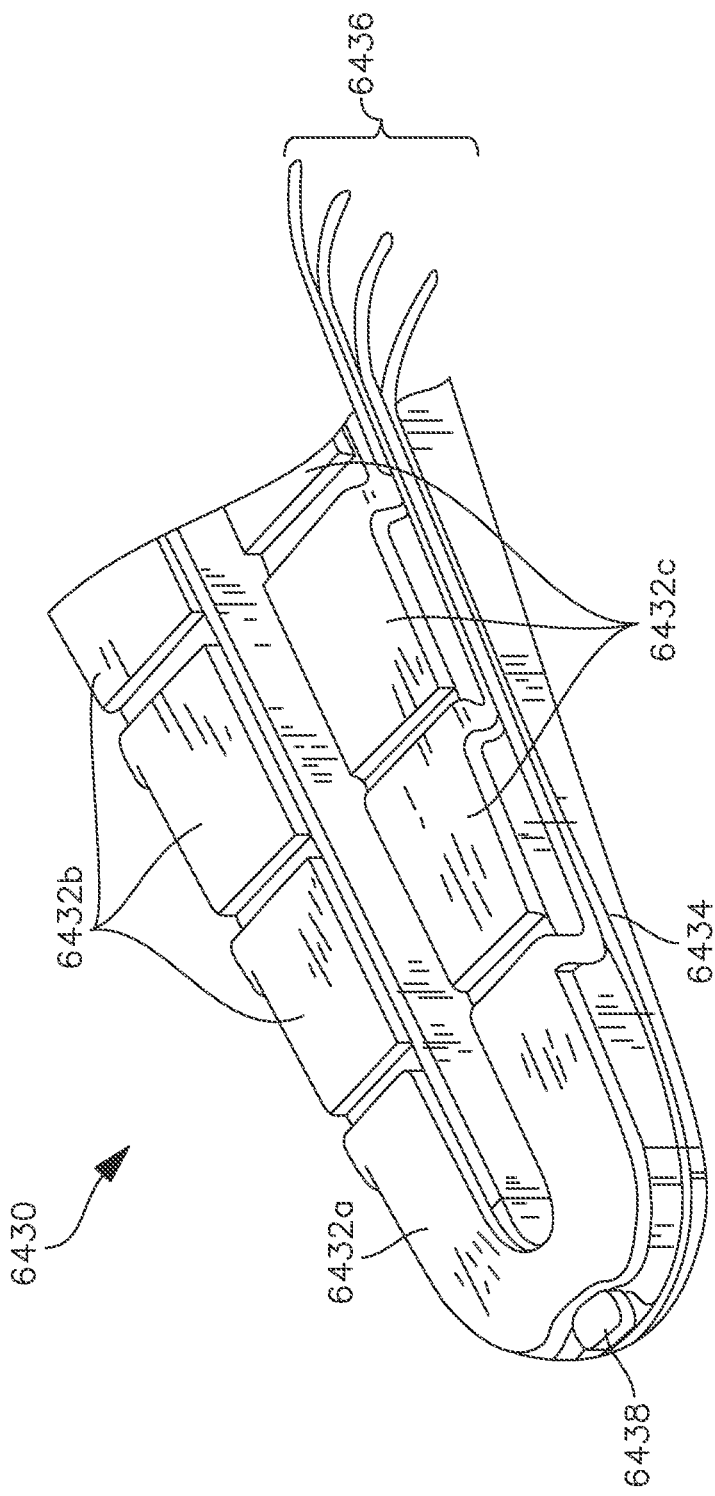
FIG. 17 illustrates one aspect of a segmented flexible circuit configured to fixedly attach to a jaw member of an end effector according to one aspect of this disclosure.

FIG. 17 illustrates one aspect of a segmented flexible circuit 6430 configured to fixedly attach to a jaw member 6434 of an end effector. The segmented flexible circuit 6430 comprises a distal segment 6432*a* and lateral segments 6432*b*, 6432*c* that include individually addressable sensors to provide local tissue presence detection. The segments 6432*a*, 6432*b*, 6432*c* are individually addressable to detect tissue and to measure tissue parameters based on individual sensors located within each of the segments 6432*a*, 6432*b*, 6432*c*. The segments 6432*a*, 6432*b*, 6432*c* of the segmented flexible circuit 6430 are mounted to the jaw member 6434 and are electrically coupled to an energy source such as an electrical circuit via electrical conductive elements 6436. A Hall effect sensor 6438, or any suitable magnetic sensor, is located on a distal end of the jaw member 6434. The Hall effect sensor 6438 operates in conjunction with a magnet to provide a measurement of an aperture defined by the jaw member 6434, which otherwise may be referred to as a tissue gap, as shown with particularity in FIG. 19. The segmented flexible circuit 6430 may be employed to measure tissue thickness, force, displacement, compression, tissue impedance, and tissue location within an end effector.

Figure 18:
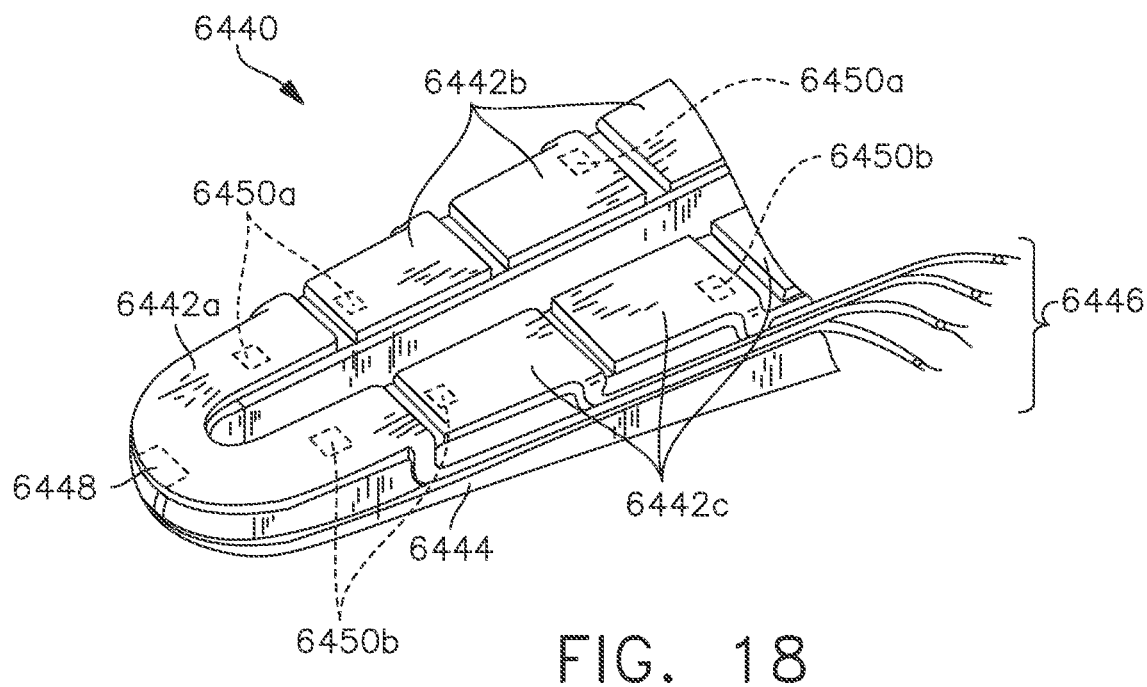
FIG. 18 illustrates one aspect of a segmented flexible circuit configured to mount to a jaw member of an end effector according to one aspect of this disclosure.

FIG. 18 illustrates one aspect of a segmented flexible circuit 6440 configured to mount to a jaw member 6444 of an end effector. The segmented flexible circuit 6580 comprises a distal segment 6442*a* and lateral segments 6442*b*, 6442*c* that include individually addressable sensors for tissue control. The segments 6442*a*, 6442*b*, 6442*c* are individually addressable to treat tissue and to read individual sensors located within each of the segments 6442*a*, 6442*b*, 6442*c*. The segments 6442*a*, 6442*b*, 6442*c* of the segmented flexible circuit 6440 are mounted to the jaw member 6444 and are electrically coupled to an energy source, via electrical conductive elements 6446. A Hall effect sensor 6448, or other suitable magnetic sensor, is provided on a distal end of the jaw member 6444. The Hall effect sensor 6448 operates in conjunction with a magnet to provide a measurement of an aperture defined by the jaw member 6444 of the end effector or tissue gap as shown with particularity in FIG. 19. In addition, a plurality of lateral asymmetric temperature sensors 6450*a*, 6450*b* are mounted on or formally integrally with the segmented flexible circuit 6440 to provide tissue temperature feedback to the control circuit. The segmented flexible circuit 6440 may be employed to measure tissue thickness, force, displacement, compression, tissue impedance, and tissue location within an end effector.

Figure 19:
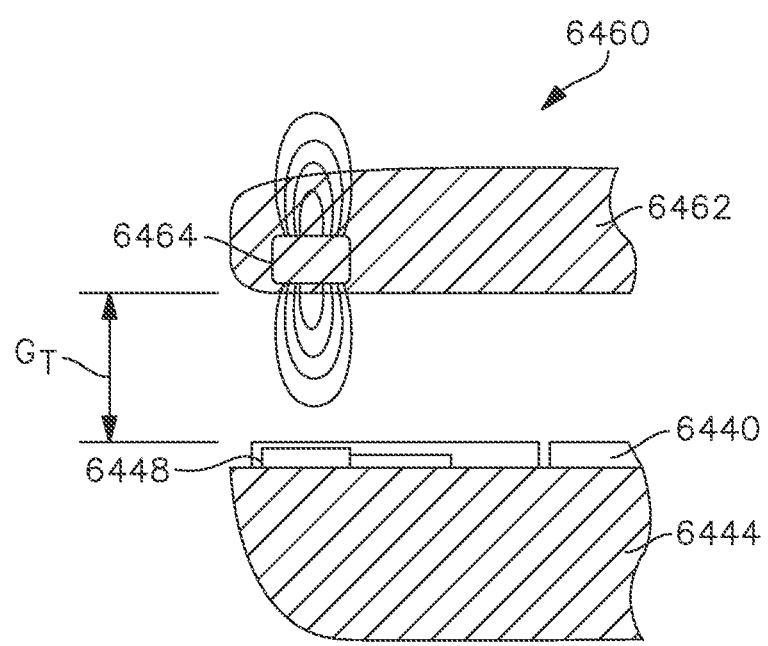
FIG. 19 illustrates one aspect of an end effector configured to measure a tissue gap GT according to one aspect of this disclosure.

FIG. 19 illustrates one aspect of an end effector 6460 configured to measure a tissue gap $G_T$. The end effector 6460 comprises a jaw member 6462 and a jaw member 6444. The flexible circuit 6440 as described in FIG. 18 is mounted to the jaw member 6444. The flexible circuit 6440 comprises a Hall effect sensor 6448 that operates with a magnet 6464 mounted to the jaw member 6462 to measure the tissue gap $G_T$. This technique can be employed to measure the aperture defined between the jaw member 6444 and the jaw member 6462. The jaw member 6462 may be a staple cartridge.

Figure 20:
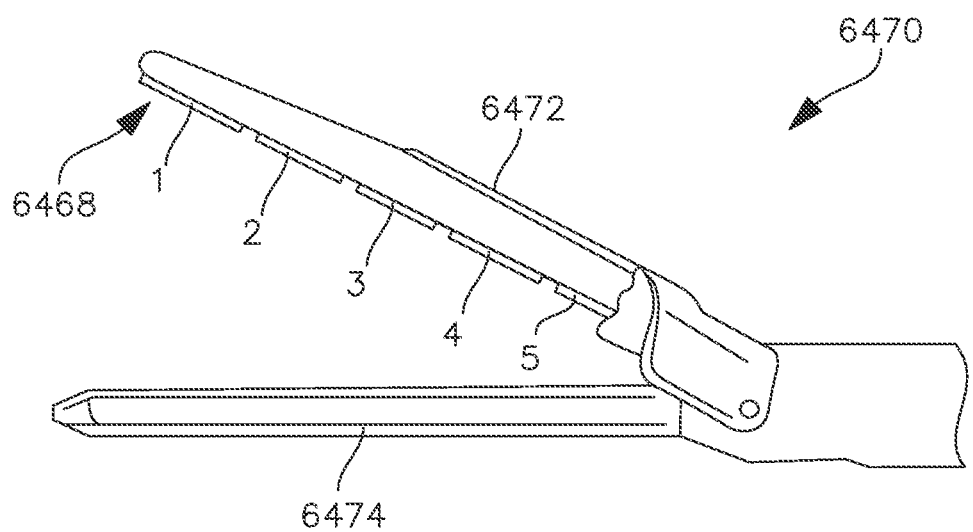
FIG. 20 illustrates one aspect of an end effector comprising segmented flexible circuit, according to one aspect of this present disclosure.

FIG. 20 illustrates one aspect of an end effector 6470 comprising segmented flexible circuit 6468 as shown in FIG. 16. The end effector 6470 comprises a jaw member 6472 and a staple cartridge 6474. The segmented flexible circuit 6468 is mounted to the jaw member 6472. Each of the sensors disposed within the segments 1-5 are configured to detect the presence of tissue positioned between the jaw member 6472 and the staple cartridge 6474 and represent tissue zones 1-5. In the configuration shown in FIG. 20, the end effector 6470 is shown in an open position ready to receive or grasp tissue between the jaw member 6472 and the staple cartridge 6474. The segmented flexible circuit 6468 may be employed to measure tissue thickness, force, displacement, compression, tissue impedance, and tissue location within the end effector 6470.

Figure 21:
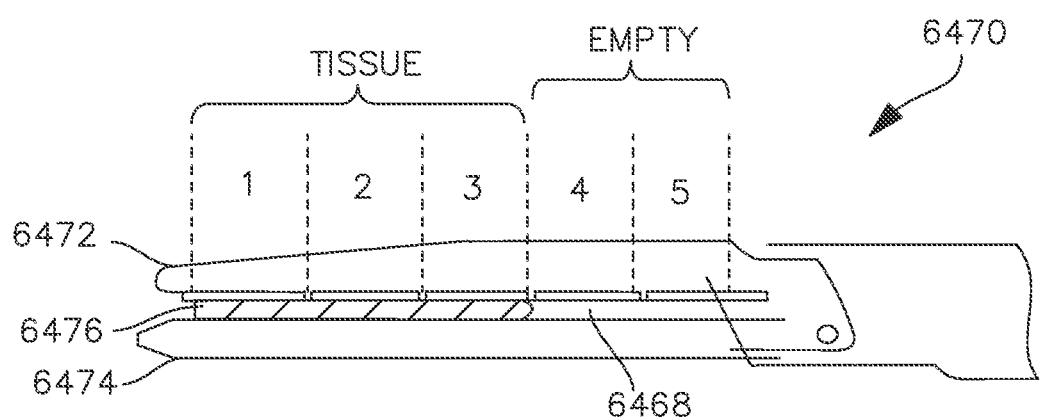
FIG. 21 illustrates the end effector shown in FIG. 20 with the jaw member clamping tissue between the jaw member and the staple cartridge according to one aspect of this disclosure.

FIG. 21 illustrates the end effector 6470 shown in FIG. 20 with the jaw member 6472 clamping tissue 6476 between the jaw members 6472, e.g., the anvil and the staple cartridge. As shown in FIG. 21, the tissue 6476 is positioned between segments 1-3 and represents tissue zones 1-3. Accordingly, tissue 6476 is detected by the sensors in segments 1-3 and the absence of tissue (empty) is detected in section 6478 by segments 4-5. The information regarding the presence and absence of tissue 6476 positioned within certain segments 1-3 and 4-5, respectively, is communicated to a control circuit as described herein via interface circuits, for example. The control circuit is configured to detect tissue located in segments 1-3. It will be appreciated that the segments 1-5 may contain any suitable temperature, force/pressure, and/or Hall effect magnetic sensors to measure tissue parameters of tissue located within certain segments 1-5 and electrodes to deliver energy to tissue located in certain segments 1-5. The segmented flexible circuit 6468 may be employed to measure tissue thickness, force, displacement, compression, tissue impedance, and tissue location within the end effector 6470.

Figure 22:
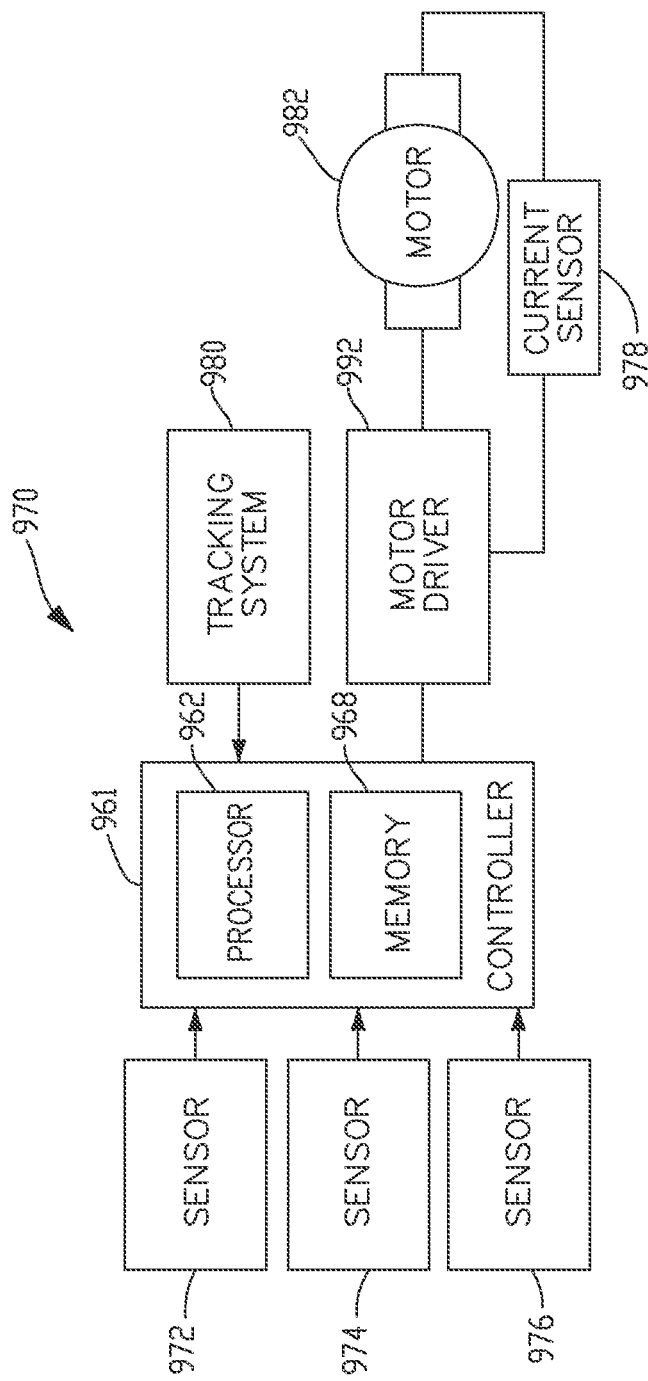
FIG. 22 illustrates a logic diagram of one aspect of a feedback system according to one aspect of this disclosure.

FIG. 22 illustrates a logic diagram of a feedback system 970 of the robotic surgical system 10 of FIG. 1 in accordance with one or more aspects of the present disclosure. The system 970 comprises a circuit. The circuit includes a controller 961 comprising a processor 962 and a memory 968. One or more of sensors 972, 974, 976, such as, for example, provide real time feedback to the processor 962. A motor 982 driven by a motor driver 992 operably couples a longitudinally movable displacement member to drive the I-beam knife element. A tracking system 980 is configured to determine the position of the longitudinally movable displacement member. The position information is provided to the processor 962, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation.

In one form, a strain gauge can be used to measure the force applied to the tissue by the end effector. A strain gauge can be coupled to the end effector to measure the force on the tissue being treated by the end effector. With reference now to FIG. 22, a system 970 for measuring forces applied to the tissue grasped by the end effector comprises a strain gauge sensor 972, such as, for example, a micro-strain gauge, is configured to measure one or more parameters of the end effector, for example. In one aspect, the strain gauge sensor 972 can measure the amplitude or magnitude of the strain exerted on a jaw member of an end effector during a clamping operation, which can be indicative of the tissue compression. The measured strain is converted to a digital signal and provided to a processor 962 of a microcontroller 961. A load sensor 974 can measure the force to operate the knife element, for example, to cut the tissue captured between the anvil and the staple cartridge. A magnetic field sensor 976 can be employed to measure the thickness of the captured tissue. The measurement of the magnetic field sensor 976 also may be converted to a digital signal and provided to the processor 962.

The measurements of the tissue compression, the tissue thickness, and/or the force required to close the end effector on the tissue, as respectively measured by the sensors 972, 974, 976, can be used by the microcontroller 961 to characterize the selected position of the firing member and/or the corresponding value of the speed of the firing member. In one instance, a memory 968 may store a technique, an equation, and/or a look-up table which can be employed by the microcontroller 961 in the assessment.

In the aspect illustrated in FIG. 22, a sensor 972, such as, for example, a strain gauge or a micro-strain gauge, is configured to measure one or more parameters of the end effector 912, such as, for example, the amplitude of the strain exerted on the anvil 914 during a clamping operation, which can be indicative of the closure forces applied to the anvil 914. The measured strain is converted to a digital signal and provided to the processor 962. Alternatively, or in addition to the sensor 972, a sensor 974, such as, for example, a load sensor, can measure the closure force applied by the closure drive system to the anvil 914. The sensor 976, such as, for example, a load sensor, can measure the firing force applied to an I-beam in a firing stroke of the robotic surgical system 10 (FIG. 1). The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 978 can be employed to measure the current drawn by the motor 982. The force required to advance the firing member 220 can correspond to the current drawn by the motor 982, for example. The measured force is converted to a digital signal and provided to the processor 962.

Figure 23:
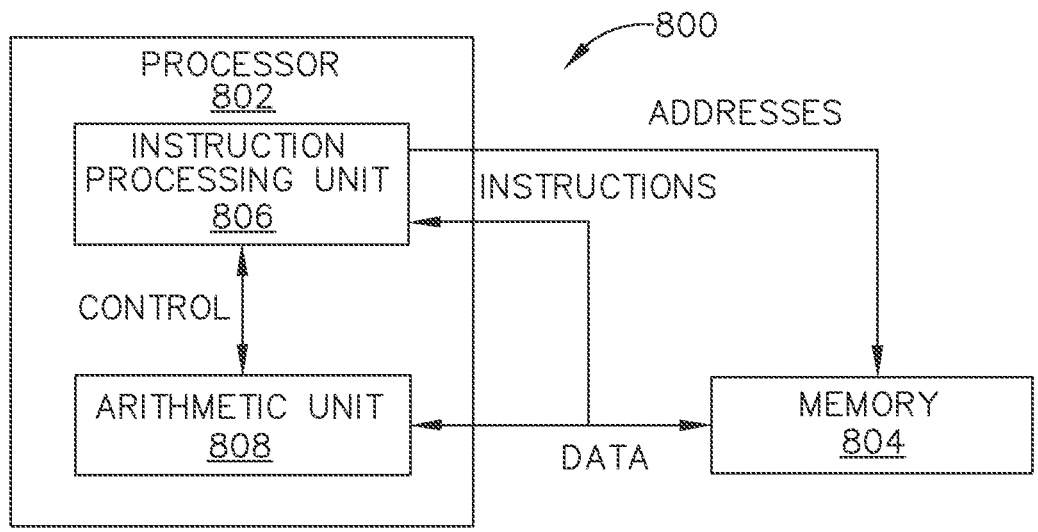
FIG. 23 illustrates a control circuit configured to control aspects of the robotic surgical system according to one aspect of this disclosure.

FIG. 23 illustrates a control circuit configured to control aspects of the robotic surgical system 10 according to one aspect of this disclosure. FIG. 23 illustrates a control circuit 800 configured to control aspects of the robotic surgical system 10 according to one aspect of this disclosure. The control circuit 800 can be configured to implement various processes described herein. The control circuit 800 may comprise a controller comprising one or more processors 802 (e.g., microprocessor, microcontroller) coupled to at least one memory circuit 804. The memory circuit 804 stores machine executable instructions that when executed by the processor 802, cause the processor 802 to execute machine instructions to implement various processes described herein. The processor 802 may be any one of a number of single or multicore processors known in the art. The memory circuit 804 may comprise volatile and non-volatile storage media. The processor 802 may include an instruction processing unit 806 and an arithmetic unit 808. The instruction processing unit may be configured to receive instructions from the memory circuit 804 of this disclosure.

Figure 24:
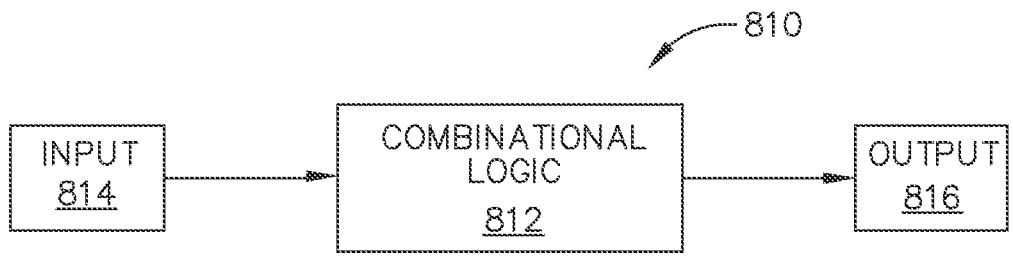
FIG. 24 illustrates a combinational logic circuit configured to control aspects of the robotic surgical system according to one aspect of this disclosure.

FIG. 24 illustrates a combinational logic circuit 810 configured to control aspects of the robotic surgical system 10 according to one aspect of this disclosure. The combinational logic circuit 810 can be configured to implement various processes described herein. The circuit 810 may comprise a finite state machine comprising a combinational logic circuit 812 configured to receive data associated with the robotic surgical system 10 at an input 814, process the data by the combinational logic 812, and provide an output 816.

Figure 25:
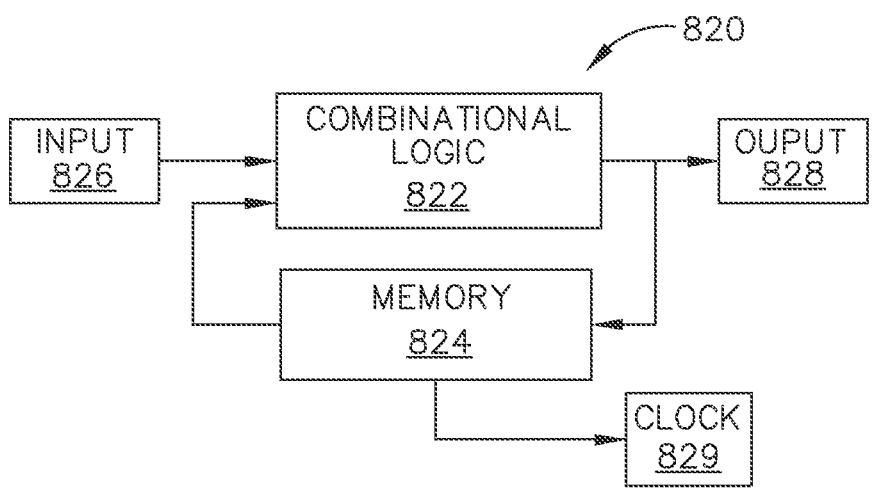
FIG. 25 illustrates a sequential logic circuit configured to control aspects of the robotic surgical system according to one aspect of this disclosure.

FIG. 25 illustrates a sequential logic circuit 820 configured to control aspects of the robotic surgical system 10 according to one aspect of this disclosure. The sequential logic circuit 820 or the combinational logic circuit 822 can be configured to implement various processes described herein. The circuit 820 may comprise a finite state machine. The sequential logic circuit 820 may comprise a combinational logic circuit 822, at least one memory circuit 824, and a clock 829, for example. The at least one memory circuit 820 can store a current state of the finite state machine. In certain instances, the sequential logic circuit 820 may be synchronous or asynchronous. The combinational logic circuit 822 is configured to receive data associated with the robotic surgical system 10 an input 826, process the data by the combinational logic circuit 822, and provide an output 828. In other aspects, the circuit may comprise a combination of the processor 802 and the finite state machine to implement various processes herein. In other aspects, the finite state machine may comprise a combination of the combinational logic circuit 810 and the sequential logic circuit 820.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor.

Figure 26:
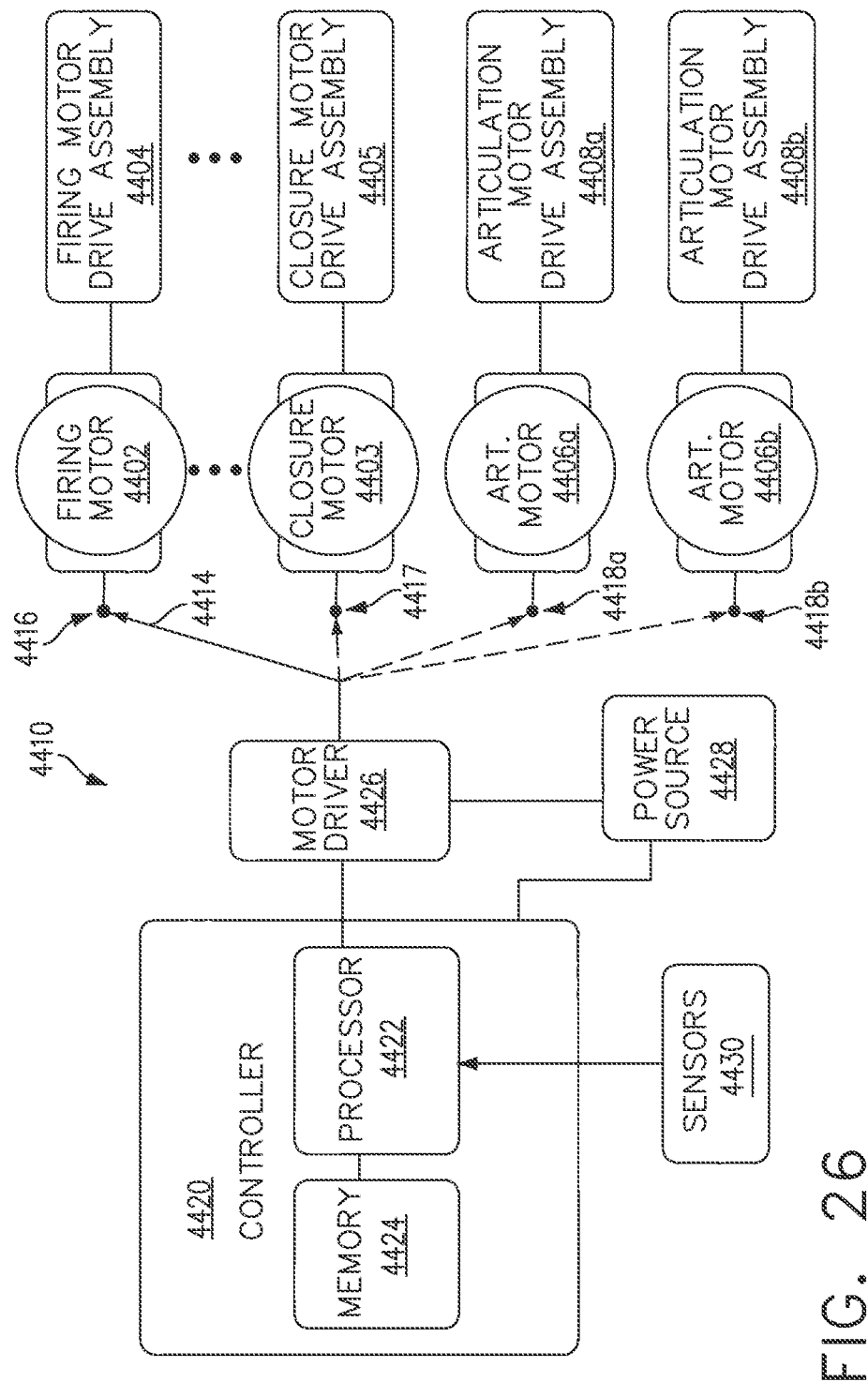
FIG. 26 illustrates a logic diagram of a common control module for use with a plurality of motors of the robotic surgical instrument according to one aspect of this disclosure.

Referring primarily to FIG. 26 a robotic surgical system 10 may include a plurality of motors which can be activated to perform various functions. In certain instances, a first motor can be activated to perform a first function; a second motor can be activated to perform a second function; a third motor can be activated to perform a third function, a fourth motor can be activated to perform a fourth function, and so on. In certain instances, the plurality of motors of the robotic surgical instrument 4400 can be individually activated to cause firing, closure and/or articulation motions in the end effector 1012. The firing, closure and/or articulation motions can be transmitted to the end effector 1012 through the shaft assembly 200, for example.

In certain instances, the robotic surgical system 10 may include a firing motor 4402. The firing motor 4402 may be operably coupled to a firing drive assembly 4404 which can be configured to transmit firing motions generated by the motor 4402 to the end effector 1012, and in particular to displace the I-beam element. In certain instances, the firing motions generated by the motor 4402 may cause the staples to be deployed from the staple cartridge into tissue captured by the end effector and/or the cutting edge of the I-beam element to be advanced to cut the captured tissue, for example. The I-beam element may be retracted by reversing the direction of the motor 4402.

In certain instances, the robotic surgical system 10 may include a closure motor 4403. The closure motor 4403 may be operably coupled to a closure drive assembly 4405 which can be configured to transmit closure motions generated by the motor 4403 to the end effector 1012, and in particular to displace the closure tube 1040, 1042 to close the anvil 1024 and compress tissue between the anvil 1024 and the staple cartridge 1034. The closure motions may cause the end effector 1012 to transition from an open configuration to an approximated configuration to capture tissue, for example. The end effector 102 may be transitioned to an open position by reversing the direction of the motor 4403.

In certain instances, the robotic surgical instrument 10 may include one or more articulation motors 4406a, 4406b, for example. The motors 4406a, 4406b may be operably coupled to respective articulation drive assemblies 4408a, 4408b, which can be configured to transmit articulation motions generated by the motors 4406a, 4406b to the end effector 1012. In certain instances, the articulation motions may cause the end effector to articulate relative to the shaft, for example.

As described above, the robotic surgical instrument 10 may include a plurality of motors which may be configured to perform various independent functions. In certain instances, the plurality of motors of the robotic surgical instrument 10 can be individually or separately activated to perform one or more functions while the other motors remain inactive. For example, the articulation motors 4406a, 4406b can be activated to cause the end effector to be articulated while the firing motor 4402 remains inactive. Alternatively, the firing motor 4402 can be activated to fire the plurality of staples and/or advance the cutting edge while the articulation motor 4406 remains inactive. Furthermore the closure motor 4403 may be activated simultaneously with the firing motor 4402 to cause the closure tube 1040, 1042 and the I-beam element to advance distally as described in more detail hereinbelow.

In certain instances, the robotic surgical system 10 may include a common control module 4410 which can be employed with a plurality of motors of the robotic surgical instrument 10. In certain instances, the common control module 4410 may accommodate one of the plurality of motors at a time. For example, the common control module 4410 can be separably couplable to the plurality of motors of the robotic surgical instrument 10 individually. In certain instances, a plurality of the motors of the robotic surgical instrument 10 may share one or more common control modules such as the module 4410. In certain instances, a plurality of motors of the robotic surgical instrument 10 can be individually and selectively engaged the common control module 4410. In certain instances, the module 4410 can be selectively switched from interfacing with one of a plurality of motors of the robotic surgical instrument 10 to interfacing with another one of the plurality of motors of the robotic surgical instrument 10.

In at least one example, the module 4410 can be selectively switched between operable engagement with the articulation motors 4406a, 4406b and operable engagement with either the firing motor 4402 or the closure motor 4403. In at least one example, as illustrated in FIG. 26, a switch 4414 can be moved or transitioned between a plurality of positions and/or states. In a first position 4416 the switch 4414 may electrically couple the module 4410 to the firing motor 4402; in a second position 4417, the switch 4414 may electrically couple the module 4410 to the closure motor 4403; in a third position 4418a the switch 4414 may electrically couple the module 4410 to the first articulation motor 4406a; and in a fourth position 4418b the switch 4414 may electrically couple the module 4410 to the second articulation motor 4406b, for example. In certain instances, separate modules 4410 can be electrically coupled to the firing motor 4402, the closure motor 4403, and the articulations motor 4406a, 4406b at the same time, as shown, for example in FIG. 30. In certain instances, the switch 4414 may be a mechanical switch, an electromechanical switch, a solid state switch, or any suitable switching mechanism.

Each of the motors 4402, 4403, 4406a, 4406b may comprise a torque sensor to measure the output torque on the shaft of the motor. The force on an end effector may be sensed in any conventional manner such as by force sensors on the outer sides of the jaws or by a torque sensor for the motor actuating the jaws.

In various instances, as illustrated in FIG. 26, the common control module 4410 may comprise a motor driver 4426 which may comprise one or more H-Bridge field-effect transistors (FETs). The motor driver 4426 may modulate the power transmitted from a power source 4428 to a motor coupled to the module 4410 based on input from a microcontroller 4420 ("controller"), for example. In certain instances, the controller 4420 can be employed to determine the current drawn by the motor, for example, while the motor is coupled to the module 4410, as described above.

In certain instances, the controller 4420 may include a microprocessor 4422 ("processor") and one or more computer readable mediums or memory units 4424 ("memory"). In certain instances, the memory 4424 may store various program instructions, which when executed may cause the processor 4422 to perform a plurality of functions and/or calculations described herein. In certain instances, one or more of the memory units 4424 may be coupled to the processor 4422, for example.

In certain instances, the power source 4428 can be employed to supply power to the controller 4420, for example. In certain instances, the power source 4428 may comprise a battery (or "battery pack" or "power pack"), such as a Li ion battery, for example. In certain instances, the battery pack may be configured to be releasably mounted to the handle 14 for supplying power to the surgical instrument 4400. A number of battery cells connected in series may be used as the power source 4428. In certain instances, the power source 4428 may be replaceable and/or rechargeable, for example.

In various instances, the processor 4422 may control the motor driver 4426 to control the position, direction of rotation, and/or velocity of a motor that is coupled to the module 4410. In certain instances, the processor 4422 can signal the motor driver 4426 to stop and/or disable a motor that is coupled to the module 4410. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 4422 may be any single core or multicore processor such as those known under the trade name ARM Cortex by Texas Instruments. In certain instances, the microcontroller 4420 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, one or more 12-bit ADC with 12 analog input channels, among other features that are readily available for the product datasheet. Other microcontrollers may be readily substituted for use with the module 4410. Accordingly, the present disclosure should not be limited in this context.

In certain instances, the memory 4424 may include program instructions for controlling each of the motors of the surgical instrument 4400 that are couplable to the module 4410. For example, the memory 4424 may include program instructions for controlling the firing motor 4402, the closure motor 4403, and the articulation motors 4406a, 4406b. Such program instructions may cause the processor 4422 to control the firing, closure, and articulation functions in accordance with inputs from algorithms or control programs of the robotic surgical system 10.

In certain instances, one or more mechanisms and/or sensors such as, for example, sensors 4430 can be employed to alert the processor 4422 to the program instructions that should be used in a particular setting. For example, the sensors 4430 may alert the processor 4422 to use the program instructions associated with firing, closing, and articulating the end effector 1012. In certain instances, the sensors 4430 may comprise position sensors which can be employed to sense the position of the switch 4414, for example. Accordingly, the processor 4422 may use the program instructions associated with firing the I-beam of the end effector 1012 upon detecting, through the sensors 4430 for example, that the switch 4414 is in the first position 4416; the processor 4422 may use the program instructions associated with closing the anvil upon detecting, through the sensors 4430 for example, that the switch 4414 is in the second position 4417; and the processor 4422 may use the program instructions associated with articulating the end effector 1012 upon detecting, through the sensors 4430 for example, that the switch 4418a, 4418b is in the third or fourth position 4418a, 4418b.

Figure 27:
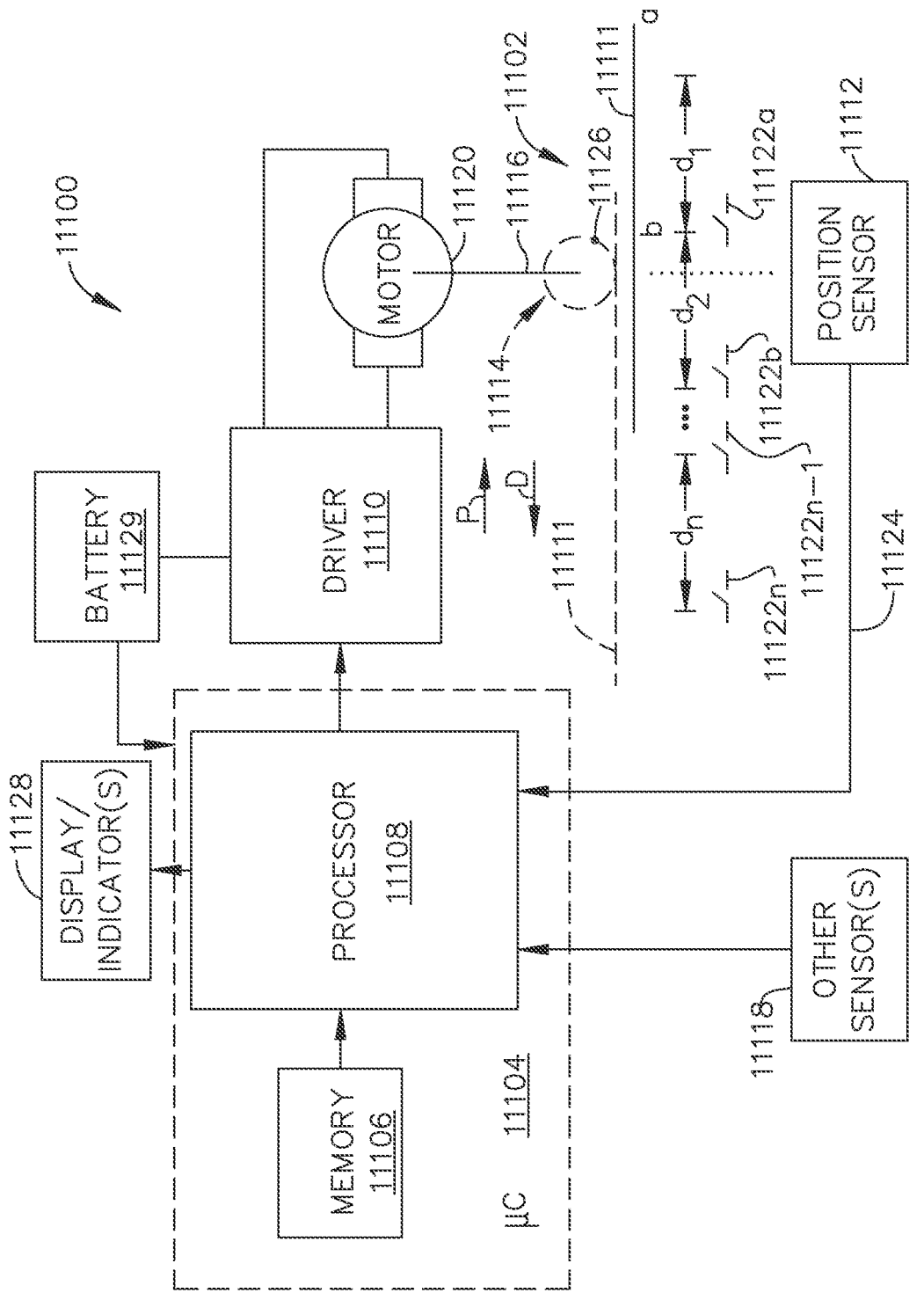
FIG. 27 is a diagram of an absolute positioning system of the surgical instrument of FIG. 1 where the absolute positioning system comprises a controlled motor drive circuit arrangement comprising a sensor arrangement according to one aspect of this disclosure.

FIG. 27 is a diagram of an absolute positioning system 11100 of the robotic surgical instrument 10 where the absolute positioning system 11100 comprises a controlled motor drive circuit arrangement comprising a sensor arrangement 11102 according to one aspect of this disclosure. The sensor arrangement 11102 for an absolute positioning system 11100 provides a unique position signal corresponding to the location of a displacement member 11111. In one aspect the displacement member 11111 represents the longitudinally movable drive member coupled to the cutting instrument or knife (e.g., cutting instrument 1032 in FIG. 11A, I-beam 3005 in FIG. 12, and/or I-beam 2514 in FIGS. 29-30) comprising the first knife driven gear 1226 in meshing engagement with the knife spur gear 1222, the second knife drive gear 1228 in meshing engagement with a third knife drive gear 1230 that is rotatably supported on the tool mounting plate 302 in meshing engagement with the knife rack gear 1206. In other aspects, the displacement member 11111 represents a firing member coupled to the cutting instrument or knife, which could be adapted and configured to include a rack of drive teeth. In yet another aspect, the displacement member 11111 represents a firing bar or the I-beam 3005, 2514 (FIGS. 12, 30), each of which can be adapted and configured to include a rack of drive teeth. Accordingly, as used herein, the term displacement member is used generically to refer to any movable member of the robotic surgical instrument 10 such as a drive member, firing member, firing bar, cutting instrument, knife, and/or I-beam, or any element that can be displaced.

Accordingly, the absolute positioning system 11100 can, in effect, track the displacement of the cutting instrument I-beam 3005, 2514 (FIGS. 12, 29-30) by tracking the displacement of a longitudinally movable drive member. In various other aspects, the displacement member 11111 may be coupled to any sensor suitable for measuring displacement. Thus, a longitudinally movable drive member, firing member, the firing bar, or !-beam, or combinations thereof, may be coupled to any suitable displacement sensor. Displacement sensors may include contact or non-contact displacement sensors. Displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

An electric motor 11120 can include a rotatable shaft 11116 that operably interfaces with a gear assembly 11114 that is mounted in meshing engagement with a set, or rack, of drive teeth on the displacement member 11111. A sensor element 11126 may be operably coupled to a gear assembly 11114 such that a single revolution of the sensor element 11126 corresponds to some linear longitudinal translation of the displacement member 11111. An arrangement of gearing and sensors 11118 can be connected to the linear actuator via a rack and pinion arrangement or a rotary actuator via a spur gear or other connection. A power source 11129 supplies power to the absolute positioning system 11100 and an output indicator 11128 may display the output of the absolute positioning system 11100. The interface for adapting to the motor 11120 is shown in FIGS. 4-6, 8-10, and 11A, 11B.

A single revolution of the sensor element 11126 associated with the position sensor 11112 is equivalent to a longitudinal displacement d1 of the of the displacement member 11111, where d1 is the longitudinal distance that the displacement member 11111 moves from point "a" to point "b" after a single revolution of the sensor element 11126 coupled to the displacement member 11111. The sensor arrangement 11102 may be connected via a gear reduction that results in the position sensor 11112 completing one or more revolutions for the full stroke of the displacement member 11111. The position sensor 11112 may complete multiple revolutions for the full stroke of the displacement member 11111.

A series of switches 11122a-11122n, where n is an integer greater than one, may be employed alone or in combination with gear reduction to provide a unique position signal for more than one revolution of the position sensor 11112. The state of the switches 11122a-11122n are fed back to a controller 11104 that applies logic to determine a unique position signal corresponding to the longitudinal displacement d1+d2+ . . . dn of the displacement member 11111. The output 11124 of the position sensor 11112 is provided to the controller 11104. The position sensor 11112 of the sensor arrangement 11102 may comprise a magnetic sensor, an analog rotary sensor like a potentiometer, an array of analog Hall-effect elements, which output a unique combination of position signals or values. The controller 11104 may be contained within the master controller 11 or may be contained within the tool mounting portion housing 301.

The absolute positioning system 11100 provides an absolute position of the displacement member 11111 upon power up of the robotic surgical instrument 10 without retracting or advancing the displacement member 11111 to a reset (zero or home) position as may be required with conventional rotary encoders that merely count the number of steps forwards or backwards that the motor 11120 has taken to infer the position of a device actuator, drive bar, knife, and the like.

The controller 11104 may be programmed to perform various functions such as precise control over the speed and position of the knife and articulation systems. In one aspect, the controller 11104 includes a processor 11108 and a memory 11106. The electric motor 11120 may be a brushed DC motor with a gearbox and mechanical links to an articulation or knife system. In one aspect, a motor driver 11110 may be an A3941 available from Allegro Microsystems, Inc. Other motor drivers may be readily substituted for use in the absolute positioning system 11100.

The controller 11104 may be programmed to provide precise control over the speed and position of the displacement member 11111 and articulation systems. The controller 11104 may be configured to compute a response in the software of the controller 11104. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The absolute positioning system 11100 may comprise and/or be programmed to implement a feedback controller, such as a PID, state feedback, and adaptive controller. A power source 11129 converts the signal from the feedback controller into a physical input to the system, in this case voltage. Other examples include pulse width modulation (PWM) of the voltage, current, and force. Other sensor(s) 11118 may be provided to measure physical parameters of the physical system in addition to position measured by the position sensor 11112. In a digital signal processing system, absolute positioning system 1100 is coupled to a digital data acquisition system where the output of the absolute positioning system 11100 will have finite resolution and sampling frequency. The absolute positioning system 11100 may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The motor driver 11110 may be an A3941 available from Allegro Microsystems, Inc. The A3941 driver 11110 is a full-bridge controller for use with external N-channel power metal oxide semiconductor field effect transistors (MOSFETs) specifically designed for inductive loads, such as brush DC motors. The driver 11110 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 11100.

Figure 28:
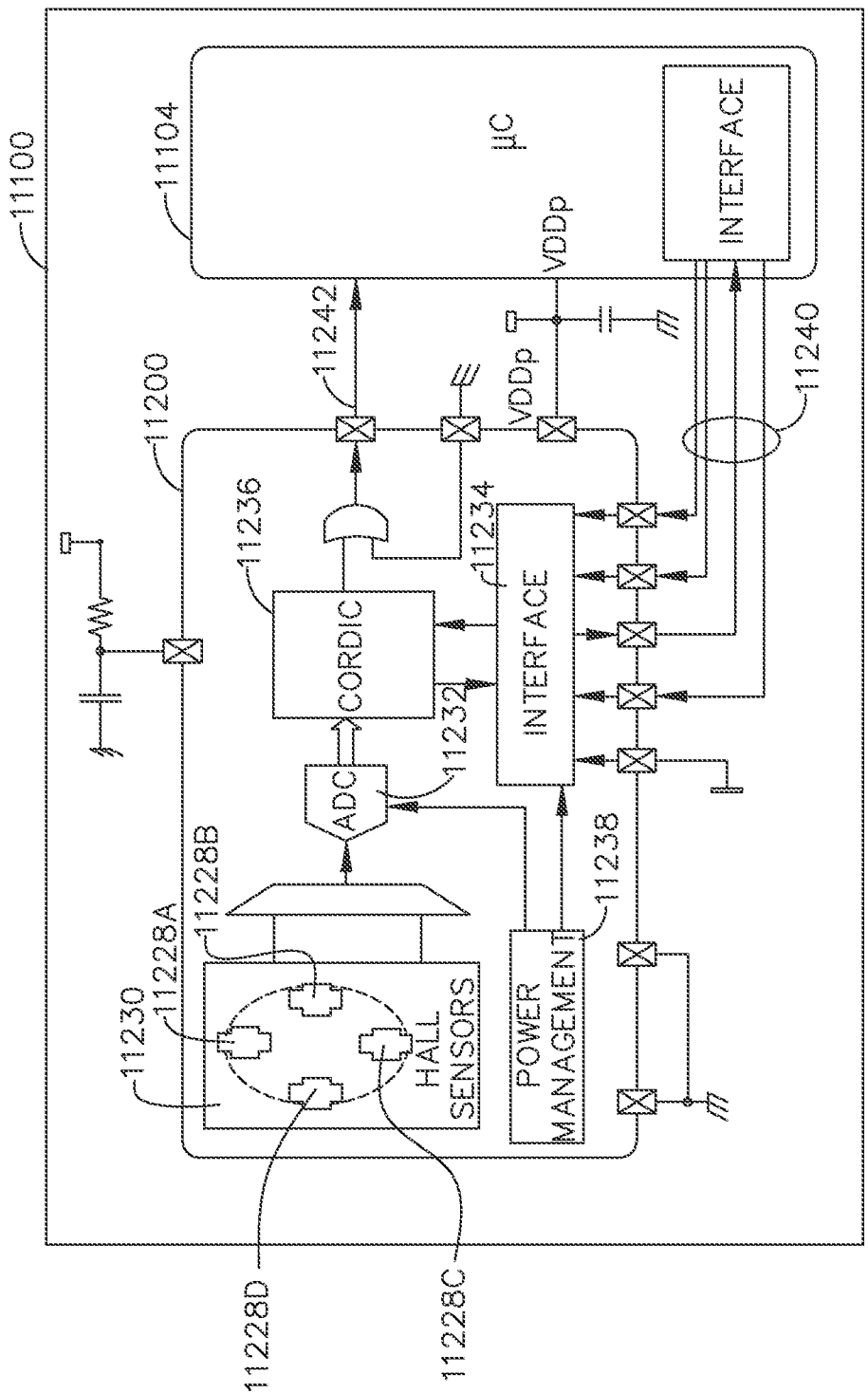
FIG. 28 is a diagram of a position sensor comprising a magnetic rotary absolute positioning system according to one aspect of this disclosure.

FIG. 28 is a diagram of a position sensor 11200 for an absolute positioning system 11100 comprising a magnetic rotary absolute positioning system according to one aspect of this disclosure. The position sensor 11200 may be implemented as an AS5055EQFT single-chip magnetic rotary position sensor available from Austria Microsystems, AG. The position sensor 11200 is interfaced with the controller 11104 to provide an absolute positioning system 11100. The position sensor 11200 is a low-voltage and low-power component and includes four Hall-effect elements 11228A, 11228B, 11228C, 11228D in an area 11230 of the position sensor 11200 that is located above a magnet 11202 positioned on a rotating element associated with a displacement member such as, for example, the knife drive gear 1228, 1230 and/or the closure drive gear 1118, 1120 such that the displacement of a firing member and/or a closure member can be precisely tracked. A high-resolution ADC 11232 and a smart power management controller 11238 are also provided on the chip. A CORDIC processor 11236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 11234 to the controller 11104. The position sensor 11200 provides 12 or 14 bits of resolution. The position sensor 11200 may be an AS5055 chip provided in a small QFN 16-pin 4×4×0.85 mm package.

The Hall-effect elements 11228A, 11228B, 11228C, 11228D are located directly above the rotating magnet 11202. The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 11200, the Hall-effect elements 11228A, 11228B, 11228C, 11228D are capable producing a voltage signal that is indicative of the absolute position of the magnet 11202 in terms of the angle over a single revolution of the magnet 11202. This value of the angle, which is unique position signal, is calculated by the CORDIC processor 11236 is stored onboard the AS5055 position sensor 11200 in a register or memory. The value of the angle that is indicative of the position of the magnet 11202 over one revolution is provided to the controller 11104 in a variety of techniques, e.g., upon power up or upon request by the controller 11104.

The AS5055 position sensor 11200 requires only a few external components to operate when connected to the controller 11104. Six wires are needed for a simple application using a single power supply: two wires for power and four wires 11240 for the SPI interface 11234 with the controller 11104. A seventh connection can be added in order to send an interrupt to the controller 11104 to inform that a new valid angle can be read. Upon power-up, the AS5055 position sensor 11200 performs a full power-up sequence including one angle measurement. The completion of this cycle is indicated as an INT output 11242, and the angle value is stored in an internal register. Once this output is set, the AS5055 position sensor 11200 suspends to sleep mode. The controller 11104 can respond to the INT request at the INT output 11242 by reading the angle value from the AS5055 position sensor 11200 over the SPI interface 11234. Once the angle value is read by the controller 11104, the INT output 11242 is cleared again. Sending a "read angle" command by the SPI interface 11234 by the controller 11104 to the position sensor 11200 also automatically powers up the chip and starts another angle measurement. As soon as the controller 11104 has completed reading of the angle value, the INT output 11242 is cleared and a new result is stored in the angle register. The completion of the angle measurement is again indicated by setting the INT output 11242 and a corresponding flag in the status register.

Due to the measurement principle of the AS5055 position sensor 11200, only a single angle measurement is performed in very short time (~600 µs) after each power-up sequence. As soon as the measurement of one angle is completed, the AS5055 position sensor 11200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 11104. For example, an averaging of four samples reduces the jitter by 6 dB (50%).

Figure 29:
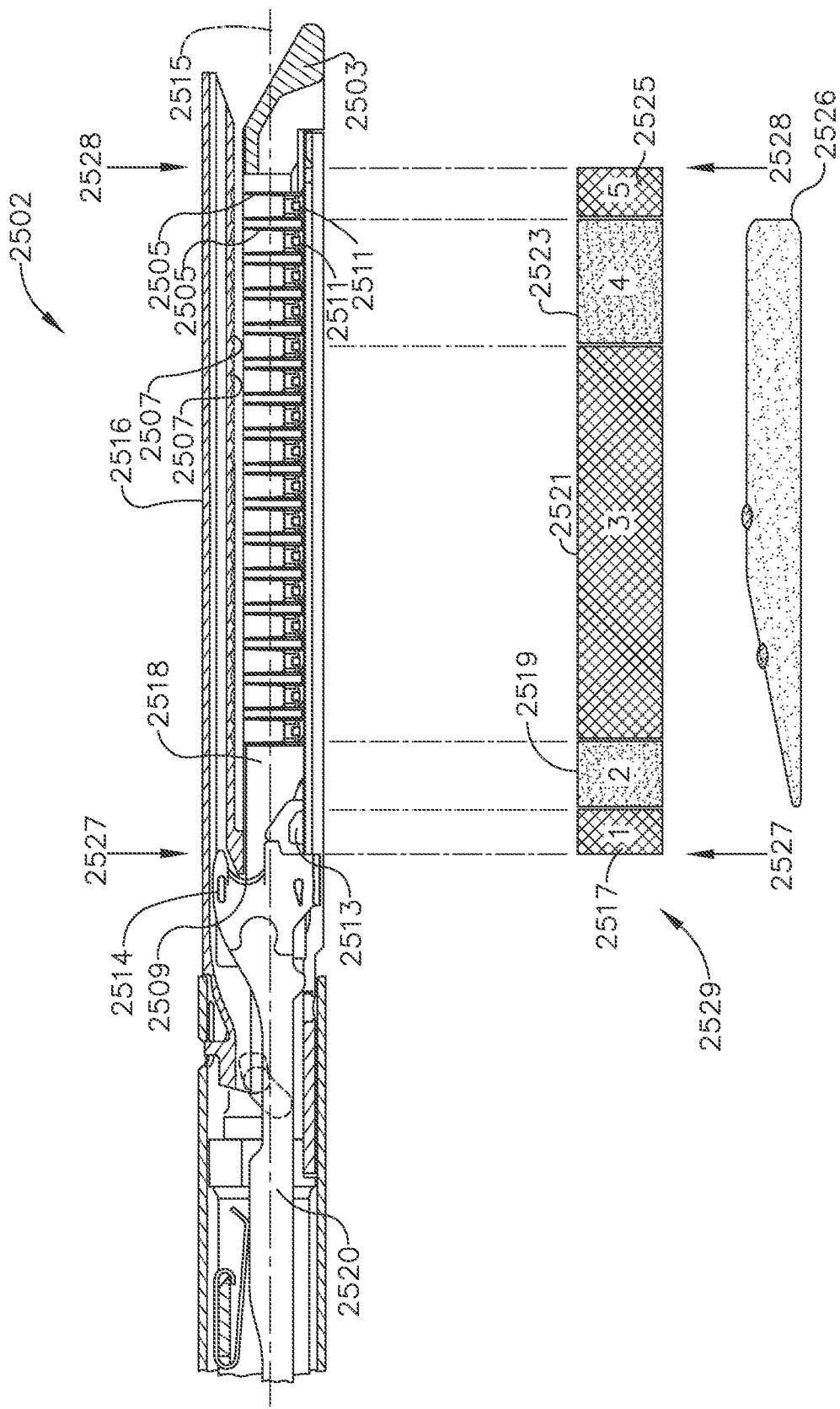
FIG. 29 is a section view of an end effector of the surgical instrument of FIG. 1 showing a firing member stroke relative to tissue grasped within the end effector according to one aspect of this disclosure.

FIG. 29 is a section view of an end effector 2502 of the robotic surgical instrument 10 showing an I-beam 2514 firing stroke relative to tissue 2526 grasped within the end effector 2502 according to one aspect of this disclosure. The end effector 2502 is configured to operate with the surgical instrument 10. The end effector 2502 comprises an anvil 2516 and an elongated channel 2503 with a staple cartridge 2518 positioned in the elongated channel 2503. A firing bar 2520 is translatable distally and proximally along a longitudinal axis 2515 of the end effector 2502. When the end effector 2502 is not articulated, the end effector 2502 is in line with the shaft of the instrument. An I-beam 2514 comprising a cutting edge 2509 is illustrated at a distal portion of the firing bar 2520. A wedge sled 2513 is positioned in the staple cartridge 2518. As the I-beam 2514 translates distally, the cutting edge 2509 contacts and may cut tissue 2526 positioned between the anvil 2516 and the staple cartridge 2518. Also, the I-beam 2514 contacts the wedge sled 2513 and pushes it distally, causing the wedge sled 2513 to contact staple drivers 2511. The staple drivers 2511 may be driven up into staples 2505, causing the staples 2505 to advance through tissue and into pockets 2507 defined in the anvil 2516, which shape the staples 2505.

An example I-beam 2514 firing stroke is illustrated by a chart 2529 aligned with the end effector 2502. Example tissue 2526 is also shown aligned with the end effector 2502. The firing member stroke may comprise a stroke begin position 2527 and a stroke end position 2528. During an I-beam 2514 firing stroke, the I-beam 2514 may be advanced distally from the stroke begin position 2527 to the stroke end position 2528. The I-beam 2514 is shown at one example location of a stroke begin position 2527. The I-beam 2514 firing member stroke chart 2529 illustrates five firing member stroke regions 2517, 2519, 2521, 2523, 2525. In a first firing stroke region 2517, the I-beam 2514 may begin to advance distally. In the first firing stroke region 2517, the I-beam 2514 may contact the wedge sled 2513 and begin to move it distally. While in the first region, however, the cutting edge 2509 may not contact tissue and the wedge sled 2513 may not contact a staple driver 2511. After static friction is overcome, the force to drive the !-beam 2514 in the first region 2517 may be substantially constant.

In the second firing member stroke region 2519, the cutting edge 2509 may begin to contact and cut tissue 2526. Also, the wedge sled 2513 may begin to contact staple drivers 2511 to drive staples 2505. Force to drive the I-beam 2514 may begin to ramp up. As shown, tissue encountered initially may be compressed and/or thinner because of the way that the anvil 2516 pivots relative to the staple cartridge 2518. In the third firing member stroke region 2521, the cutting edge 2509 may continuously contact and cut tissue 2526 and the wedge sled 2513 may repeatedly contact staple drivers 2511. Force to drive the I-beam 2514 may plateau in the third region 2521. By the fourth firing stroke region 2523, force to drive the I-beam 2514 may begin to decline. For example, tissue in the portion of the end effector 2502 corresponding to the fourth firing region 2523 may be less compressed than tissue closer to the pivot point of the anvil 2516, requiring less force to cut. Also, the cutting edge 2509 and wedge sled 2513 may reach the end of the tissue 2526 while in the fourth region 2523. When the I-beam 2514 reaches the fifth region 2525, the tissue 2526 may be completely severed. The wedge sled 2513 may contact one or more staple drivers 2511 at or near the end of the tissue. Force to advance the !-beam 2514 through the fifth region 2525 may be reduced and, in some examples, may be similar to the force to drive the I-beam 2514 in the first region 2517. At the conclusion of the firing member stroke, the I-beam 2514 may reach the stroke end position 2528. The positioning of firing member stroke regions 2517, 2519, 2521, 2523, 2525 in FIG. 29 is just one example. In some examples, different regions may begin at different positions along the end effector longitudinal axis 2515, for example, based on the positioning of tissue between the anvil 2516 and the staple cartridge 2518.

As discussed above and with reference now to FIGS. 27-29, the electric motor 11122 positioned within the master controller 13 of the surgical instrument 10 can be utilized to advance and/or retract the firing system of the shaft assembly, including the I-beam 2514, relative to the end effector 2502 of the shaft assembly in order to staple and/or incise tissue captured within the end effector 2502. The I-beam 2514 may be advanced or retracted at a desired speed, or within a range of desired speeds. The controller 1104 may be configured to control the speed of the I-beam 2514. The controller 11104 may be configured to predict the speed of the I-beam 2514 based on various parameters of the power supplied to the electric motor 11122, such as voltage and/or current, for example, and/or other operating parameters of the electric motor 11122 or external influences. The controller 11104 may be configured to predict the current speed of the I-beam 2514 based on the previous values of the current and/or voltage supplied to the electric motor 11122, and/or previous states of the system like velocity, acceleration, and/or position. The controller 11104 may be configured to sense the speed of the I-beam 2514 utilizing the absolute positioning sensor system described herein. The controller can be configured to compare the predicted speed of the I-beam 2514 and the sensed speed of the I-beam 2514 to determine whether the power to the electric motor 11122 should be increased in order to increase the speed of the I-beam 2514 and/or decreased in order to decrease the speed of the I-beam 2514.

Force acting on the I-beam 2514 may be determined using various techniques. The !-beam 2514 force may be determined by measuring the motor 2504 current, where the motor 2504 current is based on the load experienced by the I-beam 2514 as it advances distally. The I-beam 2514 force may be determined by positioning a strain gauge on the drive member, the firing member, I-beam 2514, the firing bar, and/or on a proximal end of the cutting edge 2509. The I-beam 2514 force may be determined by monitoring the actual position of the I-beam 2514 moving at an expected velocity based on the current set velocity of the motor 11122 after a predetermined elapsed period T 1 and comparing the actual position of the I-beam 2514 relative to the expected position of the I-beam 2514 based on the current set velocity of the motor 11122 at the end of the period Ti. Thus, if the actual position of the I-beam 2514 is less than the expected position of the I-beam 2514, the force on the I-beam 2514 is greater than a nominal force. Conversely, if the actual position of the I-beam 2514 is greater than the expected position of the I-beam 2514, the force on the I-beam 2514 is less than the nominal force. The difference between the actual and expected positions of the I-beam 2514 is proportional to the deviation of the force on the I-beam 2514 from the nominal force.

FIG. 30 is a schematic diagram of a robotic surgical instrument 2500 configured to operate the surgical tool described herein according to one aspect of this disclosure. The robotic surgical instrument 2500 may be programmed or configured to control distal/proximal translation of a displacement member, closure tube distal/proximal displacement, shaft rotation, and articulation, either with single or multiple articulation drive links. In one aspect, the surgical instrument 2500 may be programmed or configured to individually control a firing member, a closure member, a shaft member, and/or one or more articulation members. The surgical instrument 2500 comprises a control circuit 2510 configured to control motor-driven firing members, closure members, shaft members, and/or one or more articulation members.

In one aspect, the robotic surgical instrument 2500 comprises a control circuit 2510 configured to control an anvil 2516 and an I-beam 2514 (including a sharp cutting edge) portion of an end effector 2502, a removable staple cartridge 2518, a shaft 2540, and one or more articulation members 2542a, 2542b via a plurality of motors 2504a-2504e. A position sensor 2534 may be configured to provide position feedback of the I-beam 2514 to the control circuit 2510. Other sensors 2538 may be configured to provide feedback to the control circuit 2510. A timer/counter 2531 provides timing and counting information to the control circuit 2510. An energy source 2512 may be provided to operate the motors 2504a-2504e and a current sensor 2536 provides motor current feedback to the control circuit 2510. The motors 2504a-2504e can be individually operated by the control circuit 2510 in open loop or closed loop feedback control.

In one aspect, the control circuit 2510, may comprise one or more microcontrollers, microprocessors, or other suitable processors for executing instructions that cause the processor or processors. The control circuit 2510 may be implemented as control circuit 961 (FIG. 22), 800 (FIG. 23), 810 (FIG. 24), 820 (FIG. 25), 4420 (FIG. 26). In one aspect, a timer/counter circuit 2531 provides an output signal, such as elapsed time or a digital count, to the control circuit 2510 to correlate the position of the I-beam 2514 as determined by the position sensor 2534 with the output of the timer/counter circuit 2531 such that the control circuit 2510 can determine the position of the I-beam 2514 at a specific time (t) relative to a starting position or the time (t) when the I-beam 2514 is at a specific position relative to a starting position. The timer/counter circuit 2531 may be configured to measure elapsed time, count external evens, or time external events.

In one aspect, the control circuit 2510 may be programmed to control functions of the end effector 2502 based on one or more tissue conditions. The control circuit 2510 may be programmed to sense tissue conditions, such as thickness, either directly or indirectly, as described herein. The control circuit 2510 may be programmed to select a firing control program or closure control program based on tissue conditions. A firing control program may describe the distal motion of the displacement member. Different firing control programs may be selected to better treat different tissue conditions. For example, when thicker tissue is present, the control circuit 2510 may be programmed to translate the displacement member at a lower velocity and/or with lower power. When thinner tissue is present, the control circuit 2510 may be programmed to translate the displacement member at a higher velocity and/or with higher power.

A closure control program may control the closure force applied to the tissue by the anvil 2516. Other control programs control the rotation of the shaft 2540 and the articulation members 2542a, 2542b.

In one aspect, the control circuit 2510 may generate motor set point signals. The motor set point signals may be provided to various motor controllers 2508a-2508e. The motor controllers 2508a-2508e may comprise one or more circuits configured to provide motor drive signals to the motors 2504a-2504e to drive the motors 2504a-2504e as described herein. In some examples, the motors 2504a-2504e may be brushed DC electric motors. For example, the velocity of the motors 2504a-2504e may be proportional to the respective motor drive signals. In some examples, the motors 2504a-2540e may be brushless direct current (DC) electric motors and the respective motor drive signals 2524a-2524e may comprise a pulse-width-modulated (PWM) signal provided to one or more stator windings of the motors 2504a-2504e. Also, in some examples, the motor controllers 2508a-2508e may be omitted and the control circuit 2510 may generate the motor drive signals 2524a-2524e directly.

In one aspect, the control circuit 2510 may initially operate each of the motors 2504a-2504e in an open-loop configuration for a first open-loop portion of a stroke of the displacement member. Based on a response of the instrument 2500 during the open-loop portion of the stroke, the control circuit 2510 may select a firing control program in a closed-loop configuration. The response of the instrument may include, a translation distance of the displacement member during the open-loop portion, a time elapsed during the open-loop portion, energy provided to the motor 2504 during the open-loop portion, a sum of pulse widths of a motor drive signal, etc. After the open-loop portion, the control circuit 2510 may implement the selected firing control program for a second portion of the displacement member stroke. For example, during a closed loop portion of the stroke, the control circuit 2510 may modulate the motor 2504 based on translation data describing a position of the displacement member in a closed-loop manner to translate the displacement member at a constant velocity.

In one aspect, the motors 2504a-2504e may receive power from an energy source 2512. The energy source 2512 may be a DC power supply driven by a main AC power source, a battery, a super capacitor, or any other suitable energy source 2512. The motors 2504a-2504e may be mechanically coupled to individual movable mechanical elements such as the I-beam 2514, anvil 2516, shaft 2540, articulation 2542a, articulation 2542b via respective transmissions 2506a-2506e. The transmissions 2506a-2506e may include one or more gears or other linkage components to couple the motors 2504a-2504e to movable mechanical elements. A position sensor 2534 may sense a position of the I-beam 2514. The position sensor 2534 may be or include any type of sensor that is capable of generating position data that indicates a position of the I-beam 2514. In some examples, the position sensor 2534 may include an encoder configured to provide a series of pulses to the control circuit 2510 as the I-beam 2514 translates distally and proximally. The control circuit 2510 may track the pulses to determine the position of the I-beam 2514. Other suitable position sensor may be used, including, for example, a proximity sensor. Other types of position sensors may provide other signals indicating motion of the I-beam 2514. Also, in some examples, the position sensor 2534 may be omitted. Where any of the motors 2504a-2504e is a stepper motor, the control circuit 2510 may track the position of the I-beam 2514 by aggregating the number and direction of steps that the motor 2504 has been instructed to execute. The position sensor 2534 may be located in the end effector 2502 or at any other portion of the instrument. The outputs of each of the motors 2504a-2504e includes a torque sensor 2544a-2544e to sense force and has an encoder to sense rotation of the drive shaft.

In one aspect, the control circuit 2510 is configured to drive a firing member such as the I-beam 2514 portion of the end effector 2502. The control circuit 2510 provides a motor set point to a motor control 2508a, which provides a drive signal to the motor 2504a. The output shaft of the motor 2504a is coupled to a torque sensor 2544a and a transmission 2506a which is coupled to the I-beam 2514. The transmission 2506a comprises movable mechanical elements such as rotating elements and a firing member to control the movement of the I-beam 2514 distally and proximally along a longitudinal axis of the end effector 2502. In one aspect, the motor 2504a may be coupled to the knife gear assembly 1220, which includes a knife gear reduction set 1224 that includes a first knife drive gear 1226 and a second knife drive gear 1228. As can be seen in FIGS. 9 and 10, the knife gear reduction set 1224 is rotatably mounted to the tool mounting plate 302 such that the first knife drive gear 1226 is in meshing engagement with the knife spur gear 1222. Likewise, the second knife drive gear 1228 is in meshing engagement with a third knife drive gear 1230 that is rotatably supported on the tool mounting plate 302 in meshing engagement with the knife rack gear 1206. A torque sensor 2544a provides a firing force feedback signal to the control circuit 2510. The firing force signal represents the force required to fire or displace the I-beam 2514. A positon sensor 2534 may be configured to provide the positon of the I-beam 2514 along the firing stroke or the position of the firing member as a feedback signal to the control circuit 2510. The end effector 2502 may include additional sensors 2538 configured to provide feedback signals to the control circuit 2510. When ready to use, the control circuit 2510 may provide a firing signal to the motor control 2508a. In response to the firing signal, the motor 2504a may drive the firing member distally along the longitudinal axis of the end effector 2502 from a proximal stroke begin position to a stroke end position distal of the stroke begin position. As the firing member translates distally, an I-beam 2514 with a cutting element positioned at a distal end, advances distally to cut tissue located between the staple cartridge 2518 and the anvil 2516.

In one aspect, the control circuit 2510 is configured to drive a closure member such as the anvil 2516 portion of the end effector 2502. The control circuit 2510 provides a motor set point to a motor control 2508b, which provides a drive signal to the motor 2504b. The output shaft of the motor 2504b is coupled to a torque sensor 2544b and a transmission 2506b which is coupled to the anvil 2516. The transmission 2506b comprises movable mechanical elements such as rotating elements and a closure member to control the movement of the anvil 2516 from open and closed positions. In one aspect, the motor 2504b is coupled to the closure gear assembly 1110, which includes a closure reduction gear set 1114 that is supported in meshing engagement with the closure spur gear 1112. As can be seen in FIGS. 9 and 10, the closure reduction gear set 1114 includes a driven gear 1116 that is rotatably supported in meshing engagement with the closure spur gear 1112. The closure reduction gear set 1114 further includes a first closure drive gear 1118 that is in meshing engagement with a second closure drive gear 1120 that is rotatably supported on the tool mounting plate 302 in meshing engagement with the closure rack gear 1106. The torque sensor 2544b provides a closure force feedback signal to the control circuit 2510. The closure force feedback signal represents the closure force applied to the anvil 2516. The positon sensor 2534 may be configured to provide the positon of the closure member as a feedback signal to the control circuit 2510. Additional sensors 2538 in the end effector 2502 may provide the closure force feedback signal to the control circuit 2510. The pivotable anvil 2516 is positioned opposite the staple cartridge 2518. When ready to use, the control circuit 2510 may provide a closure signal to the motor control 2508b. In response to the closure signal, the motor 2504b advances a closure member to grasp tissue between the anvil 2516 and the staple cartridge 2518.

In one aspect, the control circuit 2510 is configured to rotate a shaft member such as the shaft 2540 to rotate the end effector 2502. The control circuit 2510 provides a motor set point to a motor control 2508c, which provides a drive signal to the motor 2504c. The output shaft of the motor 2504c is coupled to a torque sensor 2544c and a transmission 2506c which is coupled to the shaft 2540. The transmission 2506c comprises movable mechanical elements such as rotating elements to control the rotation of the shaft 2540 clockwise or counterclockwise up to and over 360°. In one aspect, the motor 2504c is coupled to the rotational transmission assembly 1069, which includes a tube gear segment 1062 that is formed on (or attached to) the proximal end 1060 of the proximal closure tube 1040 for operable engagement by a rotational gear assembly 1070 that is operably supported on the tool mounting plate 302. As shown in FIG. 8, the rotational gear assembly 1070, in at least one aspect, comprises a rotation drive gear 1072 that is coupled to a corresponding first one of the driven discs or elements 304 on the adapter side 307 of the tool mounting plate 302 when the tool mounting portion 300 is coupled to the tool drive assembly 101. See FIG. 6. The rotational gear assembly 1070 further comprises a rotary driven gear 1074 that is rotatably supported on the tool mounting plate 302 in meshing engagement with the tube gear segment 1062 and the rotation drive gear 1072. The torque sensor 2544c provides a rotation force feedback signal to the control circuit 2510. The rotation force feedback signal represents the rotation force applied to the shaft 2540. The positon sensor 2534 may be configured to provide the position of the closure member as a feedback signal to the control circuit 2510. Additional sensors 2538 such as a shaft encoder may provide the rotational position of the shaft 2540 to the control circuit 2510.

In one aspect, the control circuit 2510 is configured to articulate the end effector 2502. The control circuit 2510 provides a motor set point to a motor control 2508d, which provides a drive signal to the motor 2504d. The output shaft of the motor 2504d is coupled to a torque sensor 2544d and a transmission 2506d which is coupled to an articulation member 2542a. The transmission 2506d comprises movable mechanical elements such as articulation elements to control the articulation of the end effector 2502±65°. In one aspect, the motor 2504d is coupled to the articulation nut 1260, which is rotatably journaled on the proximal end portion of the distal spine portion 1050 and is rotatably driven thereon by an articulation gear assembly 1270. More specifically and with reference to FIG. 8, in at least one aspect, the articulation gear assembly 1270 includes an articulation spur gear 1272 that is coupled to a corresponding fourth one of the driven discs or elements 304 on the adapter side 307 of the tool mounting plate 302. The torque sensor 2544d provides an articulation force feedback signal to the control circuit 2510. The articulation force feedback signal represents the articulation force applied to the end effector 2502. Sensors 2538 such as an articulation encoder may provide the articulation position of the end effector 2502 to the control circuit 2510.

In another aspect, the articulation function of the robotic surgical system 10 may comprise two drive members 2542a, 2542b or links. These drive members 2542a, 2542b are driven by separate disks on the robot interface (the rack) which are driven by the two motors 2508d, 2508e. When the separate firing motor 2504a is provided, each articulation link 2542a, 2542b can be antagonistically driven with respect to the other link in order to provide resistive holding motion and load to the head when it is not moving and to provide articulation motion as the head is articulated. The drive members 2542a, 2542b or links attach to the head at a fixed radius as the head is rotated. Accordingly, the mechanical advantage of the push and pull link changes as the head is rotated. This change in the mechanical advantage may be more pronounced with other articulation link drive systems.

In one aspect, the end effector 2502 may be implemented as the surgical end effector 1012, 3000, 5650, 6460, 6470 shown and described in connection with FIGS. 4, 6, 8-12, 15A, 15B, 19, 20, and 21. In one aspect, the I-beam 2514 portion of the end effector 2502 may be implemented as the knife member 1032, 3005, 2514 shown and described in connection with FIGS. 11A, 12, 29. The I-beam 2514 comprises a knife body that operably supports a tissue cutting blade 2509 (FIG. 29) thereon. In one aspect, the anvil 2516 portion of the end effector 2502 may be implemented as the anvil 1024, 3002, 5502, 5602, 6472 shown and described in connection with FIGS. 4, 6-14, 20, and 21.

In one aspect, the one or more motors 2504a-2504e may comprise a brushed DC motor with gearbox and mechanical links to a firing member, closure member, or articulation member. Another example are electric motors 2504a-2504e that operate the movable mechanical elements such as the displacement member, articulation links, closure tube, and shaft. An outside influence is an unmeasured, unpredictable influence of things like tissue, surrounding bodies and friction on the physical system. Such outside influence can be referred to as drag which acts in opposition to an electric motor 2504a-2504e. The outside influence, such as drag, may cause the operation of the physical system to deviate from a desired operation of the physical system.

In one aspect, the position sensor 2534 may be implemented as an absolute positioning system as shown and described in connection with FIGS. 27 and 28. In one aspect, the position sensor 2534 may comprise a magnetic rotary absolute positioning system implemented as an AS5055EQFT single-chip magnetic rotary position sensor available from Austria Microsystems, AG. The position sensor 2534 may interface with the control circuit 2510 to provide an absolute positioning system. The position may include multiple Hall-effect elements located above a magnet and coupled to a CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations.

In one aspect, the control circuit 2510 may be in communication with one or more sensors 2538. The sensors 2538 may be positioned on the end effector 2502 and adapted to operate with the surgical instrument 2500 to measure the various derived parameters such as gap distance versus time, tissue compression versus time, and anvil strain versus time. The sensors 2538 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 2502. The sensors 2538 may include one or more sensors. The sensors 2538 may be located on the staple cartridge 2518 deck to determine tissue location using segmented electrodes. The torque sensors 2544a-2544e may be configured to sense force such as firing force, closure force, articulation force, among others. Accordingly, the control circuit 26510 can sense: (1) the closure load experienced by the distal closure tube and its position; (2) the firing member at the rack and its position; (3) what portion of the staple cartridge 2518 has tissue on it; and (4) sense the load and positon on both articulation rods.

In one aspect, the one or more sensors 2538 may comprise a strain gauge, such as a micro-strain gauge, configured to measure the magnitude of the strain in the anvil 2516 during a clamped condition. The strain gauge provides an electrical signal whose amplitude varies with the magnitude of the strain. The sensors 2538 may comprise a pressure sensor configured to detect a pressure generated by the presence of compressed tissue between the anvil 2516 and the staple cartridge 2518. The sensors 2538 may be configured to detect impedance of a tissue section located between the anvil 2516 and the staple cartridge 2518 that is indicative of the thickness and/or fullness of tissue located therebetween.

In one aspect, the sensors 2538 may be implemented as one or more limit switches, electromechanical devices, solid state switches, Hall-effect devices, magneto-resistive (MR) devices, giant magneto-resistive (GMR) devices, magnetometers, among others. In other implementations, the sensors 2538 may be implemented as solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). In other implementations, the sensors 2538 may include electrical conductorless switches, ultrasonic switches, accelerometers, inertial sensors, among others.

In one aspect, the sensors 2538 may be configured to measure forces exerted on the anvil 2516 by the closure drive system. For example, one or more sensors 2538 can be at an interaction point between the closure tube and the anvil 2516 to detect the closure forces applied by the closure tube to the anvil 2516. The forces exerted on the anvil 2516 can be representative of the tissue compression experienced by the tissue section captured between the anvil 2516 and the staple cartridge 2518. The one or more sensors 2538 can be positioned at various interaction points along the closure drive system to detect the closure forces applied to the anvil 2516 by the closure drive system. The one or more sensors 2538 may be sampled in real time during a clamping operation by the processor of the control circuit 2510. The control circuit 2510 receives real-time sample measurements to provide analyze time based information and assess, in real time, closure forces applied to the anvil 2516.

In one aspect, a current sensor 2536 can be employed to measure the current drawn by each of the motors 2504a-2504e. The force required to advance any of the movable mechanical elements such as the I-beam 2514 corresponds to the current drawn by a motor 2504a-2504e. The force is converted to a digital signal and provided to the control circuit 2510. The control circuit 2510 can be configured to simulate the response of the actual system of the instrument in the software of the controller. A displacement member can be actuated to move an I-beam 2514 in the end effector 2502 at or near a target velocity. The robotic surgical instrument 2500 can include a feedback controller, which can be one of any feedback controllers, including, but not limited to a PID, a State Feedback, LQR, and/or an Adaptive controller, for example. The robotic surgical instrument 2500 can include a power source to convert the signal from the feedback controller into a physical input such as case voltage, pulse width modulated (PWM) voltage, frequency modulated voltage, current, torque, and/or force, for example.

Closed Loop Velocity Control Techniques Based on Sensed Tissue Parameters for Robotic Surgical Instrument In use, a robotic surgical instrument may sense and identify certain tissue conditions in the end effector that may affect performance of the staple formation and tissue cutting process. Accordingly, in such situations, the displacement, e.g., advancement or retraction, process for controlling the velocity of the firing member may be based on the sensed and identified parameters of tissue gap, coupling member load, knife advancement rate, and tissue compression In one aspect, the present disclosure provides various techniques for controlling the advancement or retraction velocity of a displacement member of a robotic surgical instrument based on the sensed and identified parameters of end effector gap (e.g., indicative of tissue thickness), coupling member load such as closure force (FTC) or firing force (FTF), knife advancement rate, tissue impedance, tissue compression, tissue coverage on cartridge, among other parameters.

FIG. 31 is a chart 12000 illustrating techniques for controlling the advancement or retraction velocity of a displacement member of a robotic surgical instrument according to one aspect of this disclosure. The chart 12000 depicts firing the displacement member from an anvil closure condition or from a firing condition for tissue that is thinner than anticipated or thicker than anticipated. The first column 12002 tabulates variables or parameters that the velocity control is based on such as end effector gap between the anvil and the staple cartridge, closure force or firing force, velocity of the knife, tissue impedance, and tissue coverage on the cartridge. The second column 12004 tabulates the initial velocity selection from closure of the anvil of either slow or fast, otherwise known as the set velocity or command velocity based on the sensed and identified parameters tabulated in the first column 12002. The third column 12006 tabulates decreasing or increasing firing velocity updates over the length of the cartridge (e.g., the main X mm in different sections, where X is the length of the cartridge such as 10 mm-60 mm, or greater) based on the sensed and identified parameters tabulated in the first column 12002.

Accordingly, with reference now to the firing process from closure during the anvil closure phase tabulated in the second column 12004 based on the tissue gap parameter, if the measured tissue gap in the end effector is less than a nominal tissue gap and the initial set velocity of the displacement member is slow, the velocity of the displacement member is increased as indicated by the ++ symbol, where the number of the "+" or "−" symbols refers to proportionally increase or decrease the set velocity, respectively. In contrast, if the measured tissue gap is greater than the nominal tissue gap and the initial set velocity of the displacement member is fast, the velocity of the displacement member is decreased as indicated by the −− symbol.

With reference now to the firing process from closure during the anvil closure phase tabulated in the second column 12004 based on the closure force (FTC) parameter, if the measured FTC is less than a threshold force and the initial set velocity of the displacement member is slow, the velocity of the displacement member may be increased as indicated by the ++ symbol. In contrast, if the measured FTC is greater than the threshold force and the initial set velocity of the displacement member is fast, the velocity of the displacement member is decreased as indicated by the -- symbol.

The next variable, the knife velocity parameter (e.g., velocity of the displacement member), is skipped because the initial velocity of the knife from closure is always zero. Accordingly, turning now to the firing process from closure during the anvil closure phase tabulated in the second column 12004 based on the tissue impedance parameter, if the measured tissue impedance is lower than expected, indicating that the tissue is thinner than expected, and the initial set velocity of the displacement member is slow, the velocity of the displacement member may be increased as indicated by the ++ symbol. In contrast, if the measured tissue impedance is greater than the threshold tissue impedance, indicating that the tissue is thicker than expected, and the initial set velocity of the displacement member is fast, the velocity of the displacement member is decreased as indicated by the -- symbol.

With reference now to the firing process from closure during the anvil closure phase tabulated in the second column 12004 based on cartridge coverage parameter, for example, based on tissue partially or entirely covering the space between the anvil and staple cartridge, if the measured tissue does not cover the entire cartridge and the initial set velocity of the displacement member is slow, the velocity of the displacement member may be increased as indicated by the + symbol. In contrast, if the measured tissue covers the entire cartridge and the initial set velocity of the displacement member is fast, the velocity of the displacement member is decreased as indicated by the -- symbol.

The description now turns to the firing phase tabulated in the third column 12006. Accordingly, with reference to the tissue gap parameter, if during the firing phase at the current set firing velocity, the measured tissue gap in the end effector decreases, the velocity of the displacement member is increased as indicated by the + symbol. In contrast, if during the firing phase at the current set firing velocity, the measured tissue gap in the end effector increases, the velocity of the displacement member is decreased as indicated by the - symbol.

With reference to the FTF parameter, if during the firing phase at the current set firing velocity, the measured FTF decreases, the set velocity of the displacement member is increased as indicated by the ++ symbol. In contrast, if during the firing phase at the current set firing velocity, the measured FTF increases, the set velocity of the displacement member is decreased as indicated by the -- symbol.

With reference to the knife velocity parameter (e.g., velocity of the displacement) as indicated in the third column 12006 the - symbol indicates a decrease in set velocity and the + symbol indicates an increase in set velocity. Accordingly, turning now to the tissue impedance parameter, if during the firing phase at the current set firing velocity, the measured tissue impedance decreases (indicating a decrease in tissue thickness), the set velocity of the displacement member is increased as indicated by the + symbol. In contrast, if during the firing phase at the current set firing velocity, the measured tissue impedance increases (indicating an increase in tissue thickness), the set velocity of the displacement member is decreased as indicated by the - symbol.

Finally, with reference now to the cartridge coverage parameter, if during the firing phase at the current set firing velocity, the measured cartridge coverage decreases, the set velocity of the displacement member is increased as indicated by the + symbol. In contrast, if during the firing phase at the current set firing velocity, the measured cartridge coverage increases, the set velocity of the displacement member is decreased as indicated by the - symbol.

Figure 32:
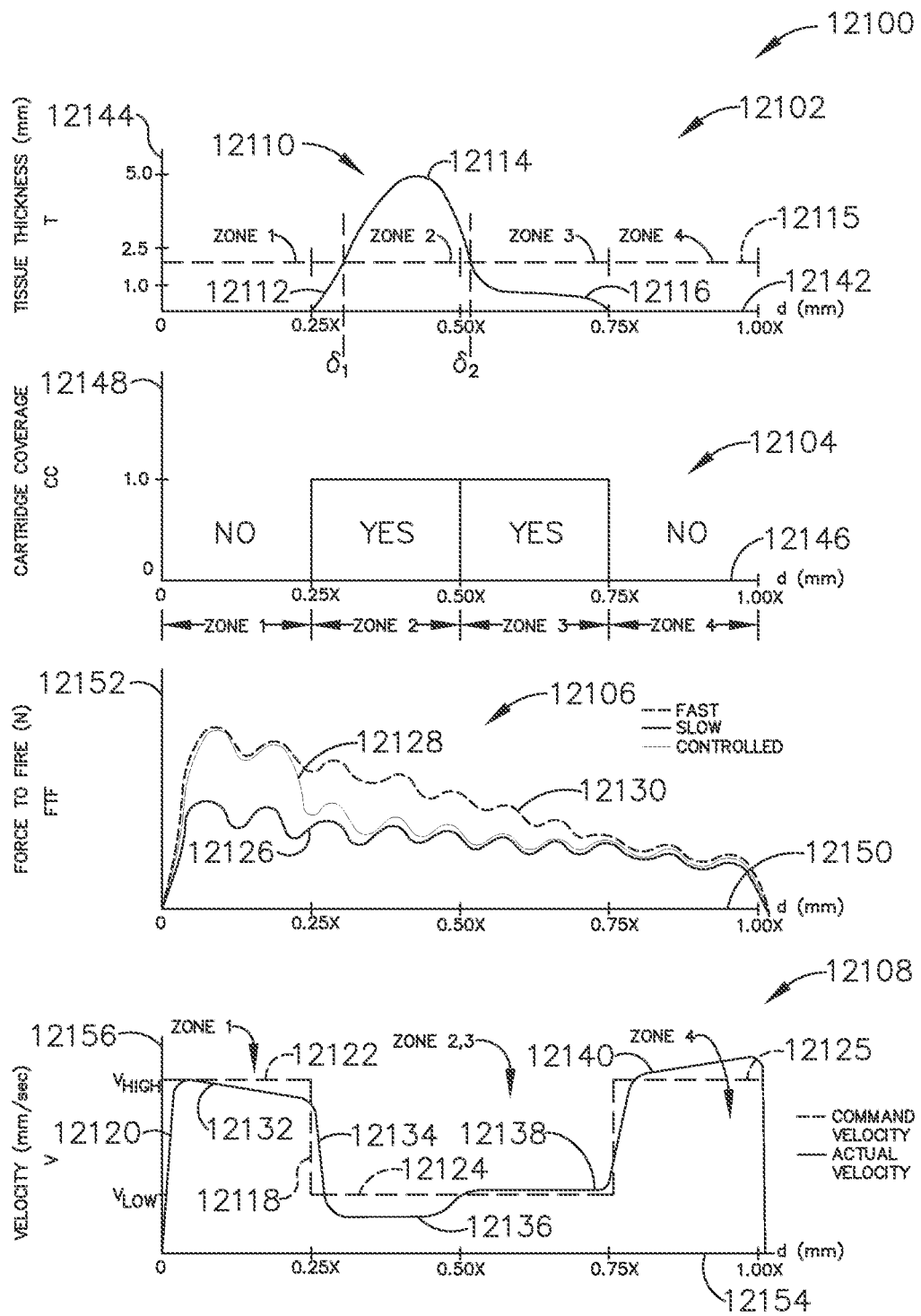
FIG. 32 is a graphical depiction of a closed loop velocity control process according to one aspect of this disclosure.

With the above background, the description now turns to FIG. 32, which is a graphical depiction of a closed loop velocity control process 12100 according to one aspect of this disclosure. The top graph 12102 depicts variation in tissue thickness as a function of position along the staple cartridge. The horizontal axis 12142 is scaled to represent the length of the staple cartridge X mm, where X is 10-60 mm, for example. Accordingly, for a 60 mm staple cartridge, X=60 mm. The vertical axis 12144 represents tissue thickness T (mm). The horizontal axis 242 also is divided into four zones (Zone 1-Zone 4) of equal length. As shown, the thickness of the tissue 12110 varies 0.25× to 0.74× (15-45 mm for a 60 mm cartridge). The control circuit monitors the tissue thickness along the length of the cartridge and compares the thickness of the tissue 12110 to a threshold thickness 12115. The tissue 12110 thickness plot indicates that tissue is located only in Zone 2 and Zone 3 of the cartridge and not in Zone 1 and Zone 4. Also, the thickness of tissue 12110 is above the threshold thickness 12115 between $\delta_1$ and $\delta_2$ such that tissue segments 12112, 12116 are below the threshold thickness 12115 and the thickness of a portion of tissue 12114 is located above the threshold thickness 12115. Accordingly, as discussed in the chart 12000 in FIG. 31, the closed loop velocity control process will be adjusted based on the tissue condition parameters encountered in the closure phase and the firing phase.

The second graph 12104 from the top depicts tissue 12110 coverage as a function of position along staple cartridge, where the horizontal axis 12142 represents the length of the staple cartridge X mm, and the vertical axis 12148 represents the presence of tissue 12110 in a particular zone (Zone 1-Zone 4). The cartridge coverage is represented as a binary variable such that if tissue 12110 is present, the cartridge coverage is 1 and if tissue 12110 is not present the cartridge coverage is 0. As shown, the cartridge coverage is 0 in Zone 1 and Zone 4 and is 1 in Zone 2 and Zone 3.

Figure 33:
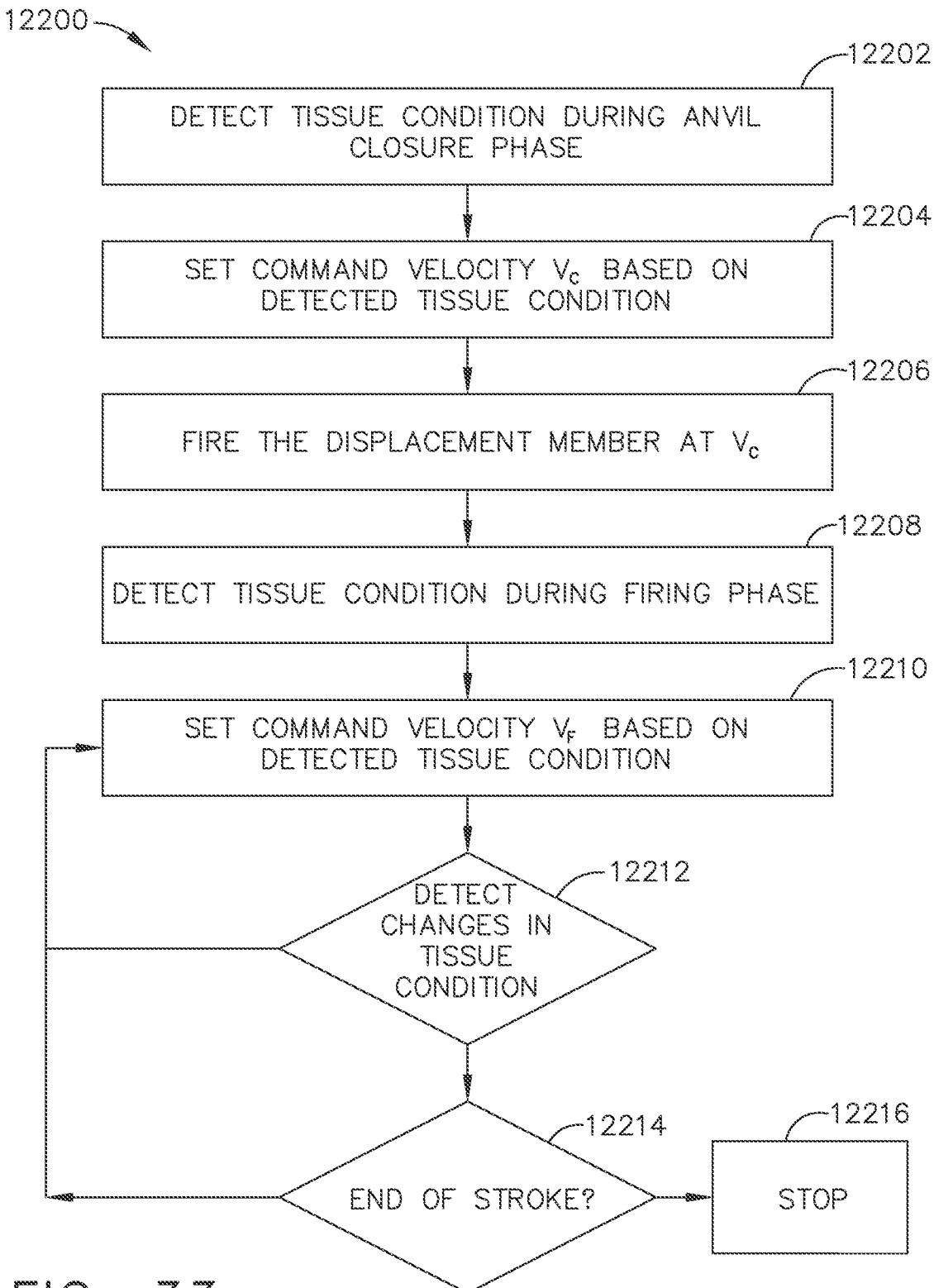
FIG. 33 is a logic flow diagram depicting a process of a control program or a logic configuration for determining tissue conditions in an end effector and adjusting command velocity accordingly according to one aspect of this disclosure.

The third graph 12106 from the top, depicts firing force (N) as a function of position along the staple cartridge for slow and fast traversal rates and for a controlled velocity. The horizontal axis 12150 represents the length of the staple cartridge X mm, and the vertical axis 12148 represents firing force (N). As shown, the slow rate FTF curve 12126 has a lower force profile that the fast rate curve 12130. The controlled curve 12128 represents the force profile when the process 12200 discussed in reference to FIG. 33 is executed by the control circuit 2510 (FIG. 30). Generally, when the knife or the displacement member encounters tissue 12110 that is thicker that the threshold thickness 12115 the control circuit decreases the set velocity of the displacement member as discussed in more detail in reference to the bottom graph 12108.

The bottom graph 12108 represents command velocity 12118 (dashed line) and actual velocity 12120 (solid line) as a function of position along the staple cartridge where the horizontal axis 12154 represents the length of the staple cartridge X mm and the vertical axis 12156 represents command velocity (mm/sec). The command velocity 12118 is the motor velocity set by the control circuit and the actual velocity 12120 is the actual velocity as measured by the control circuit via feedback from the position sensor and timer/counter circuit. The command velocity 12118 is determined based on the tissue conditions experienced during the initial closure phase and the firing phase. The control circuit adjusts the command velocity 12118 based on the closed loop control process 12200 described in reference to FIG. 33 to compensate, for example, for tissue thickness and cartridge coverage. Nevertheless, the command velocity 12118 may be adjusted by the closed loop control process 12200 based on any of the parameters or variables described in the first column 12002 of the chart 12000 shown in FIG. 31.

In the example of FIG. 32, upon detecting that there is no tissue in Zone 1, the control circuit increases the command velocity from 0 mm/sec to $V_{HIGH}$ 12122 during the Zone 1 period until tissue 12110 is encountered by the I-beam knife at the beginning of Zone 2 (0.25× mm) at which point the command velocity 12118 is decreased to the velocity Wow 12124. The velocity $V_{LOW}$ 12124 is maintained until the I-beam knife exits Zone 3 (0.75×) at which point the control circuit adjusts the command velocity 12118 back to $V_{HIGH}$ 12125 in Zone 4. The actual velocity 12120 profile substantially tracks the command velocity 12118, but includes a response time delay between the time that the command velocity 12118 is set by the control circuit until the displacement member reaches the command velocity 12118. For example, the actual velocity segment 12132 reaches $V_{HIGH}$ 12122 and droops slightly in Zone 1 due to the compression force applied to the tissue 12110. In Zone 2, the actual velocity 12120 drops as shown by segment 12134 as the displacement member tracks the command velocity 12118. In Zone 2, between $\delta_1$ and $\delta_2$ where the tissue thickness of tissue segment 12114 is above the tissue thickness threshold 12115. Accordingly, in Zone 2, the actual velocity 12120 segment 12136 is slightly lower than the command velocity 12118 due to the thicker tissue segment 12114 encountered by the I-beam knife. In Zone 3, as the tissue segment 12116 drops below the tissue thickness threshold 12115 but remains above zero, the actual velocity 12120 segment 12138 tracks the command velocity 12118 $V_{LOW}$ 12124 more closely. Finally, in Zone 4, a tissue free zone, the actual velocity 12120 ramps up to the command velocity 12125. The actual velocity segment 12140 rises slightly above $V_{HIGH}$ and then drops to zero at the end of stroke. Referring to the controlled curve 12128, the firing force profile drops significantly by reducing the command velocity 12118 and accordingly, the actual velocity 12120 or advancement velocity of the I-beam knife.

FIG. 33 is a logic flow diagram depicting a process 12200 of a control program or a logic configuration for determining tissue conditions in an end effector and adjusting command velocity accordingly according to one aspect of this disclosure. The process 12200 will be described in reference to the robotic surgical instrument 2500 shown in FIG. 30 programmed to control distal translation of a displacement member, closure tube travel, shaft rotation, and articulation, either with single or dual articulation drive links, according to one aspect of this disclosure. One or more sensors 2538 of the robotic surgical instrument 2500 detect 12202 tissue conditions in the end effector 2502 during an anvil 2516 closure phase, e.g., while the anvil 2516 closes on the staple cartridge 2518. The outputs of the one or more sensors 2538 are provided to the control circuit 2510. The control circuit 2510 sets 12204 the command velocity of the motor 2504*a* by applying a motor set point to the motor control 2508*a* which in turn applies a motor drive signal to the motor 2504*a* to set the command velocity of the motor 2504*a* to drive or fire 12206 the displacement member coupled to the I-beam 2514 at the command velocity during the closure phase. The torque sensor 2544*a* at the output shaft of the motor 2504*a* may provide a torque signal to the additional control circuit 2510 to detect force encountered by the I-beam 2514 during travel within the end effector 2502. A position sensor 2534 is configured to detect the position of the I-beam 2514 or other displacement member of the robotic surgical system 2500.

The process 12200 continues during the firing phase. Accordingly, the one or more sensors 2538 detect 12208 tissue conditions in the end effector 2502 during the firing phase of the I-beam 2514. The control circuit 2510 receives inputs from the one or more sensor 2538 and additionally from the torques sensor 2544*a*, the position sensor 2534, and optionally the current sensor 2536 to set 12210 the command velocity of the displacement member coupled to the !-beam 2514 based on the detected 12208 tissue conditions. The displacement member advances at the set velocity until changes in the tissue conditions are detected 12212. The command velocity is then adjusted 12210 to a new command velocity based on the detected 12212 tissue conditions. Reference is made to the chart 12000 in FIG. 31 and accompanying description for firing the displacement member from an anvil 2516 closure condition or from a firing condition for tissue based on tissue conditions encountered in the end effector 2502. The process 12200 continues 12214 until the displacement member, e.g., the I-beam 2514, reaches the end of stroke 12216.

According to the process 12200 the control circuit 2510 of the robotic surgical system 2500 is configured to detect 12202 a condition at an end effector 2502 during a closure phase. The control circuit 2510 sets 12204 the command velocity of the motor 2504*a* coupled to a displacement member, e.g., the I-beam 2514, coupled to the end effector 2502 based on the detected 12202 condition at the end effector 2502 during the closure phase. The control circuit 2510 fires 12206 the displacement member at the set command velocity. The control circuit 2510 detects 12208 a condition at the end effector 2502 during a firing phase. The control circuit sets 1210 the command velocity of the motor 2504*a* based on the condition detected 12208 at the end effector 2502 during the firing phase.

During the closure phase or the firing phase, the control circuit 2510 of the robotic surgical system 2500 is configured to detect tissue thickness based on sensors 2538 and is configured to detect a gap defined between the anvil 2516 and the staple cartridge 2518 portion of the end effector 2502 based on the sensors 2538 and adjust the command velocity based on the gap and the command velocity at the time the gap is detected. Tissue thickness may be detected by various sensors 2538 such as those shown in FIGS. 13-21 and accompanying description.

The control circuit 2510 may be configured to detect a closure force defined as the force experienced by the anvil 2516 and the staple cartridge 2518 portion of the end effector 2502 closed on tissue located therebetween and adjusts the command velocity based on the closure force and the command velocity at the time the force is detected. The force may be detected by force sensors, such as strain gauges, located in the anvil 2516 or the staple cartridge 2518 or other location in the end effector 2502 such as those shown in FIGS. 13-21 and accompanying description. In addition closure force may be provided by the torque sensor 2544*b* coupled to a second motor 2508*b*.

The control circuit 2510 may be configured to detect a firing force to displace the displacement member and adjust the command velocity based on the firing force and the command velocity at the time the force is detected. The firing force may be provided to the control circuit 2510 by sensors 2538 or the torque sensor 2544a coupled to the output shaft of the motor 2508a.

The control circuit 2510 may be configured to detect the electrical impedance of the tissue located between the anvil 2516 and the staple cartridge 2518 of the end effector 2502 and adjust the command velocity based on the electrical impedance and the command velocity at the time the impedance is detected. The electrical impedance may be sensed using a variety of sensors 2538 such as those shown in FIGS. 13-21 and accompanying description. Electrical current driven through the tissue located between the electrode segments can be used by the control circuit 2510 to measure the tissue impedance.

The control circuit 2510 may be configured to detect the coverage of tissue located between an anvil and a staple cartridge portion of the end effector and adjust the command velocity based on the coverage and the command velocity at the time the coverage is detected. Tissue coverage may be detected using various sensors such as those shown in FIGS. 13-21 and accompanying description.

The functions or processes 12200 described herein may be executed by any of the processing circuits described herein, such as the control circuit 961 (FIG. 22), 800 (FIG. 23), 810 (FIG. 24), 820 (FIG. 25), 4420 (FIG. 26), and/or control circuit 2510 (FIG. 30). Aspects of the motorized surgical instrument may be practiced without the specific details disclosed herein. Some aspects have been shown as block diagrams rather than detail.

Various aspects of the subject matter described herein are set out in the following examples:

Example 1. A robotic surgical system, comprising: a control circuit configured to: detect a condition at an end effector during a closure phase; set command velocity of a motor coupled to a displacement member coupled to the end effector based on the detected condition at the end effector during the closure phase; fire the displacement member at the set command velocity; detect a condition at the end effector during a firing phase; and set command velocity of the motor based on the condition detected at the end effector during the firing phase.

Example 2. The robotic surgical system of Example 1, wherein the condition during the closure phase or the firing phase is tissue thickness and the control circuit is configured to detect a gap defined between an anvil and a staple cartridge portion of the end effector and adjust the command velocity based on the gap and the command velocity at the time the gap is detected.

Example 3. The robotic surgical system of any one of Example 1 through Example 2, wherein the condition during the closure phase is closure force applied to an anvil toward a staple cartridge and the control circuit is configured to detect a closure force defined as the force experienced by the anvil and the staple cartridge portion of the end effector closed on tissue located therebetween and adjust the command velocity based on the closure force and the command velocity at the time the force is detected.

Example 4. The robotic surgical system of any one of Example 1 through Example 3, wherein the condition during the firing phase is firing force to displace the displacement member and the control circuit is configured to detect a firing force to displace the displacement member and adjust the command velocity based on the firing force and the command velocity at the time the force is detected.

Example 5. The robotic surgical system of any one of Example 1 through Example 4, wherein the condition during the closure phase or the firing phase is electrical impedance of tissue located between an anvil and a cartridge in the end effector and the control circuit is configured to detect the electrical impedance of the tissue located between the anvil and the staple cartridge of the end effector and adjust the command velocity based on the electrical impedance and the command velocity at the time the impedance is detected.

Example 6. The robotic surgical system of any one of Example 1 through Example 5, wherein the condition during the closure phase or the firing phase is coverage of tissue in the end effector and the control circuit is configured to detect the coverage of tissue located between an anvil and a staple cartridge portion of the end effector and adjust the command velocity based on the coverage and the command velocity at the time the coverage is detected.

Example 7. The robotic surgical system of any one of Example 1 through Example 6, wherein the control circuit is configured to adjust the command velocity during the firing phase to adjust the velocity of the displacement member while firing.

Example 8. A robotic surgical system, comprising: a control circuit coupled to a motor and configured to set a command velocity of the motor during a closure phase or a firing phase, wherein the motor is configured to drive a displacement member at the command velocity, wherein the control circuit is configured to: detect a first condition at the end effector; detect a second condition at the end effector; set the command velocity of the motor based on the detected first and second conditions at the end effector; and fire the displacement member at the set command velocity.

Example 9. The robotic surgical system of any one of Example 8, wherein the first condition is tissue coverage in segmented sections of the end effector and the control circuit is configured to: receive tissue presence from a sensor located in a section in a section of the end effector; set the command velocity of the motor to a first velocity in sections of the end effector where there is no tissue; and set the command velocity of the motor to a second velocity in sections of the end effector where the tissue is located in the end effector, wherein the second velocity is less than the first velocity.

Example 10. The robotic surgical system of any one of Example 8 through Example 9, wherein the first condition is tissue thickness located at the end effector and the control circuit is configured to: receive tissue thickness from a gap sensor located in the end effector; and set the command velocity of the motor to a third velocity in sections of the end effector where the tissue thickness is greater than a threshold thickness, and wherein the third velocity is less than the second velocity.

Example 11. The robotic surgical system of any one of Example 8 through Example 10, wherein the first condition is closure force applied to the end effector and the control circuit is configured to: receive closure force from a sensor located in the end effector; and set the command velocity of the motor to a third velocity in sections of the end effector where the closure force is greater than a threshold force, and wherein the third velocity is less than the second velocity.

Example 12. The robotic surgical system of any one of Example 8 through Example 11, wherein the first condition is firing force to displace the displacement member and the control circuit is configured to: receive firing force from a sensor coupled to the output of the motor; and set the command velocity of the motor to a third velocity in sections of the end effector where the closure force is greater than a threshold force, and wherein the third velocity is less than the second velocity.

Example 13. The robotic surgical system of any one of Example 8 through Example 12, wherein the first condition is tissue impedance at the end effector and the control circuit is configured to: receive tissue impedance from a sensor located in the end effector; and set the command velocity of the motor to a third velocity in sections of the end effector where the impedance is greater than a threshold impedance, and wherein the third velocity is less than the second velocity.

Example 14. The robotic surgical system of any one of Example 8 through Example 13, wherein the second condition is tissue coverage in segmented sections of the end effector and the control circuit is configured to: receive tissue presence from a sensor located in a section in a section of the end effector; set the command velocity of the motor to a first velocity in sections of the end effector where there is no tissue; and set the command velocity of the motor to a second velocity in sections of the end effector where the tissue is located in the end effector, wherein the second velocity is less than the first velocity.

Example 15. The robotic surgical system of any one of Example 8 through Example 14, wherein the second condition is tissue thickness located at the end effector and the control circuit is configured to: receive tissue thickness from a gap sensor located in the end effector; and set the command velocity of the motor to a third velocity in sections of the end effector where the tissue thickness is greater than a threshold thickness, and wherein the third velocity is less than the second velocity.

Example 16. The robotic surgical system of any one of Example 8 through Example 15, wherein the second condition is closure force applied to the end effector and the control circuit is configured to: receive closure force from a sensor located in the end effector; and set the command velocity of the motor to a third velocity in sections of the end effector where the closure force is greater than a threshold force, and wherein the third velocity is less than the second velocity.

Example 17. The robotic surgical system of any one of Example 8 through Example 16, wherein the second condition is firing force to displace the displacement member and the control circuit is configured to: receive firing force from a sensor coupled to the output of the motor; and set the command velocity of the motor to a third velocity in sections of the end effector where the closure force is greater than a threshold force, and wherein the third velocity is less than the second velocity.

Example 18. The robotic surgical system of any one of Example 8 through Example 17, wherein the second condition is tissue impedance at the end effector and the control circuit is configured to: receive tissue impedance from a sensor located in the end effector; and set the command velocity of the motor to a third velocity in sections of the end effector where the impedance is greater than a threshold impedance, and wherein the third velocity is less than the second velocity.

Example 19. A robotic surgical system, comprising: a first motor to drive a displacement member coupled to a cutting member; a second motor to drive a closure tube coupled to an anvil portion of an end effector, wherein the closure tube is configured to close or open the anvil; and a control circuit coupled to the first and second motor, wherein control circuit is configured to set a command velocity of the first motor during a closure phase or a firing phase and set a command velocity of the second motor to apply a closure force to the closure tube coupled to the anvil, wherein the control circuit is configured to: detect a first condition at the end effector; detect a second condition at the end effector; set the first command velocity of the motor based on the detected first and second conditions at the end effector; and fire the displacement member at the first set command velocity.

Example 20. The robotic surgical system of Example 19, wherein the first condition is tissue coverage in segmented sections of the end effector and the control circuit is configured to: receive tissue presence from a sensor located in a section in a section of the end effector; set the command velocity of the first motor to a first velocity in sections of the end effector where there is no tissue; and set the command of the first motor to a second velocity in sections of the end effector where the tissue is located in the end effector; wherein the second velocity is less than the first velocity.

Example 21. The robotic surgical system of any one of Example 19 through Example 20, wherein the first condition is tissue thickness located at the end effector and the control circuit is configured to: receive tissue thickness from a gap sensor located in the end effector; and set the command velocity of the first motor to a third velocity in sections of the end effector where the tissue thickness is greater than a threshold thickness, and wherein the third velocity is less than the second velocity.

Example 22. The robotic surgical system of any one of Example 19 through Example 21, wherein the first condition is closure force applied to the end effector and the control circuit is configured to: receive closure force from a sensor coupled to an output shaft of the second motor; and set the command velocity of the first motor to a third velocity in sections of the end effector where the closure force is greater than a threshold force, and wherein the third velocity is less than the second velocity.

Example 23. The robotic surgical system of any one of Example 19 through Example 22, wherein the first condition is firing force to displace the displacement member and the control circuit is configured to: receive firing force from a sensor coupled to the output shaft of the first motor; and set the command velocity of the first motor to a third velocity in sections of the end effector where the closure force is greater than a threshold force, and wherein the third velocity is less than the second velocity.

Example 24. The robotic surgical system of any one of Example 19 through Example 23, wherein the first condition is tissue impedance at the end effector and the control circuit is configured to: receive tissue impedance from a sensor located in the end effector; and set the command velocity of the first motor to a third velocity in sections of the end effector where the impedance is greater than a threshold impedance, and wherein the third velocity is less than the second velocity.

Example 25. The robotic surgical system of any one of Example 19 through Example 24, wherein the first condition is tissue coverage in segmented sections of the end effector and the control circuit is configured to: receive tissue presence from a sensor located in a section in a section of the end effector; set the command velocity of the first motor to a first velocity in sections of the end effector where there is no tissue; and set the command of the first motor to a second velocity in sections of the end effector where the tissue is located in the end effector; wherein the second velocity is less than the first velocity.

Example 26. The robotic surgical system of any one of Example 19 through Example 25, wherein the first condition is tissue thickness located at the end effector and the control circuit is configured to: receive tissue thickness from a gap sensor located in the end effector; and set the command velocity of the first motor to a third velocity in sections of the end effector where the tissue thickness is greater than a threshold thickness, and wherein the third velocity is less than the second velocity.

Example 27. The robotic surgical system of any one of Example 19 through Example 26, wherein the first condition is closure force applied to the end effector and the control circuit is configured to: receive closure force from a sensor coupled to an output shaft of the second motor; and set the command velocity of the first motor to a third velocity in sections of the end effector where the closure force is greater than a threshold force, and wherein the third velocity is less than the second velocity.

Example 28. The robotic surgical system of any one of Example 19 through Example 27, wherein the first condition is firing force to displace the displacement member and the control circuit is configured to: receive firing force from a sensor coupled to the output shaft of the first motor; and set the command velocity of the first motor to a third velocity in sections of the end effector where the closure force is greater than a threshold force, and wherein the third velocity is less than the second velocity.

Example 29. The robotic surgical system of any one of Example 19 through Example 28, wherein the first condition is tissue impedance at the end effector and the control circuit is configured to: receive tissue impedance from a sensor located in the end effector; and set the command velocity of the first motor to a third velocity in sections of the end effector where the impedance is greater than a threshold impedance, and wherein the third velocity is less than the second velocity.

Closed Loop Velocity Control of Closure Member for Robotic Surgical Instrument

In use of a motorized robotic surgical stapling system, the force on the closure member drops precipitously from the moment the firing member couples into the clamp arm and the closure force is transferred from the closure member to the firing member. Therefore, the present disclosure provides a closed loop feedback control system configured to advance the closure member during the firing stroke while the firing member is advancing distally. The present disclosure also provides individually controllable closure and firing members configured to couple to a robotic surgical instrument interface.

In one aspect, the present disclosure provides various techniques for adaptive control of the closure member velocity. In one aspect, the present disclosure provides techniques for adaptive control of the closure member velocity which measures at least two parameters of a robotic shaft. The parameters associated with the robotic shaft include, without limitation, firing member stroke location, firing member load, knife advancement velocity, closure tube stroke location, closure tube load, among others, through a detachable robotic interface unit and a removable cartridge along with circuitry disposed in the robotic interface and the cartridge that can either identify themselves and their status or provide parameters or a control program for actuating the device or end effector and recording its usage.

In one aspect, the force on the closure tube force drops precipitously from the moment the I-beam couples into the anvil and begins to take a load. This may be overcome by advancing the closure tube wile the firing member is advancing distally. In one aspect, a robotic interface provides individually closed loop controllable closure tube and firing member. These closed loop control techniques are described hereinbelow.

Figure 34:
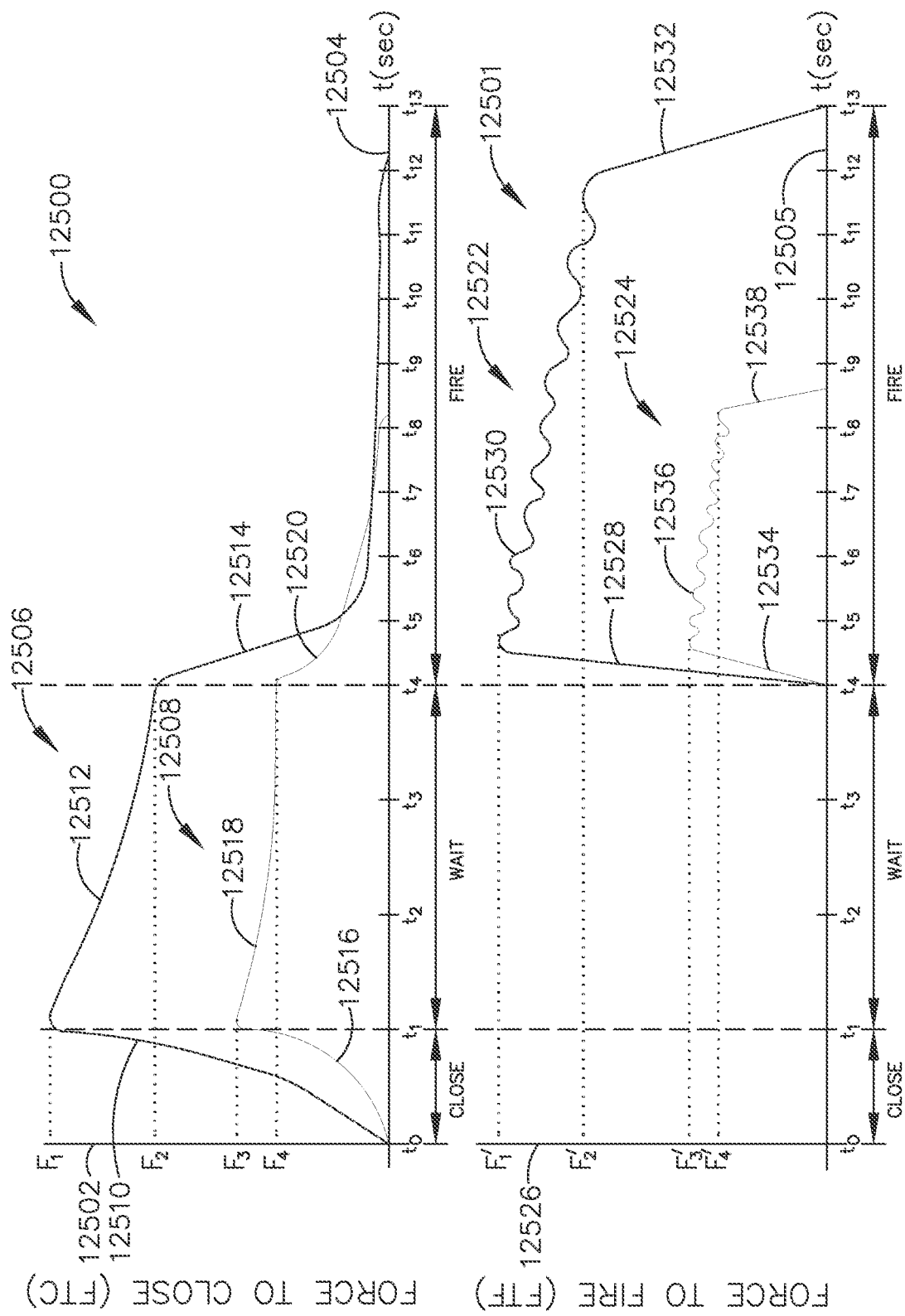
FIG. 34 is a first graph of two closure force (FTC) plots depicting the force applied to a closure member to close on thick and thin tissue during a closure phase and a second graph of two firing force (FTF) plots depicting the force applied to a firing member to fire through thick and thin tissue during a firing phase.

Prior to turning to a description of closed loop control techniques of the closure tube and firing member, the description turns briefly to FIG. 34. FIG. 34 is a graph 12500 depicting two closure force (FTC) plots 12506, 12508 depicting the force applied to a closure member to close on thick and thin tissue during a closure phase and a graph 12501 depicting two firing force (FTF) plots 12522, 12524 depicting the force applied to a firing member to fire through thick and thin tissue during a firing phase. Referring to FIGS. 30 and 34, the graph 12500 depicts an example of the force applied to thick and thin tissue during a closure stroke to close the end effector 2502 relative to tissue grasped between the anvil 2516 and the staple cartridge 2518, where the closure force is plotted as a function of time. The closure force plots 12506, 12508 are plotted on two axes. A vertical axis 12502 indicates the closure force (FTC) the end effector 2502 in newtons (N). A horizontal axis 12504 indicates time in seconds and labeled $t_0$ to $t_{13}$ for clarity of description. The first closure force plot 12506 is an example of the force applied to thick tissue during a closure stroke to close the end effector 2502 relative to tissue grasped between the anvil 2516 and the staple cartridge 2518 and a second plot 12508 is an example of the force applied to thin tissue during a closure stroke to close the end effector 2502 relative to tissue grasped between the anvil 2516 and the staple cartridge 2518. The first and second closure force plots 12506, 12508 are divided into three phases, a close stroke (CLOSE), a waiting period (WAIT), and a firing stroke (FIRE). During the closure stroke, the closure tube 1040, 1042 (FIGS. 4 and 6-10) is translated distally (direction "DD") to move the anvil 2516, for example, relative to the staple cartridge 2518 in response to the actuation of the closure stroke by the closure motor 2504b. In other instances, the closure stroke involves moving a staple cartridge 2518 relative to an anvil 2516 in response to the actuation of the closure motor 2504b and in other instances the closure stroke involves moving the staple cartridge 2518 and the anvil 2516 in response to the actuation of the closure motor 2504b. With reference to the first closure force plot 12506, during the closure stroke the closure force 12510 increases from 0 up to a maximum force $F_1$ from time $t_0$ to $t_1$. With reference to the second closure force graph 12508, during the closure stroke the closure force 12516 increases from 0 up to a maximum force $F_3$ from time $t_0$ to $t_1$. The relative difference between the maximum forces $F_1$ and $F_3$ is due to the difference in closure force necessary for thick tissue relative to thin tissue, where greater force is required to close the anvil onto thick tissue versus thin tissue.

The first and second closure force plots 12506, 12508 indicate that the closure force in the end effector 2502 increases during an initial clamping time period ending at a time ($t_1$). The closure force reaches a maximum force ($F_1$, $F_3$) at the time ($t_1$). The initial clamping time period can be about one second, for example. A waiting period can be applied prior to initiating a firing stroke. The waiting period allows fluid egress from tissue compressed by the end effector 2502, which reduces the thickness of the compressed tissue yielding a smaller gap between the anvil 2516 and the staple cartridge 2518 and a reduced closure force at the end of the waiting period. With reference to the first closure force plot 12506, there is a nominal drop in closure force 12512 from $F_1$ to $F_2$ during the waiting period between $t_1$ to $t_4$. Similarly, with reference to the second closure force plot 12508, the closure force 12518 drops nominally from $F_3$ to $F_4$ during the waiting period between $t_1$ to $t_4$. In some examples, a waiting period ($t_1$ to $t_4$) selected from a range of about 10 seconds to about 20 seconds is typically employed. In the example first and second closure force plots 12506, 12508, a period of time of about 15 seconds is employed. The waiting period is followed by the firing stroke, which typically lasts a period of time selected from a range of about 3 seconds, for example, to about 5 seconds, for example. The closure force decreases as the I-beam 2514 is advanced relative to the end effector through the firing stroke. As indicated by the closure force 12514, 12520 of the first and second closure force plots 12506, 12508, respectively, the closure force 12514, 12520 exerted on the closure tube 1040, 1042 drops precipitously from about time $t_4$ to about time $t_5$. Time $t_4$ represents the moment where the I-beam 2514 couples into the anvil 2516 and begins to take over the closing load. Accordingly, the closure force decreases as the firing force increases as shown by the first and second firing force plots 12522, 12524.

FIG. 34 also depicts a graph 12501 of first and second firing force plots 12522, 12524 that plot the force applied to advance the I-beam 2514 during the firing stroke of the surgical instrument 2500. The firing force plots 12522, 12524 are plotted on two axes. A vertical axis 12526 indicates the firing force, in newtons (N), applied to advance the I-beam 2514 during the firing stroke. The I-beam 2514 is configured to advance a knife or cutting element and motivate drivers to deploy staples during the firing stroke. A horizontal axis 12505 indicates the time in seconds on the same time scale as the horizontal axis 12504 of the upper graph 12500.

As previously described, the closure tube force drops precipitously from time $t_4$ to about time $t_5$, which represents the moment the I-beam 2514 couples into the anvil 2516 and begins to take load and the closure force decreases as the firing force increases as shown by the first and second firing force plots 12522, 12524. As the I-beam 2514 is advanced from the stroke begin position at time $t_4$ to the stroke end positions between $t_8$ and $t_9$ for the firing force plot 12524 for thin tissue and at $t_{13}$ for the firing force plot 12522 for thick tissue. As the I-beam 2514 is advanced distally during the firing stroke, the closure assembly surrenders control of the staple cartridge 2518 and the anvil 2516 to the firing assembly, which causes the firing force to increase and the closure force to decrease.

In the thick tissue firing force plot 12522, during the firing period (FIRE) the plot 12522 is divided into three distinct segments. A first segment 12528 indicates the firing force as it increases from 0 at $t_4$ to a peak force $F'_1$ just prior to $t_5$. The first segment 12528 is the firing force during the initial phase of the firing stroke where the I-beam 2514 advances distally from the top of the closure ramp until the I-beam 2514 contacts tissue. A second segment 12530 indicates the firing force during a second phase of the firing stroke where the I-beam 2514 is advancing distally deploying staples and cutting the tissue. During the second phase of the firing stroke the firing force drops from $F'_1$ to $F'_2$ at about $t_{12}$. A third segment 12532 indicates the firing force during the third and final phase of the firing stroke where the I-beam 2514 leaves the tissue and advances to the end of stroke in a tissue free zone. During the third phase of the firing stroke the firing force drops to from $F'_2$ to zero (0) at about $t_{13}$ where the I-beam 2514 reaches the end of stroke. In summary, during the firing stroke, the firing force rises dramatically as the I-beam 2514 enters a tissue zone, decrease steadily in the tissue zone during the stapling and cutting operation, and drops dramatically as the I-beam 2514 exits the tissue zone and enters a tissue free zone at the end of stroke.

The thin tissue firing force plot 12524 follows a similar pattern as the thick tissue firing force plot 12522. Thus, during the first phase of the firing stroke the firing force 12534 increases dramatically from 0 to $F'_3$ at about $t_5$. During the second phase of the firing stroke, the firing force 12536 drops steadily from $F'_3$ to $F'_4$ at about $t_8$. During the final phase of the firing stroke the firing force 12532 drops dramatically from $F'_4$ to 0 between $t_8$ and $t_9$.

To overcome the precipitous drop in closure force from time $t_4$ to about time $t_5$, which represents the moment the I-beam 2514 couples into the anvil 2516 and begins to take load and the closure force decreases as the firing force increases, as shown by the first and second firing force plots 12522, 12524, the closure tube 1040, 1042 (FIGS. 4 and 6-10) may be advanced distally while the firing member such as the I-beam 2514 is advancing distally. Referring to FIG. 30, the closure tube 1040, 1042 is represented as the transmission element 2506b that applies a closure force to the anvil 2516. As described herein, the control circuit 2510 applies motor set points to the motor control 2508b which applies a motor control signal to the motor 2504b to drive the transmission element 2506b and advance the closure tube distally to apply a closing force to the anvil 2516. A torque sensor 2544b coupled to the output shaft of the motor 2504b can be used to measure the force applied to the closure tube 1040, 1042. In other aspects, the closure force can be measured with a strain gauge, load cell, or other suitable force sensor.

Figure 35:
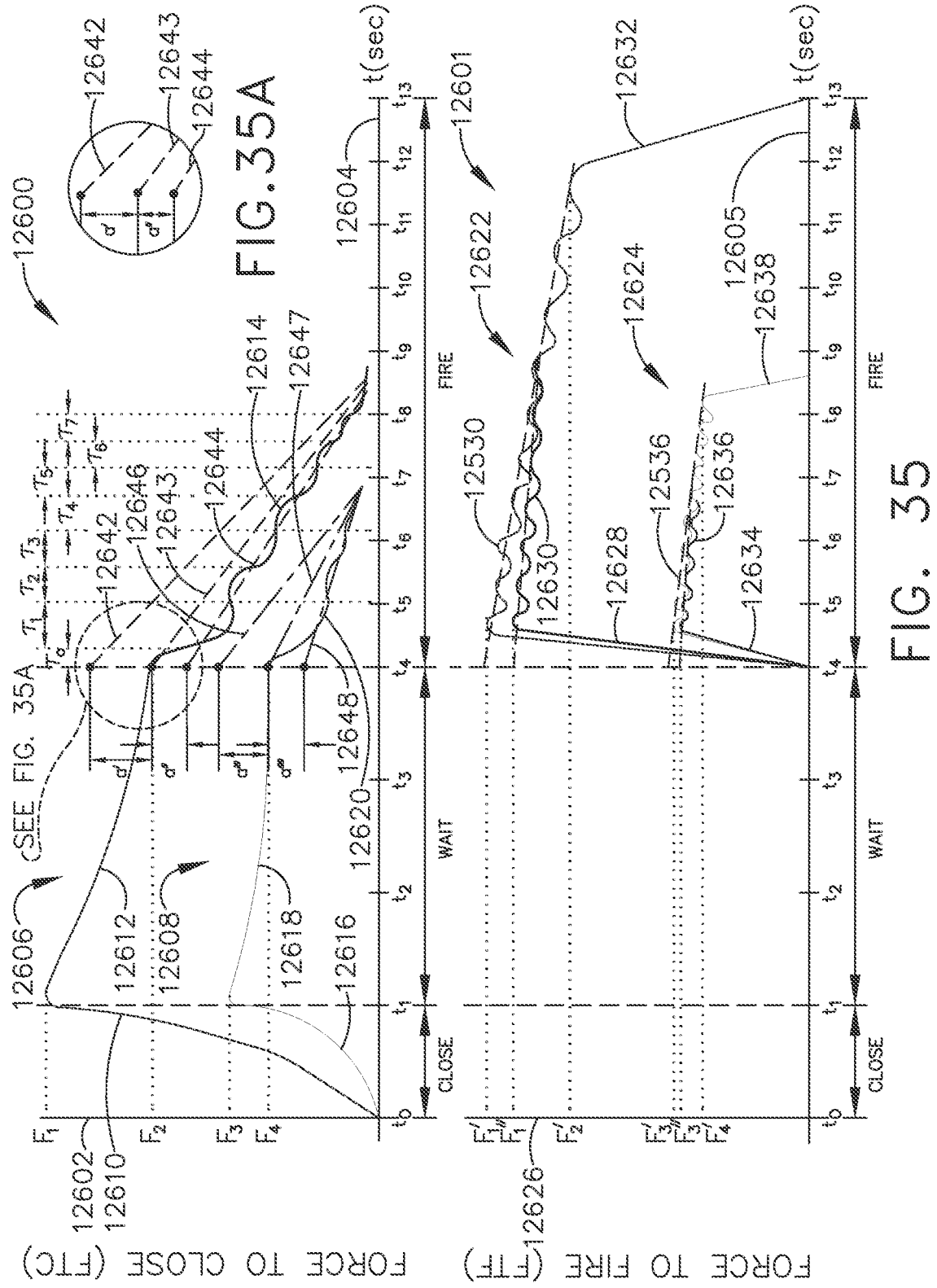
FIG. 35 is a first graph of two closure force plots depicting the force applied to a closure member to close on thick and thin tissue and a second graph of two firing force plots depicting the force applied to a firing member to fire through thick and thin tissue during a simultaneous closure and firing phase according to one aspect of this disclosure.

With continued reference to FIG. 30 and turning now to FIG. 35, there is shown a graph 12600 of two closure force plots 12606, 12608 depicting the force applied to a closure member to close on thick and thin tissue and a graph 12601 of two firing force plots 12622, 12624 depicting the force applied to a firing member to fire through thick and thin tissue during a simultaneous closure and firing phase according to one aspect of this disclosure. Referring to FIG. 35, the graph 12600 depicts an example of the force applied to thick and thin tissue during a simultaneous closure and firing stroke. Accordingly, the anvil 2516 closes on the staple cartridge 2518 while the I-beam 2514 advances distally. This action overcomes the precipitous drop in closure force from time $t_4$ to about time $t_5$, which represents the moment the I-beam 2514 couples into the anvil 2516 and begins to take load and the closure force decreases as the firing force increases, as shown by the first and second firing force plots 12522, 12524 in FIG. 34. In contrast, FIG. 35 shows that the closure force decreases over longer period leading to a more gradual drop in closure force.

The closure force plots 12606, 12608 are plotted on two axes. A vertical axis 12602 indicates the closure force the end effector 2502 in newtons (N). A horizontal axis 12604 indicates time in seconds and labeled $t_0$ to to for clarity of description. The first closure force plot 12506 is an example of the force applied to thick tissue during a closure stroke to close the end effector 2502 relative to tissue grasped between the anvil 2516 and the staple cartridge 2518 and a second plot 12608 is an example of the force applied to thin tissue during a closure stroke to close the end effector 2502 relative to tissue grasped between the anvil 2516 and the staple cartridge 2518. The first and second closure force plots 12606, 12608 are divided into three phases, a close stroke (CLOSE), a waiting period (WAIT), and a firing stroke (FIRE). During the closure stroke, the closure tube 1040, 1042 (FIGS. 4 and 6-10) is translated distally (direction "DD") to move the anvil 2516, for example, relative to the staple cartridge 2518 in response to the actuation of the closure stroke by the closure motor 2504b. In other instances, the closure stroke involves moving a staple cartridge 2518 relative to an anvil 2516 in response to the actuation of the closure motor 2504b and in other instances the closure stroke involves moving the staple cartridge 2518 and the anvil 2516 in response to the actuation of the closure motor 2504b. With reference to the first closure force plot 12606, during the closure stroke, the closure force 12610 increases from 0 up to a maximum force $F_1$ from time $t_0$ to $t_1$. Similarly, with reference to the second closure force plot 1260, during the closure stroke, the closure force 12616 increases from 0 up to a maximum force $F_3$ from time $t_0$ to $t_1$. The relative difference between the maximum forces $F_1$ and $F_3$ is due to the difference in closure force for thick tissue relative to thin tissue, where greater force is required to close the anvil onto thick tissue rather than thin tissue.

The first and second closure force graphs 12606, 12608 indicate that the closure force in the end effector 2502 increases during an initial clamping time period ending at a time $(t_1)$. The closure force reaches a maximum force $(F_1, F_3)$ at the time $(t_1)$. The initial clamping time period can be about one second, for example. A waiting period can be applied prior to initiating a firing stroke. The waiting period allows fluid egress from tissue compressed by the end effector 2502, which reduces the thickness of the compressed tissue yielding a smaller gap between the anvil 2516 and the staple cartridge 2518 and a reduced closure force at the end of the waiting period. With reference to the first closure force plot 12606, there is a nominal drop in closure force 12612 from $F_1$ to $F_2$ during the waiting period between $t_1$ to $t_4$. Similarly, with reference to the second closure force plot 12608, there is a nominal drop in the closure force 12618 from $F_3$ to $F_4$ during the waiting period between $t_1$ to $t_4$. In some examples, a waiting period ($t_1$ to $t_4$) selected from a range of about 10 seconds to about 20 seconds is typically employed. In the example first and second closure force plots 12606, 12608, a period of time of about 15 seconds is employed. The waiting period is followed by the firing stroke, which typically lasts a period of time selected from a range of about 3 seconds, for example, to about 5 seconds, for example. At time $t_4$, however, the closure member (e.g., the closure tube 1040, 10402) is advanced simultaneously with the firing member (e.g., the I-beam 2514). By simultaneously advancing the closure tube 1040, 1042 and the I-beam 2514, the closure force 12614, 12620 decreases gradually through the firing stroke as shown in the first and second closure force plots 12606, 12608, respectively.

FIG. 35 also depicts a graph 12601 of first and second firing force plots 12622, 12624 that plot the force applied to advance the I-beam 2514 during the firing stroke while advancing the closure tube 1040, 1042 during a portion of the firing stroke of the surgical instrument 2500. The firing force plots 12622, 12624 are plotted on two axes. A vertical axis 12626 indicates the firing force, in newtons (N), applied to advance the I-beam 2514 during the firing stroke. The !-beam 2514 is configured to advance a knife or cutting element and motivate drivers to deploy staples during the firing stroke. A horizontal axis 12605 indicates the time in seconds on the same scale as the horizontal axis 12604 of the upper graph 12600. As previously described, the force exerted on the closure tube drops gradually from time $t_4$ to about time $t_9$ for thick tissue as indicated by the closure force 12614 and from time $t_4$ to about $t_7$ as indicated by the closure force 12620 for thin tissue.

In the thick tissue firing force plot 12622, during the firing period (FIRE) the plot 12622 the firing force 12628 increases from 0 at $t_4$ to a peak force $F''_1$ just prior to $t_5$, which is slightly lower than the peak force $F'_1$ shown in FIG. 34. The firing force 12628 occurs during the initial phase of the firing stroke where the I-beam 2514 advances distally from the top of the closure ramp while the closure tube 1040, 1042 starts advancing distally until the I-beam 2514 contacts tissue. The firing force 12630 during a second phase of the firing stroke occurs while the I-beam 2514 advances distally deploying staples and cutting tissue. During the second phase of the firing stroke, the firing force 12630 drops from a force of $F''_1$ at just before $t_5$ to a force of $F'_2$ at about $t_{12}$. However, the firing force plot 12622 is slightly lower than the firing force plot 12522 shown in FIG. 34 during a portion of the firing stroke. The firing force 12632 during the third and final phase of the firing stroke occurs when the I-beam 2514 leaves the tissue zone and advances to the end of stroke in a tissue free zone. During the third phase of the firing stroke the firing force 12632 drops from $F'_2$ to zero (0) at about $t_{13}$ and represents the point where the !-beam 2514 reaches the end of stroke. In summary, during the firing stroke, the firing force 12628, 12634 rises dramatically as the I-beam 2514 enters a tissue zone, the firing force 12630, 12636 decrease steadily in the tissue zone during the stapling and cutting operation, and the firing force 12632, 12638 drops dramatically as the I-beam 2514 exits the tissue zone and enters a tissue free zone at the end of stroke. During the phase where the closure tube 1040, 1042 and the I-beam 2514 are advanced distally at the same time, the firing force $F''_1$ and $F''3$ is slightly lower relative to the firing force $F'_1$ and $F'_3$ shown in FIG. 34.

The closure force 12614, 12620 and firing force 12630, 12636 shown in the diagrams 12600, 12601 illustrate the effects on firing force load exerted on the firing rack (lower graph 12601) and the closure force load exerted on the closure tube (upper graph 12600) when the closure tube is advanced and load controlled during at least a portion of the firing stroke as shown by the initial value of the threshold limits a, a', a" about in the upper graph 12600 for the thick tissue plot 12606 and magnified in FIG. 35A are represented by upper limit closure force threshold 12642, a lower limit closure force threshold 12644, and a nominal closure force 12643 between the upper and lower limit closure force thresholds 12642, 12644. Similar threshold limits apply for the thin tissue plot 12608 as shown by upper limit 12646, lower limit 12648, and nominal 12647. A nested PID feedback control system monitors the closure force exerted on the closure tube 1040, 1042 and controls the velocity of the closure tube 1040, 1042 to maintain the closure force between the thresholds 12642, 12644, for thick tissue, and thresholds 12646, 12648, for thin tissue. For example, with the closure tube 1040, 1042 stopped, from time $t_4$ over period $\tau_0$, the closure force 12614 drops below the lower limit closure force threshold 12644. At this time the controller 2510 starts advancing the closure tube 1040, 1042 at a predetermined velocity. Under nested PID feedback control, the control circuit 2510 measures the force exerted on the closure tube 1040, 1042 and adjusts the set point velocity of the closure tube 1040, 1042 based on the actual velocity and the force exerted on the closure tube 1040, 1042. Accordingly, as the closure tube 1040, 1042 starts to advance distally the closure force starts to increase over the next period $\tau_1$, until it overshoots the lower threshold 12644', at which point the control circuit 2510 stops the closure tube 1040, 1042, and over the next period $\tau_2$, the closure force starts to drop again until it drops below and undershoots the lower limit closure force threshold 12644, at which point the control circuit 2510 once again starts advancing the closure tube 1040, 1042 distally. This process is repeated until the closure force drops to zero at time between $t_8$ and $t_9$. A similar process applies to the closure force for thin tissue closure force 12620. The PID controlled feedback system is explained herein in more detail in connection with FIGS. 36-40. The upper and lower limit closure force thresholds 12642, 12644, 12646, 12648 as shown in FIG. 35 vary linearly with from initial values of a', a'', a''', a'''' to about zero on a negative slope as a function of time. It will be appreciated, that the upper and lower limit closure force thresholds 12642, 12644, 12646, 12648 may be configured using non-linear expressions or custom set limits stored in memory if the form of a look-up table. Although the initial values a', a'', a''', a'''' of the upper and lower limit closure force thresholds 12642, 12644, 12646, 12648 are given at the point in time coinciding with the beginning of the firing stroke, the initial values a', a'', a''', a'''' may be given anywhere along the firing stroke.

In order to lower the closure force and firing force variables as shown in FIG. 35, the present disclosure provides an adaptive closure tube velocity control algorithm which measures at least two parameters of the robotic shaft such as, for example, firing member stroke location, firing member load, knife advancement speed, closure tube stroke location, and/or closure tube load, through a detachable interface and a removable cartridge. The removable cartridge may further include circuits being configured to either identify themselves and their status or provide parameters or a control program for actuating the device or end-effector and recording its usage. In one aspect, the velocity of the closure tube 1040, 1042 may be controlled by a nested proportional-integral-derivative controller (PID controller) to provide progressive closure of the closure tube 1040, 1042 (e.g., closure member) from time $t_4$ when the I-beam 2514 (e.g., firing member) advances distally and couples into the anvil 2516 to lower the closure force load on the closure tube 1040, 1042 at a desired rate and decrease the firing force load on the I-beam 2514.

Figure 36:
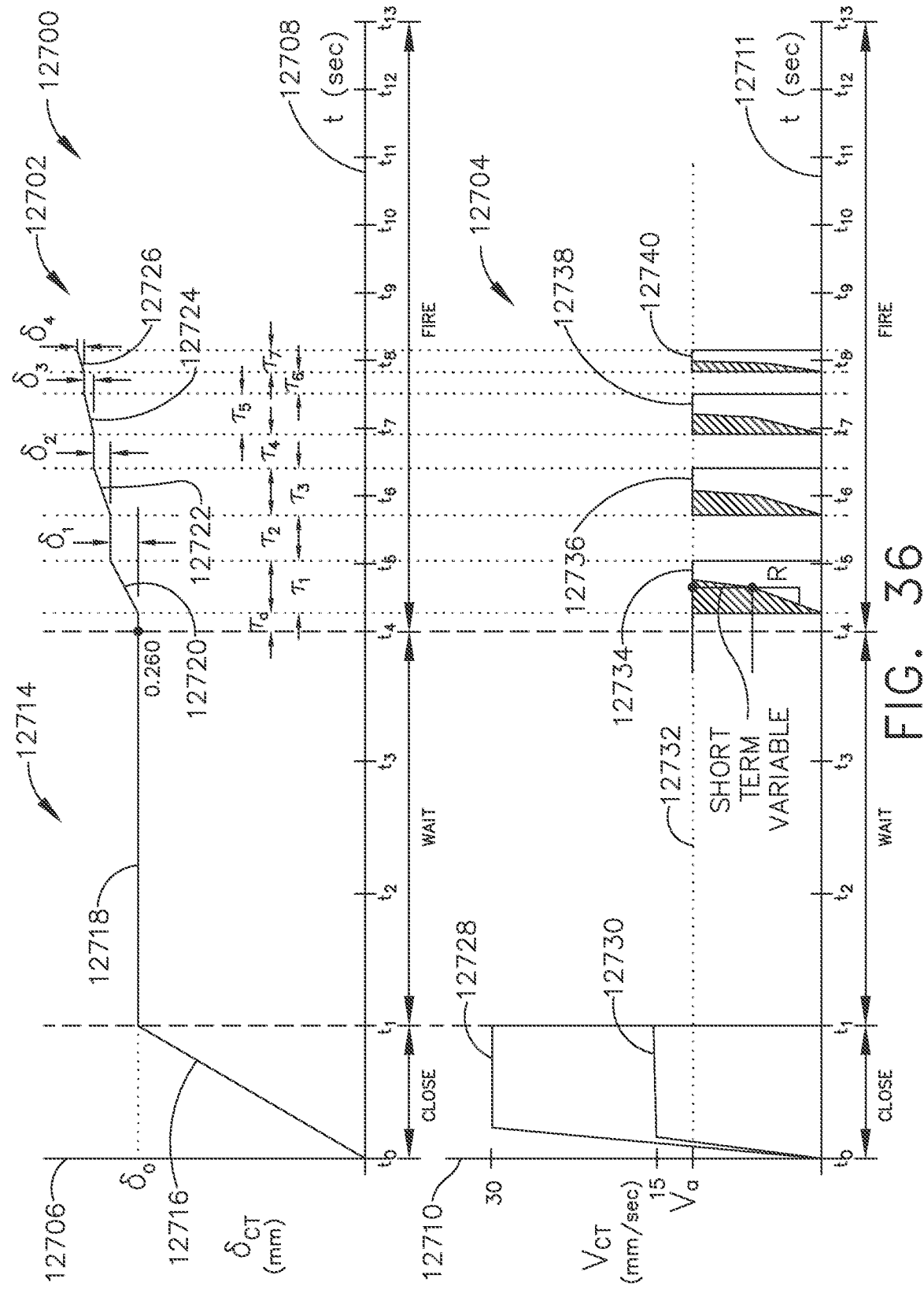
FIG. 36 is a graph of a control process for thick tissue to control closure member velocity based on the closure force load on a closure member and actual velocity of the closure member according to one aspect of this disclosure.

FIG. 36 illustrates a graph 12700 of a PID control algorithm for thick tissue to control closure tube velocity based on the closure force load on a closure tube and actual velocity of the closure tube according to one aspect of this disclosure. The nested PID control algorithm may be implemented by the control circuit 2510 shown in FIG. 30. The control circuit 2510 is configured to measure at least two parameters of the robotic shaft such as, for example, firing member stroke location, firing member load, knife advancement speed, closure tube stroke location, and/or closure tube load. The upper graph 12702 is a plot depicting displacement of the closure tube $\delta_{CT}$ (mm) along the vertical axis 12706 and time "t" (sec) along the horizontal axis 12708. The lower graph 12704 is a plot depicting velocity of the closure tube $V_{CT}$ (mm/sec) along the vertical axis 12710 and time "t" (sec) along the horizontal axis 12711. The upper and lower diagrams 12702, 12704 are divided into three phase, a close stroke (CLOSE), a waiting period (WAIT), and a firing stroke (FIRE), as shown in FIGS. 34 and 35 on the same time scale along the horizontal axes 12708, 12711, 12604, 12605, 12504, 12505. During the closure stroke (CLOSE), the closure tube 1040, 1042 (FIGS. 4 and 6-10) is translated distally to move the anvil 2516, for example, relative to the staple cartridge 2518 in response to the actuation of the closure stroke by the closure motor 2504b. Under normal operation, the velocity curve 12728 corresponds to the velocity of the closure tube 1040, 1042 for the load plots shown in FIG. 34. Under nested PID control, the closure tube velocity 12730 is much lower than the standard closure tube velocity 12728.

With reference to the upper and lower diagrams 12702, 12704, during the closure phase (CLOSE) between $t_0$ and $t_1$, the velocity of the closure tube 1040, 1042 increases as shown by velocity curve 12730 profile causing the closure tube 1040, 1042 to advance distally as shown by displacement 12716 to $\delta_0$. In one example, the displacement at $t_1$ $\delta_0$ is −5.08 mm (0.200"). The end of the closure phase is marked by $t_1$, which is when the instrument enters the waiting period (WAIT) and the velocity of the closure tube 1040, 1042 goes to zero during the period from time $t_1$ to time $t_4$. In other words, the closure tube 1040, 1042 stops advancing distally. During the waiting period, the closure tube 1040, 1042 displacement is zero as shown by displacement 12718. Under nested PID control, the velocity of the closure tube 1040, 1042 is adaptively controlled to provide progressive advancement of the closure tube 1040, 1042 during at least a portion of the firing phase (FIRE). The PID controller sets a target velocity of the closure tube 1040, 1042 and monitors the force exerted on the closure tube 1040, 1042 during the displacement period and adjusts the velocity $V_{CT}$ of the closure tube 1040, 1042 based on the target velocity and the force exerted on the closure tube 1040, 1042 in a nested control system configuration.

Figure 37:
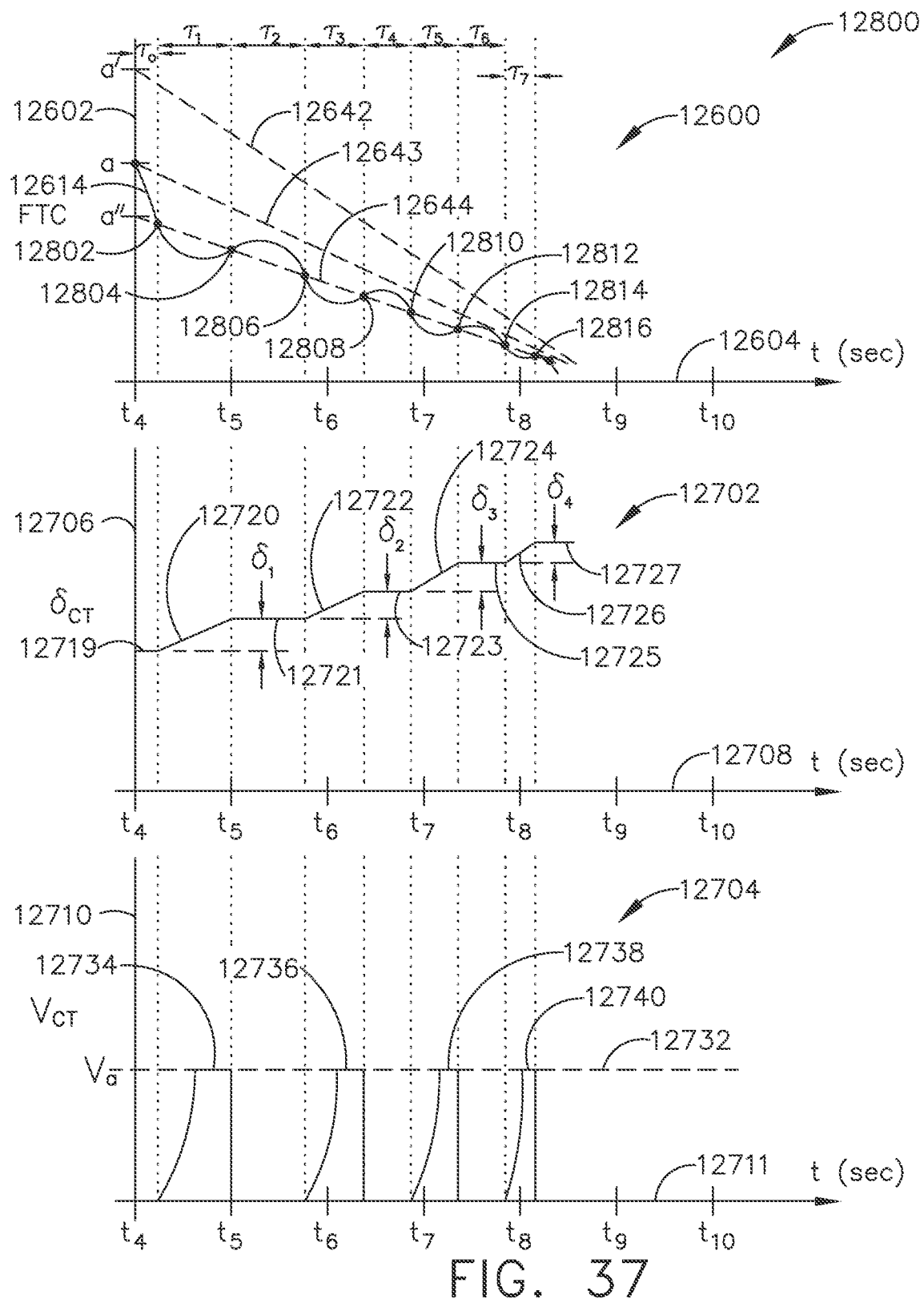
FIG. 37 is a detail view of the closure force, displacement, and closed loop feedback controlled closure tube velocity during a firing stroke according to one aspect of this disclosure.

With reference now to FIGS. 30, 36, and 37, the control circuit 2510, configured as a nested PID feedback controller, monitors the closure force 12614 acting on the closure tube 1040, 1042 and the actual velocity of the closure tube 1040, 1042 and progressively controls the closure tube 1040, 1042 advancement based on the measured closure force 12614 and the actual velocity of the closure tube 1040, 1042. This process begins at time $t_4$, where the velocity of the closure tube 1040, 1042 is zero and the closure force 12614 drops from point 12801, which is the mid-point of the thresholds 12642, 12644, to point 12802 over period $\tau_0$. During the period $\tau_0$, the closure tube 1040, 1042 is stationary and the displacement remains at $\delta_0$.

As the closure force 12614 drops below the lower threshold 12644, the feedback control system (e.g., the control circuit 2510) sets a command velocity to the closure motor 2504b and the firing motor 2508a to start the firing phase. It will be appreciated that the closure force the closure tube 1040, 1042 may be obtained from the torque sensor 2544b coupled to the output shaft of the closure motor 2504b. Likewise, the firing force the I-beam 2514 may be obtained from the torque sensor 2544a coupled to the output shaft of the firing motor 2504a. In other aspects, the closure force and firing force may be measured with strain gauges, load cells, or other suitable force sensors for example. Accordingly, the closure tube 1040, 1042 and the I-beam 2514 start to advance. The velocity 12734 of the closure tube 1040, 1042 ramps up to a maximum velocity 12732 over period $\tau_1$. As the closure tube 1040, 1042 advances distally, the displacement 12720 starts to ramp up from $\delta_0$ 12719 over the period Ti. Also, as the closure tube 1040, 1042 advances distally, closure force 12614 experienced by the closure tube 1040, 1042 begins to increase until it crosses the lower threshold 12644 at point 12804. At this point, the control circuit 2510 sets the closure motor 2504b set point to zero to stop advancing the closure tube 1040, 1042 while the firing motor 2504a continues advancing the I-beam 2514. During the period $\tau_1$, the closure tube 1040, 1042 advanced a distance of $\delta_1$.

Once the closure tube velocity is set to zero, over period $\tau_2$, the closure tube 1040, 1042 does not advance distally, the displacement 12721 remains at $(\delta_0+\delta_1)$, and the closure force 12614 decrease below the lower threshold 12644 at point 12806. The control circuit 2510 then ramps up the velocity 12736 and the closure tube 1040, 1042 displacement 12722 advances 62 over period $\tau_3$. As the closure force 12614 increases above the lower threshold 12644 at point 12808, the closure tube velocity is set to zero again. It should be noted that as the firing force continuously decreases over time, the period during which the velocity is nonzero decreases such that $\tau_3<\tau_1$. Stated otherwise, over time the nested PID feedback controller forces the closure force 12614 to converge to the threshold 12644. Over the next period $\tau_4$ the displacement 12723 remains at $(\delta_0+\delta_1+\delta_2)$ until the closure force decreases below the lower threshold 12644 at point 12810 and the control circuit 2510 starts the closure motor 2504b and increases the velocity 12738 over period $\tau_5$ to displace 12724 the closure tube 1040, 1042 by $\delta_3$ until the firing force close increases above the lower threshold 12644 at point 12812 and the closure motor 2504b is turned off. Again, the displacement periods $\tau_5<\tau_3<\tau_1$ get increasingly smaller as the closure force 12614 converges to an ideal or desired closure force value. Over the period $\tau_6$, the displacement 12725 remains at $(\delta_0+\delta_1+\delta_2+\delta_3)$ until the closure force 12614 decreases below the lower threshold 12644 at point 12814. The control circuit 2510 starts the closure motor 2504b and increases the velocity 12740 over period $\tau_6$ to displace 12726 the closure tube 1040, 1042 by 64 until the firing force close increases above the lower threshold 12644 at point 12816. Again, the period $\tau_6<\tau_5<\tau_3<\tau_1$ and control circuit 2510 stops the closure motor 2504b. Over the period $\tau_7$, the displacement 12727 remains at $(\delta_0+\delta_1+\delta_2+\delta_3+\delta_4)$. Eventually the process stops as the closure force 12614 approaches zero.

Although the process in connection with FIGS. 35-37 has been described in the context of the closure force 12614 ringing about the lower threshold 12644 until an ideal closure force is determined by the nested PID controller, a similar process may be employed when the closure force 12614 increase above the upper threshold 12642 with one exception. In regard to the process described in FIGS. 39-40, the closure tube 10410, 1042 was advanced distally when the closure force 12614 decreased below the lower threshold 12644. However, when the closure force 12614 increases above the upper threshold 12642, the closure tube 1040, 1042 is retracted proximally rather than advanced distally until the closure force 12614 decreases below the upper threshold 12642.

Figure 38:
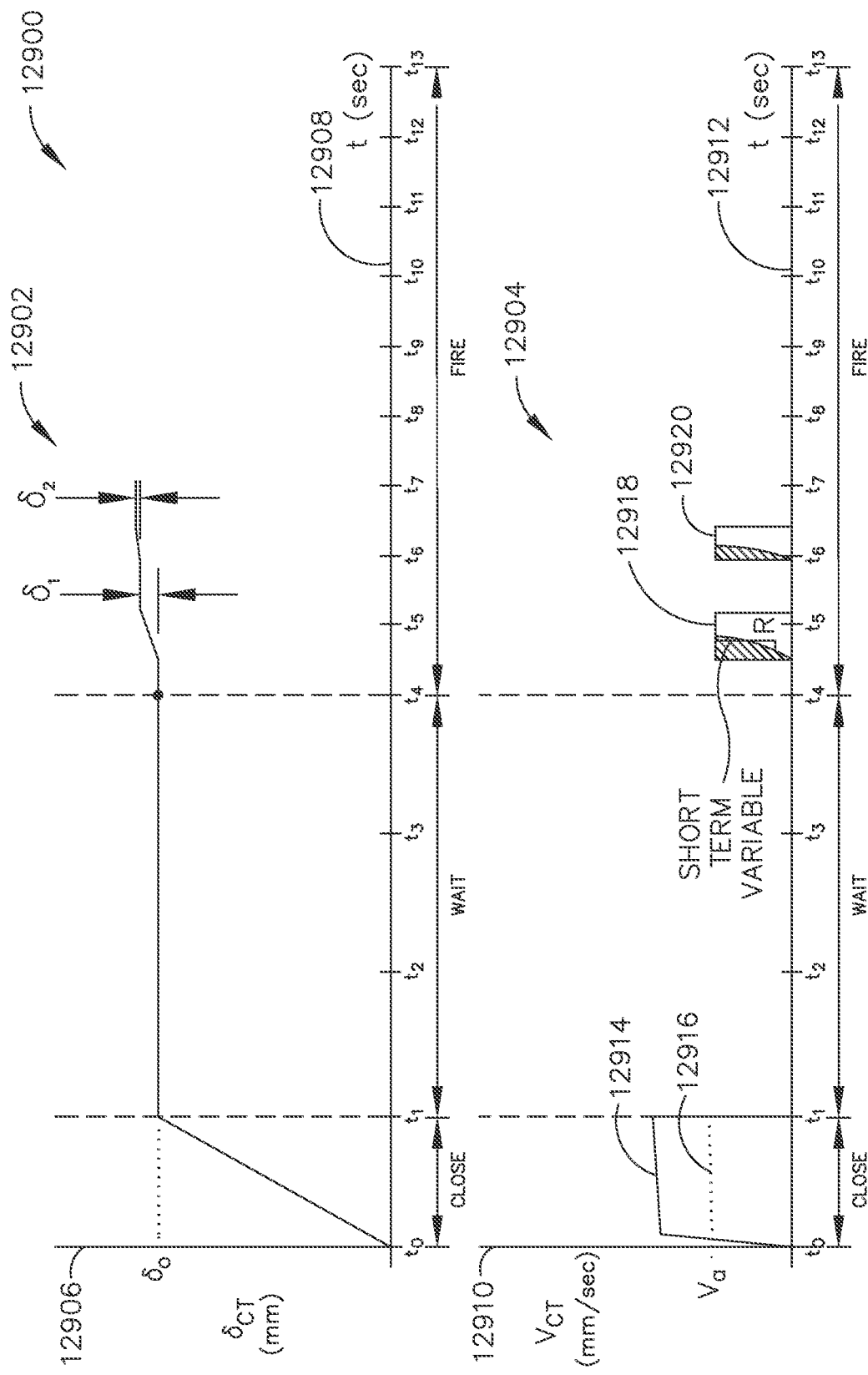
FIG. 38 illustrates a graph of a control process for thin tissue to control closure member velocity based on the closure force load on a closure member and actual velocity of the closure member according to one aspect of this disclosure.

FIG. 38 illustrates a graph 12900 of a control algorithm for thin tissue to control closure tube velocity based on the closure force load on a closure tube and actual velocity of the closure tube according to one aspect of this disclosure. In one aspect, the control algorithm may be implemented as a nested proportional-integral-derivative (PID) control algorithm by the control circuit 2510 shown in FIG. 30. The control circuit 2510 is configured to measure at least two parameters of the robotic shaft such as, for example, firing member stroke location, firing member load, knife advancement speed, closure tube stroke location, and/or closure tube load. The upper graph 12902 is a plot depicting displacement of the closure tube $\delta_{CT}$ (mm) along the vertical axis 12906 and time "t" (sec) along the horizontal axis 12908. The lower graph 12904 is a plot depicting velocity of the closure tube $V_{CT}$ (mm/sec) along the vertical axis 12910 and time "t" (sec) along the horizontal axis 12912. The upper and lower diagrams 12902, 12904 are divided into three phase, a close stroke (CLOSE), a waiting period (WAIT), and a firing stroke (FIRE), as shown in FIGS. 34-36 on the same time scale along the horizontal axes 12908, 12708, 12711, 12604, 12605, 12504, 12505. During the closure stroke (CLOSE), the closure tube 1040, 1042 (FIGS. 4 and 6-10) is translated distally to move the anvil 2516, for example, relative to the staple cartridge 2518 in response to the actuation of the closure stroke by the closure motor 2504b. Under normal operation, the velocity curve 12914 corresponds to the velocity of the closure tube 1040, 1042 for the load plots shown in FIG. 34. Under nested PID control, the closure tube velocity 12916 is much lower than the standard closure tube velocity 12914.

With reference to FIGS. 30, 36 and 38, At the beginning of the firing stroke at $t_4$, the velocity of the closure tube 1040, 1042 is zero during a first period $\tau_0$. During this period, the closure force 12620 (FIG. 36) decreases and when it drops below the lower threshold 12648, the closure motor 2504b is turned on and the closure tube velocity 12918 is ramped up by the control circuit 2510 to drive the closure tube 1040, 1042. During the following period $\tau_1$, the closure tube 1040, 1042 translates distally until the closure force 12620 increases above the lower threshold 12648 causing the control circuit to stop the closure motor 2504b. During the period $\tau_1$, the closure tube 1040, 1042 advanced distally from $\delta_0$ to $\delta_1$. The control circuit 2510 keeps the closure motor 2504b off during the period $\tau_2$ until the closure force 12620 drops below the lower threshold 12648 at which point the control circuit 2510 turns on the closure motor 2504b and drives the closure tube 1040, 1042 at velocity 12920 during the next period $\tau_3$. The closure tube 1040, 1042 translates by $\delta_2$. During the next period $\tau_4$ the closure tube 1040, 1042 does not move distally and remains at position $(\delta_0+\delta_1+\delta_2)$ until the closure force 12620 reaches a desired balance or falls below the lower threshold 12648. Although the thin tissue closure tube 1040, 1042 velocity control process was discussed in the context of the lower threshold 12648, a similar process would apply in the context of the upper threshold 12646 with one exception. When the closure force 12620 increases above the upper threshold 12646, the closure tube 1040, 1042 is retracted proximally rather than advanced distally until the closure force 12620 decreases below the upper threshold 12646.

Figure 39:
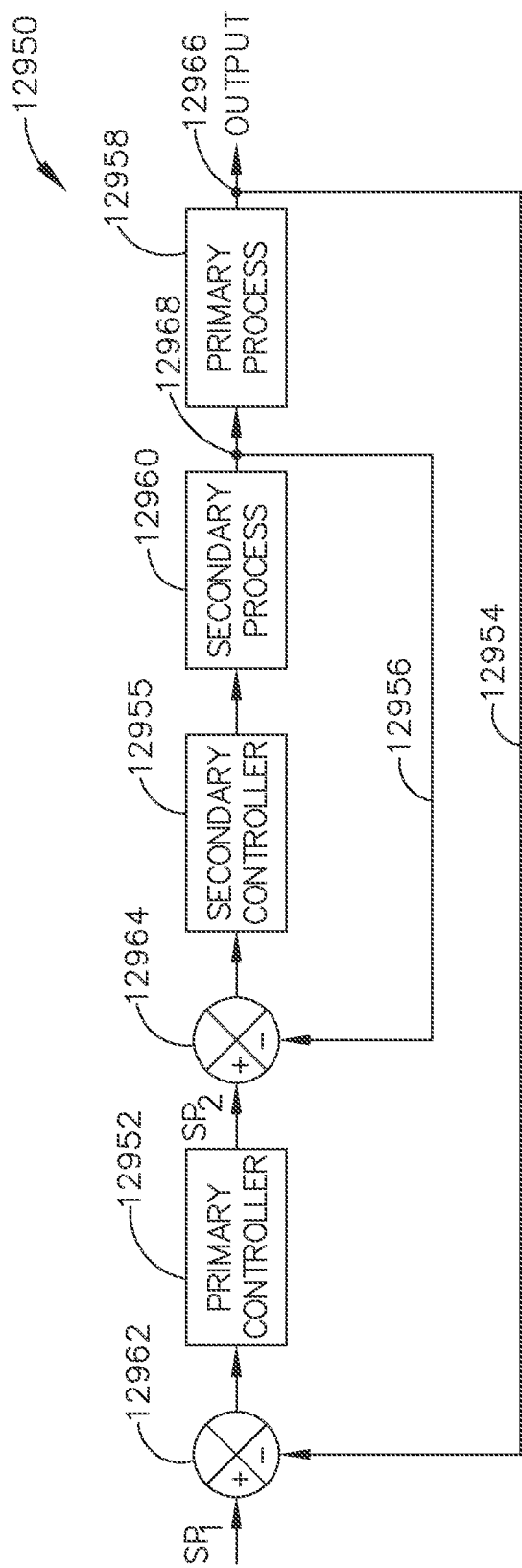
FIG. 39 is a graph of a control system configured to provide progressive closure of a closure member during a firing stroke when the firing member advances distally and couples into a clamp arm to lower the closure force load on the closure member at a desired rate and decrease the firing force load on the firing member according to one aspect of this disclosure.
Figure 40:
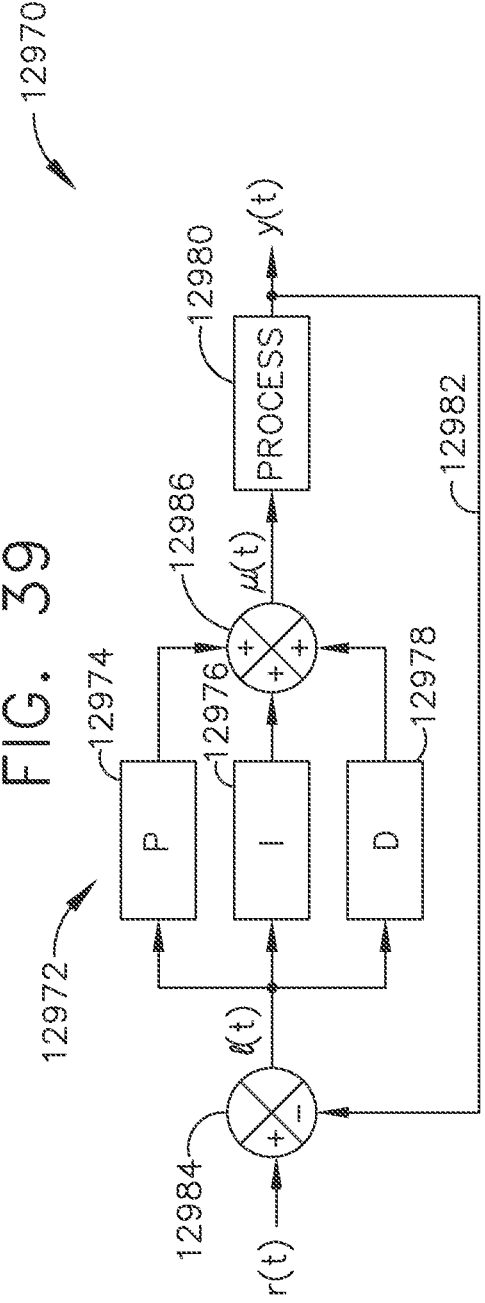
FIG. 40 illustrates a proportional-integral-derivative (PID) controller feedback control system according to one aspect of this disclosure.

FIG. 39 is a diagram of a control system 12950 configured to provide progressive closure of a closure member (e.g., closure tube 1040, 1042) when the firing member (e.g., I-beam 2514) advances distally and couples into a clamp arm (e.g., anvil 2516) to lower the closure force load on the closure member at a desired rate and decrease the firing force load on the firing member according to one aspect of this disclosure. In one aspect, the control system 12950 may be implemented as a nested PID feedback controller. A PID controller is a control loop feedback mechanism (controller) to continuously calculate an error value as the difference between a desired set point and a measured process variable and applies a correction based on proportional, integral, and derivative terms (sometimes denoted P, I, and D respectively). The nested PID controller feedback control system 12950 includes a primary controller 12952, in a primary (outer) feedback loop 12954 and a secondary controller 12955 in a secondary (inner) feedback loop 12956. The primary controller 12952 may be a PID controller 12972 as shown in FIG. 39, and the secondary controller 12955 also may be a PID controller 12972 as shown in FIG. 40. The primary controller 12952 controls a primary process 12958 and the secondary controller 12955 controls a secondary process 12960. The output 12966 of the primary process 12958 (OUTPUT) is subtracted from a primary set point $SP_1$ by a first summer 12962. The first summer 12962 produces a single sum output signal which is applied to the primary controller 12952. The output of the primary controller 12952 is the secondary set point $SP_2$. The output 12968 of the secondary process 12960 is subtracted from the secondary set point $SP_2$ by a second summer 12964.

In the context of controlling the displacement of the closure tube 1040, 1042, the control system 12950 may be configured such that the primary set point $SP_1$ is a desired closure force value and the primary controller 12952 is configured to receive the closure force 12614 from the torque sensor 2544*b* coupled to the output of the closure motor 2504*b* and determine a set point $SP_2$ motor velocity for the closure motor 2504*b*. In other aspects, the closure force 12614 may be measured with strain gauges, load cells, or other suitable force sensors. The closure motor 2504*b* velocity set point $SP_2$ is compared to the actual velocity of the closure tube 1040, 1042, which is determined by the secondary controller 12954. The actual velocity of the closure tube 1040, 1042 may be measured by comparing measuring the displacement of the closure tube 1040, 1042 with the position sensor 2534 and measuring elapsed time with the timer/counter 2531. Other techniques, such as linear or rotary encoders may be employed to measure displacement of the closure tube 1040, 1042. The output 12968 of the secondary process 12960 is the actual velocity of the closure tube 1040, 1042. This closure tube velocity output 12968 is provided to the primary process 12958 which determines the force acting on the closure tube 1040, 1042 and is fed back to the adder 12962, which subtracts the measured closure force 12614 from the primary set point $SP_1$. As described above, the primary set point $SP_1$ may be the upper threshold 12642 or the lower threshold 12644. Based on the output of the adder 12962, the primary controller 12952 controls the velocity and direction of the closure tube motor 2504*b* as described herein in connection with FIGS. 35-37. The secondary controller 12954 controls the velocity of the closure motor 2504*b* based on the actual velocity of closure tube 1040, 1042 measured by the secondary process 12960 and the secondary set point $SP_2$, which is based on a comparison of the actual firing force 12614 and the firing force upper and lower thresholds 12642, 12644.

FIG. 40 illustrates a PID feedback control system 12970 according to one aspect of this disclosure. The primary controller 12952 or the secondary controller 12954, or both, may be implemented as a PID controller 12972. In one aspect, the PID controller 12972 may comprise a proportional element 12974 (P), an integral element 12976 (I), and a derivative element 12978 (D). The outputs of the P, I, D elements 12974, 12976, 12978 are summed by a summer 12986, which provides the control variable u(t) to the process 1250. The output of the process 12950 is the process variable y(t). The summer 12984 calculates the difference between a desired set point r(t) and a measured process variable y(t). The PID controller 12972 continuously calculates an error value e(t) (e.g., difference between closure force threshold and measured closure force) as the difference between a desired set point r(t) (e.g., closure force threshold) and a measured process variable y(t) (e.g., velocity and direction of closure tube) and applies a correction based on the proportional, integral, and derivative terms calculated by the proportional element 12974 (P), integral element 12976 (I), and derivative element 12978 (D), respectively. The PID controller 12972 attempts to minimize the error e(t) over time by adjustment of the control variable u(t) (e.g., velocity and direction of the closure tube).

In accordance with the PID algorithm, the "P" element 12974 accounts for present values of the error. For example, if the error is large and positive, the control output will also be large and positive. In accordance with the present disclosure, the error term e(t) is the different between the desired closure force and the measured closure force of the closure tube. The "I" element 12976 accounts for past values of the error. For example, if the current output is not sufficiently strong, the integral of the error will accumulate over time, and the controller will respond by applying a stronger action. The "D" element 12978 accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot.

It will be appreciated that other variables and set points may be monitored and controlled in accordance with the feedback control systems 12950, 12970. For example, the adaptive closure member velocity control algorithm described herein may measure at least two of the following parameters: firing member stroke location, firing member load, displacement of cutting element, velocity of cutting element, closure tube stroke location, closure tube load, among others.

Figure 41:
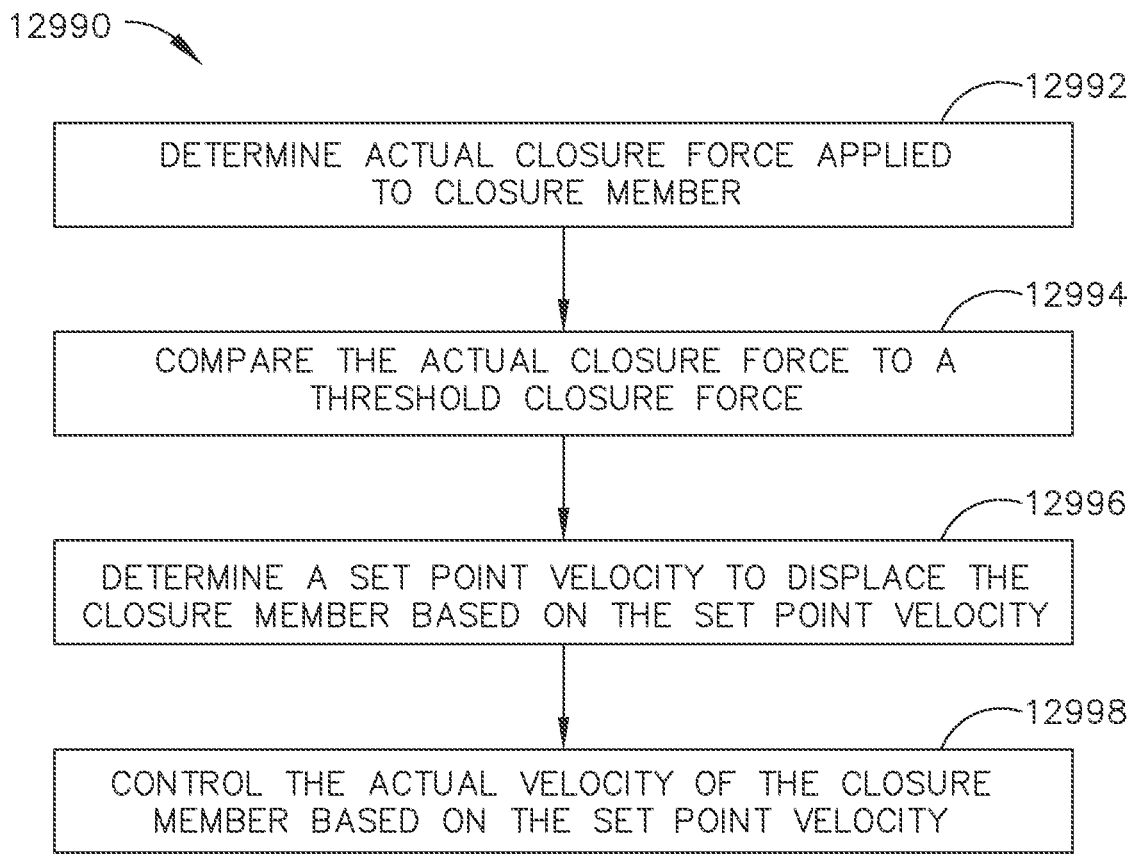
FIG. 41 is a logic flow diagram depicting a process of a control program or a logic configuration for determining the velocity of a closure member according to one aspect of this disclosure.

FIG. 41 is a logic flow diagram depicting a process 12990 of a control program or a logic configuration for determining the velocity of a closure member according to one aspect of this disclosure. With reference also to FIG. 30, a control system for a robotic surgical system comprises a control circuit 2510 configured to, according to the process 12990, the control circuit 2510 determines 12992 the actual closure force of a closure member. The control circuit 2510 compares 12994 the actual closure force to a threshold closure force and determines 12996 a set point velocity to displace the closure member based on the comparison. The control circuit 2510 controls 12998 the actual velocity of the closure member based on the set point velocity.

With reference now also to FIGS. 39 and 40, in one aspect, the control circuit 2510 comprises a proportional, integral, and derivative (PID) feedback control system 12950, 12970. The PID feedback control system 12950, 12970 comprises a primary PID feedback loop 12954 and a secondary PID feedback loop 12956. The primary feedback loop 12954 determines a first error between the actual closure force of the closure member and a threshold closure force $SP_1$ and sets the closure member velocity set point $SP_2$ based on the first error. The secondary feedback loop 12956 determines a second error between the actual velocity of the closure member and the set point velocity of the closure member an sets the closure member velocity based on the second error.

In one aspect, the threshold closure force $SP_1$ comprises an upper threshold and a lower threshold. The set point velocity $SP_2$ is configured to advance the closure member distally when the actual closure force is less than the lower threshold and the set point velocity is configured to retract the closure member proximally when the actual closure force is greater than the lower threshold. In one aspect, the set point velocity is configured to hold the closure member in place when the actual closure force is between the upper and lower thresholds.

The control system further comprises a force sensor coupled to the control circuit, the force sensor 2538 configured measure the closure force. In one aspect, the force sensor comprises a torque sensor 2544*b* coupled to an output shaft of a motor 2504*b* coupled to the closure member. In one aspect, the force sensor 2538 comprises a strain gauge coupled to the closure member. In one aspect, the force sensor comprises a load cell coupled to the closure member. In one aspect, the control system comprises a position sensor coupled to the closure member, wherein the position sensor is configured to measure the position of the closure member.

In one aspect, the control system comprises a first motor configured to couple to the closure member and the control circuit is configured to advance the closure member during at least a portion of a firing stroke.

The functions or processes 12990 described herein may be executed by any of the processing circuits described herein, such as the control circuit 961 (FIG. 22), 800 (FIG. 23), 810 (FIG. 24), 820 (FIG. 25), 4420 (FIG. 26), and/or control circuit 2510 (FIG. 30). Aspects of the motorized surgical instrument may be practiced without the specific details disclosed herein. Some aspects have been shown as block diagrams rather than detail.

Various aspects of the subject matter described herein are set out in the following examples:

Example 1. A control system for a robotic surgical system, the control system comprising: a control circuit configured to: determine actual closure force of a closure member; compare the actual closure force to a threshold closure force; determine a set point velocity to displace the closure member based on the comparison; and control the actual velocity of the closure member based on the set point velocity.

Example 2. The control system of Example 1, wherein the control circuit comprises a proportional, integral, and derivative (PID) feedback control system.

Example 3. The control system of Example 2, wherein the PID feedback control system comprises a primary PID feedback loop and a secondary PID feedback loop, wherein the primary feedback loop is configured to determine a first error between the actual closure force of the closure member and a threshold closure force and set the set point velocity based on the first error; and wherein the secondary feedback loop is configured to determine a second error between the actual velocity of the closure member and the set point velocity and control the actual velocity of the closure member based on the second error.

Example 4. The control system of one or more of Example 1 through Example 3, wherein the threshold closure force comprises an upper threshold and a lower threshold, wherein the set point velocity is configured to advance the closure member distally when the actual closure force is less than the lower threshold, and wherein the set point velocity is configured to retract the closure member proximally when the actual closure force is greater than the lower threshold.

Example 5. The control system of Example 4, wherein the set point velocity is configured to hold the closure member in place when the actual closure force is between the upper and lower thresholds.

Example 6. The control system of one or more of Example 1 through Example 5, further comprising a force sensor coupled to the control circuit, the force sensor configured measure the closure force.

Example 7. The control system of Example 6, wherein the force sensor comprises a torque sensor coupled to an output shaft of a motor coupled to the closure member, wherein the torque sensor is configured to measure the closure force.

Example 8. The control system of one or more of Example 6 through Example 7, wherein the force sensor comprises a strain gauge coupled to the closure member, wherein the strain gauge is configured to measure the closure force.

Example 9. The control system of one or more of Example 6 through Example 8, wherein the force sensor comprises a load cell coupled to the closure member, wherein the load cell is configured to measure the closure force.

Example 10. The control system of one or more of Example 6 through Example 9, further comprising a position sensor coupled to the closure member, wherein the position sensor is configured to measure the position of the closure member.

Example 11. The control system of one or more of Example 1 through Example 10, wherein the control circuit is configured to advance the closure member during at least a portion of a firing stroke.

Example 12. A control system for a robotic surgical system, the control system comprising: a first motor configured to couple to a closure member; a force sensor configured to measure closure force applied to the closure member; a closed loop feedback control system comprising a control circuit coupled to the first motor and the force sensor, wherein the control circuit is configured to: receive, from the force sensor, actual closure force the closure member; compare the actual closure force to a threshold closure force; determine a set point velocity of the first motor to displace the closure member based on the comparison; and control the actual velocity of the closure member based on the set point velocity.

Example 13. The control system of Example 12, wherein the closed loop feedback control system comprises a proportional, integral, and derivative (PID) feedback control system.

Example 14. The control system of Example 13, wherein the PID feedback control system comprises a primary PID feedback loop and a secondary PID feedback loop, wherein the primary feedback loop is configured to determine a first error between the actual closure force of the closure member and a threshold closure force and set the set point velocity based on the first error; and wherein the secondary feedback loop is configured to determine a second error between the actual velocity of the closure member and the set point velocity of the closure member and control the actual velocity of the closure member based on the second error.

Example 15. The control system of one or more of Example 12 through Example 14, wherein the threshold closure force comprises an upper threshold and a lower threshold, wherein the set point velocity is configured to advance the closure member distally when the actual closure force is less than the lower threshold, and wherein the set point velocity is configured to retract the closure member proximally when the actual closure force is greater than the lower threshold.

Example 16. The control system of Example 15, wherein the set point velocity is configured to hold the closure member in place when the actual closure force is between the upper and lower thresholds.

Example 17. The control system of one or more of Example 12 through Example 16, wherein the force sensor comprises a torque sensor coupled to an output shaft of the first motor, wherein the torque sensor is configured to measure closure force.

Example 18. The control system of one or more of Example 12 through Example 17, wherein the force sensor comprises a strain gauge coupled to the closure member, wherein the strain gauge is configured to measure closure force.

Example 19. The control system of one or more of Example 12 through Example 18, wherein the force sensor comprises a load cell coupled to the closure member, wherein the load cell is configured to measure closure force.

Example 20. The control system of one or more of Example 12 through Example 19, further comprising a position sensor coupled to the closure member, wherein the position sensor is configured to measure the position of the closure member.

Example 21. The control system of one or more of Example 12 through Example 20, further comprising a second motor coupled to a firing member, wherein the control circuit is configured to advance the closure member during at least a portion of a firing stroke of the firing member.

Example 22. A control system for a robotic surgical system, the control system comprising: a control circuit comprising a proportional, integral, and derivative (PID) feedback control system, the control circuit configured to: determine actual closure force of a closure member; compare the actual closure force to a threshold closure force; determine a set point velocity to displace the closure member based on the comparison; and control the actual velocity of the closure member based on the set point velocity; a force sensor coupled to the control circuit, the force sensor configured measure the closure force; and a motor coupled to the control circuit and to the closure member, wherein the control circuit is configured to advance the closure member during at least a portion of a firing stroke; wherein the threshold closure force comprises an upper threshold and a lower threshold, wherein the set point velocity is configured to advance the closure member distally when the actual closure force is less than the lower threshold, and wherein the set point velocity is configured to retract the closure member proximally when the actual closure force is greater than the lower threshold.

Example 23. The control system of Example 22, wherein the PID feedback control system comprises a primary PID feedback loop and a secondary PID feedback loop, wherein the primary feedback loop determines a first error between the actual closure force of the closure member and a threshold closure force and sets set point velocity based on the first error; and wherein the secondary feedback loop determines a second error between the actual velocity of the closure member and the set point velocity and controls the actual velocity of the closure member based on the second error.

Example 24. The control system of one or more of Example 22 through Example 23, wherein the set point velocity is configured to hold the closure member in place when the actual closure force is between the upper and lower thresholds.

Example 25. The control system of one or more of Example 22 through Example 24, wherein the force sensor comprises a torque sensor coupled to an output shaft of a motor coupled to the closure member, wherein the torque sensor is configured to measure closure force.

Example 26. The control system of one or more of Example 22 through Example 25, wherein the force sensor comprises a strain gauge coupled to the closure member, wherein the strain gauge is configured to measure closure force.

Example 27. The control system of one or more of Example 22 through Example 26, wherein the force sensor comprises a load cell coupled to the closure member, wherein the load cell is configured to measure closure force.

Example 28. The control system of one or more of Example 22 through Example 27, further comprising a position sensor coupled to the closure member, wherein the position sensor is configured to measure the position of the closure member.

Robotic Surgical Instrument with Closed Loop Feedback Techniques for Advancement of Closure Member During Firing In use of a motorized robotic surgical stapling system, the force on the closure member drops slightly during a waiting period after clamping the tissue due to compression on the tissue and fluid egress. Further, the force on the closure member drops precipitously from the moment the firing member couples into the clamp arm and the closure force is transferred from the closure member to the firing member. Therefore, the present disclosure provides a closed loop feedback control system configured to advance the closure member during the waiting period and during the firing stroke while the firing member is advancing distally. The present disclosure also provides individually controllable closure and firing members configured to couple to a robotic surgical instrument interface.

In one aspect, the present disclosure provides various techniques for adaptive control of the closure member velocity. In one aspect, the present disclosure provides techniques for adaptive control of the closure member velocity which measures at least two parameters of a robotic shaft. The parameters associated with the robotic shaft include, without limitation, firing member stroke location, firing member load, knife advancement velocity, closure tube stroke location, closure tube load, among others, through a detachable robotic interface unit and a removable cartridge along with circuitry disposed in the robotic interface and the cartridge that can either identify themselves and their status or provide parameters or a control program for actuating the device or end effector and recording its usage.

In one aspect, the present disclosure provides closed loop feedback control techniques for advancing a closure member during a waiting period and during a firing stroke. A closed loop feedback control system may be configured to receive at least two parameters such as firing member stroke location, firing member load, knife advancement speed, closure tube stroke location, or closure tube load in order to progressively close the closure member the firing member is advancing.

Closure tube advancement may be controlled based on the location of the firing member within its stroke and the force measured on the closure tube actuator. In one aspect, closure tube advancement may be controlled based on the closure tube continued advancement based on both the location of the firing member within its stroke and the measured closure force (FTC). Closure tube advancement while firing provides lower firing force (FTF) and results in larger possible articulation angles, shorter joint lengths, and better tissue capacity.

Figure 42:
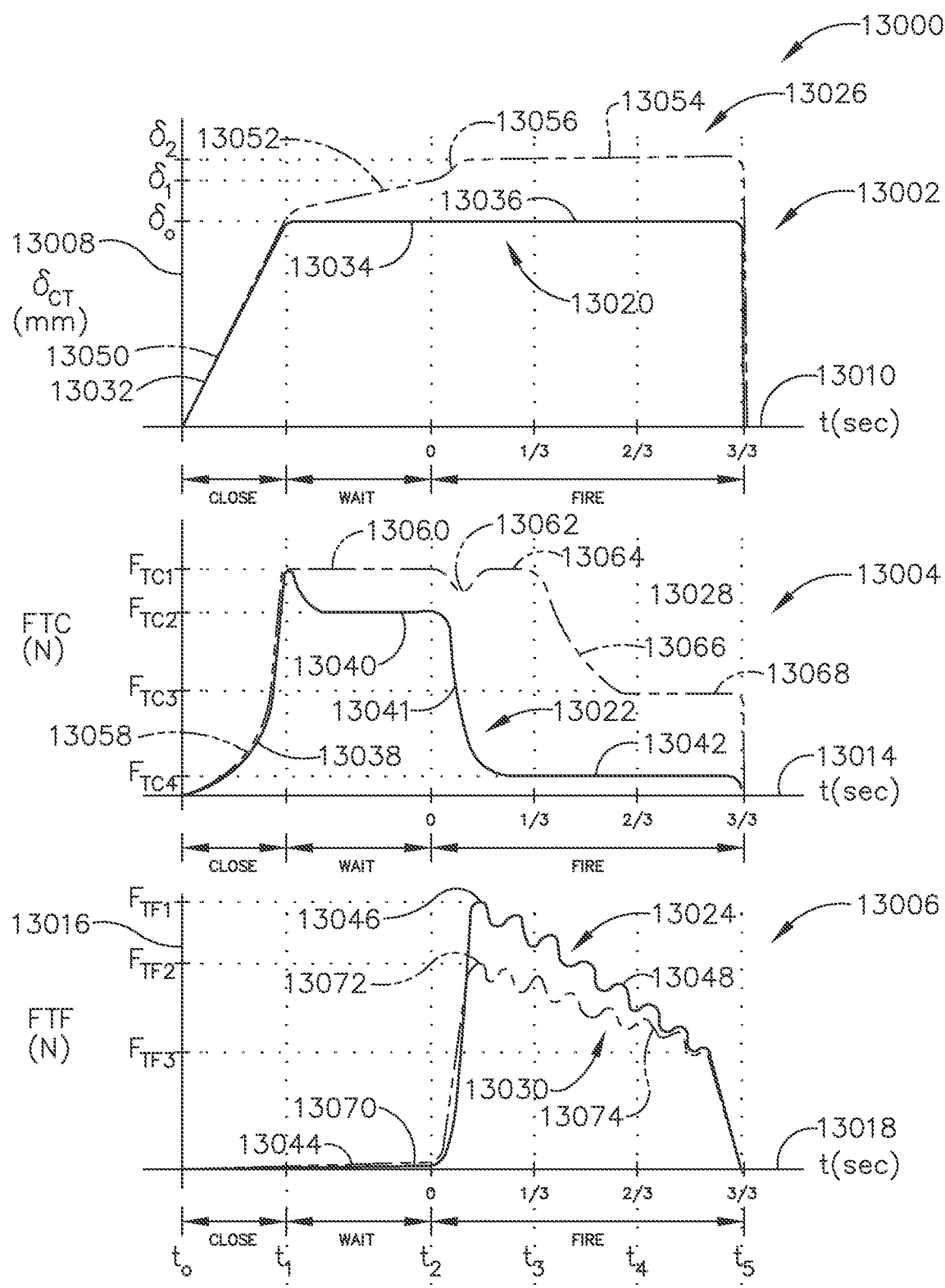
FIG. 42 is a diagram of a displacement graph depicting a plot of closure member displacement as a function of time, a closure member closure force graph depicting a plot of closure force (FTC) as a function of time, and a firing member firing force graph depicting a plot firing force (FTF) as a function of time according to one aspect of this disclosure.

FIG. 42 is a diagram 13000 of three graphs. A displacement graph 13002 depicts a plot of closure member displacement as a function of time. A closure force graph 13004 depicts a plot of closure member closure force (FTC) as a function of time. A firing force graph 13006 depicts a plot of firing member firing force (FTF) as a function of time. The three graphs 13002, 13004, 13006 depict plots over three distinct periods or phases referred to as a closure stroke (CLOSE), a waiting period (WAIT), and a firing stroke (FIRE). Each graph 13002, 13004, 13006 includes two separate plots where the first plot represents a conventional closure member where a closure force is applied only during a closure stroke and the second plot represents a closure member where a closure force is maintained or applied beyond the closure stroke. The diagram 13000 will be described with reference to FIG. 30, which is a schematic diagram of a feedback control system configured to receive at least two parameters such as the location of the firing member (e.g., I-beam 2514) along the firing stroke, the load on the firing member, the advancement velocity of the firing member, the location of the closure tube (e.g., closure tube 1040, 1042), or the load on the closure tube 1040, 1042 and to progressively close the anvil 2516 during the firing stroke. The control circuit 2510 is configured to receive such parameters from the position sensor 2534, the current sensor 2536, other sensors 2538 positioned throughout the instrument 2500, timer/counter circuit 2531, and/or any of the torque sensors 2544a-2544e positioned at the output of the motors 2504a-2504e, respectively. Based on the feedback parameters, the control circuit 2510 controls the displacement of the closure 1040, 1042 (forwards and backwards) to maintain a desired closure force and/or firing force during the firing stroke period based on the measured closure force and position of the I-beam 2514 and the closure force on the closure tube 1040, 1042.

The displacement graph 13002 depicts first and second plots 13020, 13026 of closure member displacement as a function of time, where the displacement $\delta_{CT}$ (mm) of the closure member is plotted along the vertical axis 13008 and time (sec) is plotted along the horizontal axis 13010. The first plot 13020 depicts conventional displacement of a closure member as a function of time where the closure member travels over a fixed distance and stops. The second graph 13026 depicts displacement of a closure member as a function of time where the closure member closure force is during feedback control according to one aspect of this disclosure.

The closure force graph 13004 depicts first and second plots 13022, 13028 of closure force as a function of time, where the closure force (FCT) N is plotted along the vertical axis 13012 and time is plotted along the horizontal axis 13014. The first plot 13022 depicts closure force applied to the closure member as a function of time where the closure member travels over a fixed distance and stops and applies a constant closure force during the firing stroke. The second plot 13028 depicts closure force applied to the closure member as a function of time where the closure member force is under feedback control during the firing stroke according to one aspect of this disclosure.

The firing force graph 13006 depicts first and second plots 13024, 13030 of firing force as a function of time graph, where the firing force (FTF) N is plotted along the vertical axis 13016 and time (sec) is plotted along the horizontal axis 13018. The first plot 13024 depicts conventional firing force applied to the firing member as a function of time where the closure member travels over a fixed distance and stops and applies a constant closure force during the firing stroke. The second plot 13030 depicts firing force as a function of time where the closure member is under feedback control while the member is advancing distally during the firing stroke according to one aspect of this disclosure.

The closure stroke (CLOSE) period begins at time $t_0$ and ends at time $t_1$. During the closure stroke, a closure force 13038, 13058 is applied to the closure member, e.g., closure tube 1040, 1042 (FIGS. 4 and 6-10), causing the closure tube 1040, 10402 to translate distally 13032, 13050 to move the anvil 2516 relative to the staple cartridge 2518 in response to the actuation of the closure motor 2504b through one or more transmission components 2506b. During closure stroke period, the firing force 13044, 13070 is substantially zero. As the closure force 13038, 13058 increases exponentially to a maximum force of $F_{TC1}$, the closure tube 1040, 1042 travels a fixed distance to 60 (mm). The closure force reaches a maximum force $F_{TC1}$ at time $t_1$. The initial clamping time period can be about one second, for example.

Following the closure stroke period is the waiting (WAIT) period, which begins at time $t_1$ and ends at time $t_2$. A waiting period can be applied prior to initiating a firing stroke. The waiting period allows fluid egress from tissue compressed by the end effector 2502, which reduces the thickness of the compressed tissue yielding a smaller gap between the anvil 2516 and the staple cartridge 2518 and a reduced closure force at the end of the waiting period. If no additional closure force is applied to the closure tube 1040, 1042, the closure force 13040 drops to $F_{TC2}$ due to the reduction in tissue thickness and loss of fluid and the displacement 13034 remains at $\delta_0$. In contrast, if a constant closure force 13060 is applied to the closure tube 1040, 1042 during the waiting period, the closure tube 1040, 1042 undergoes additional displacement 13052 to 61.

The firing stroke (FIRE) period begins at time $t_2$ and ends at time $t_5$. The firing stroke starts at the end of the waiting period. In a conventional closure force process, as the firing force increases exponentially at the initial stage of the firing stroke, the closure force 13041 drops exponentially as the I-beam 2514 couples into the anvil 2516 and the closing load is transferred from the closure tube 1040, 1042 to the I-beam 2514. In a conventional process, as firing force 13046 increases rapidly to $F_{TF1}$ the closure force decreases rapidly to $F_{TC3}$ and the closure force remains constant during the rest of the firing stroke and the firing force 13048 drops steadily to $F_{TF3}$ at the end of the stapling period and then drops to zero at the end of the firing stroke. During the firing period is period, the displacement 13036 of the closure tube remains constant. In other words, in a conventional process, the displacement of the closure tube 1040, 1042 stops after the initial displacement during the closure stroke.

In one aspect, the present disclosure provides closed loop feedback control system for advancing the closure tube 1040, 1042 during the firing stroke. A closed loop feedback control system comprising a control circuit 2510 configured to receive at least two parameters such as the location of the I-beam 2510 (firing member) during the firing stroke, the load on the I-beam 2514 (firing member), the advancement velocity of the (firing member), the location of the closure tube 1040, 1042 (closure member), and/or the load on the closure tube 1040, 1042 (closure member) and progressively close the anvil 2516 during the firing stroke. Accordingly, the closure force may be varied during the firing stroke by controlling the displacement (advancement or retraction) of the closure tube 1040, 1042 based on measured feedback parameters to lower the overall firing force as shown in the second firing force graph 13030 relative to the conventional firing force graph 13024.

For example, referring to the second plot 13028 portion of the closure force graph 13004 and the second plot 13030 portion of the firing force graph 13006, following the waiting period, the closure tube 1040, 1042 is under the constant closure force 13060 applied during the waiting period until the firing force 13072 rapidly increases to $F_{TF2}$ and the closure force 13062 starts to decrease as the I-beam 2514 couples into the anvil 2516 and the closing load is transferred from the closure tube 1040, 1042 to the I-beam 2514. During this brief period, however, the control circuit 2510 of the closed loop feedback receives the closure force 13062 from the torque sensor 2544b coupled to the output shaft of the closure motor 2504b and the position of the I-beam 2514 during the firing stroke and increases the closure force 13064 on the closure tube 1040, 1042 based on these measured parameters. To increase the closure force 13064, the control circuit 2510 advances the closure tube 1040, 1042 displacement 13056 to $\delta_2$ and, in this example, remains at that position 13054 for the rest of the firing stroke. Accordingly, following the brief dip in closure force 13062, the closure force 13064 recovers to $F_{TC1}$ and remains constant until the I-beam 2514 is approximately at one-third (⅓) of the firing stroke period. At which time, the control circuit 2510 enables the closure force 13066 to decrease from $F_{TC1}$ to $F_{TC3}$ when the I-beam 2514 is approximately at two-thirds (⅔) of the firing stroke period. In this example, the closure force 13068 remains constant at $F_{TC3}$ for the remaining one-third (⅓) of the firing stroke period. As shown by the second plot 13030, the firing force 13074 decreases from a peak firing force $F_{TF2}$, which is below the peak firing force $F_{TF1}$ of the conventional process, to $F_{TF3}$, which coincides with the firing force of the conventional process and rapidly drops to zero for the remainder of the firing stroke period until the end of the firing stroke is reached.

Accordingly, closure tube 1040, 1042 advancement can be controlled based on the location of the firing member such as the measured position of the I-beam 2514 within the firing stroke period and the measured closure force applied to the closure tube 1040, 1042 as measured, for example, by the torque sensor 2544b coupled to the output shaft of the closure motor 2504b. The closure tube 1040, 1042 may be advanced or retracted based on these feedback parameters. The outcome produces a lower firing force (FTF) and provides larger possible articulation angles, shorter joint lengths, and better tissue capacity.

Accordingly, with reference now primarily to FIG. 30, in one aspect the control circuit 2510 is configured to provide progressive closure of a closure member (e.g., closure tube 1040, 1042) during the waiting period and during the firing stroke according to one aspect of this disclosure. As previously described, in a conventional clamping and firing process the closure force drops during the waiting period because of tissue compression and fluid egress from the tissue. Thus, during the closure and waiting periods, the control circuit 2510 monitors the closure force on the closure tube 1040, 1042 and advances the closure tube 1040, 1042 by providing a motor set point signal to the motor control 2508b circuit, which applies a motor drive signal to the motor 2504b. The motor 2504b drives a transmission 2506b, which includes one or more gears or other linkage components to couple the output of the motor 2504b to the closure tube 1040, 1042. Accordingly, the closure tube 1040, 1042 applies a closure force to the anvil 2516. A torque sensor 2444b coupled to the output of the motor 2504b provides the closure force to the control circuit 2510.

Furthermore, at the beginning of the firing stroke as the closure force is transferred from the closure tube 1040, 1042 to the I-beam 2514, the control circuit 2510 receives the position the of the I-beam 2514 (or other component of the firing system) from the position sensor 2534. After the I-beam 2514 advances distally and couples into the anvil 2516, during the firing stroke the control circuit 2510 receives the closure force applied to the closure tube 1040, 1042 from the torque sensor 2544b and the position of the I-beam 2514 from the position sensor 2534 to adjust the displacement of the closure tube 1040, 1042 and thus control force based on the measured closure force and the measured position of the I-beam 2514.

Figure 43:
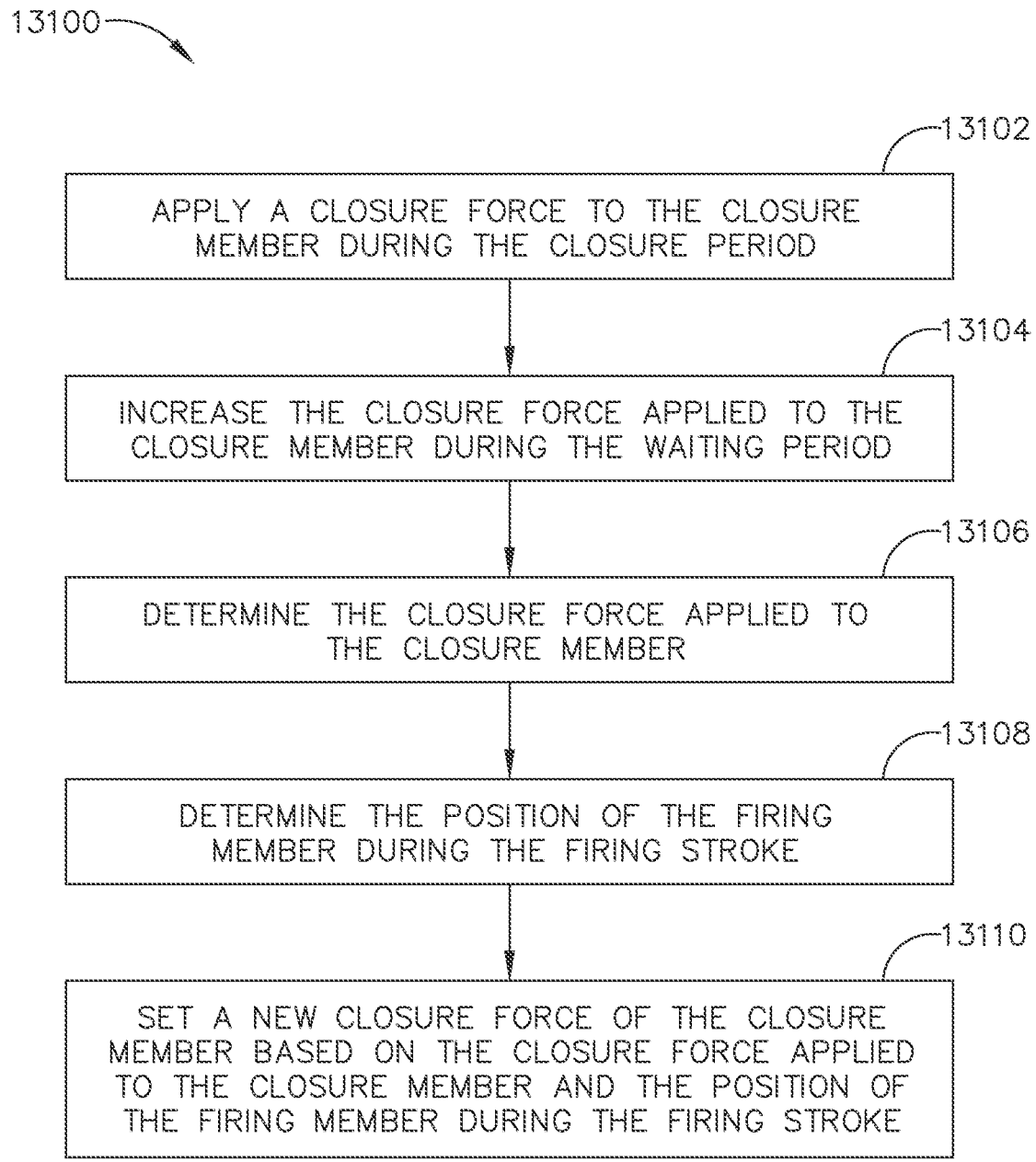
FIG. 43 is a logic flow diagram depicting a process of a control program or a logic configuration for determining the velocity of a closure member according to one aspect of this disclosure.

FIG. 43 is a logic flow diagram depicting a process 13100 of a control program or a logic configuration for determining the closure force applied to the closure member and the position of the firing member and setting the closure force based on measured closure force and position information. The control circuit 2510 initiates the closure stroke by applying 13102 a closure force to the closure member during the closure period. To apply 13102 the closure force to the closure member, the control circuit 2510 sets a motor set point to the motor control 2508b, which applies a motor drive signal to the motor 250b causing the transmission 2506b to displace the closure tube 1040, 1042 and close the anvil 2516 to compress tissue positioned between the anvil 2516 and the staple cartridge 2518. At the end of the closure period, the control circuit 2510 increases 13104 the closure force applied to the closure member during the waiting period to compensate for tissue compression and fluid egress. The control circuit 2510 determines 13106 the closure force applied to the closure member. For example, the control circuit 2510 receives the closure force from the torque sensor 2544b or other sensors 2538 such as a strain gauge located in the end effector 2502 to measure force or a load cell configured to measure load on the closure tube 1040, 1042. The firing stroke begins after the end of the waiting period. During the firing stroke, the control circuit 2510 determines 13108 the position of the firing member. For example, the control circuit 2510 receives a position signal from the position sensor 2534. The control circuit 2510 then sets 13110 the closure force of the closure member based on the closure force applied to the closure member and the position of the firing member during the firing stroke.

The functions or processes 13100 described herein may be executed by any of the processing circuits described herein, such as the control circuit 961 (FIG. 22), 800 (FIG. 23), 810 (FIG. 24), 820 (FIG. 25), 4420 (FIG. 26), and/or control circuit 2510 (FIG. 30). Aspects of the motorized surgical instrument may be practiced without the specific details disclosed herein.

Example 1. A control system for a robotic surgical system, the control system comprising: a control circuit configured to: determine a closure force applied to a closure member; determine a position of a firing member; and set a new closure force based on the closure force applied to the closure member and the position of the firing member.

Example 2. The control system of Example 1, further comprising a force sensor coupled to the control circuit, wherein the force sensor is configured measure the closure force.

Example 3. The control system of Example 2, wherein the force sensor comprises a torque sensor coupled to an output shaft of a motor coupled to the closure member, wherein the torque sensor is configured to measure closure force.

Example 4. The control system of one or more of Example 2 through Example 3, wherein the force sensor comprises a strain gauge coupled to the closure member, wherein the strain gauge is configured to measure closure force.

Example 5. The control system of one or more of Example 2 through Example 4, wherein the force sensor comprises a load cell coupled to the closure member, wherein the load cell is configured to measure closure force.

Example 6. The control system of one or more of Example 2 through Example 5, further comprising a position sensor coupled to the firing member, wherein the position sensor is configured to measure the position of the firing member.

Example 7. The control system of one or more of Example 1 through Example 6, wherein the control circuit is configured to advance the closure member during at least a portion of the firing stroke.

Example 8. A control system for a robotic surgical system, the control system comprising: a first motor configured to couple to a closure member; a force sensor configured to measure closure force applied to the closure member; a control circuit coupled to the first motor and the force sensor, wherein the control circuit is configured to: receive, from the force sensor, actual closure force applied to the closure member; receive, from the position sensor, a position of a firing member; and set a new closure force based on the actual closure force applied to the closure member and the position of the firing member.

Example 9. The control system of Example 8, wherein the force sensor comprises a torque sensor coupled to an output shaft of the first motor, wherein the torque sensor is configured to measure closure force.

Example 10. The control system of one or more of Example 8 through Example 9, wherein the force sensor comprises a strain gauge coupled to the closure member, wherein the strain gauge is configured to measure closure force.

Example 11. The control system of one or more of Example 8 through Example 10, wherein the force sensor comprises a load cell coupled to the closure member, wherein the load cell is configured to measure closure force.

Example 12. The control system of one or ore of Example 8 through Example 11, further comprising a position sensor coupled to the closure member, wherein the position sensor is configured to measure the position of the closure member.

Example 13. The control system of one or more of Example 8 through Example 12, further comprising a second motor coupled to the firing member, wherein the control circuit is configured to advance the firing member during at least a portion of a firing stroke of the firing member.

Example 14. A control system for a robotic surgical system, the control system comprising: a control circuit configured to: apply a closure force to a closure member during a closure period; increase the closure force during a waiting period following the closure period; determine a closure force applied to the closure member; determine a position of a firing member during a firing stroke; and set a new closure force of the closure member based on the closure force and the position of the firing member.

Example 15. The control system of Example 14, further comprising a force sensor coupled to the control circuit, wherein the force sensor is configured measure the closure force.

Example 16. The control system of Example 15, wherein the force sensor comprises a torque sensor coupled to an output shaft of a motor coupled to the closure member, wherein the torque sensor is configured to measure closure force.

Example 17. The control system of one or more of Example 15 through Example 16, wherein the force sensor comprises a strain gauge coupled to the closure member, wherein the strain gauge is configured to measure closure force.

Example 18. The control system of one or more of Example 15 through Example 17, wherein the force sensor comprises a load cell coupled to the closure member, wherein the load cell is configured to measure closure force.

Example 19. The control system of one or more of Example 15 through Example 18, further comprising a position sensor coupled to the firing member, wherein the position sensor is configured to measure the position of the firing member.

Example 20. The control system of one or more of Example 14 through Example 19, wherein the control circuit is configured to advance the closure member during at least a portion of the firing stroke.

System for Controlling Articulation Forces

In some aspects, a control algorithm is provided for manipulating a pair of articulation arms configured to control an articulation angle of an end effector of the robotic surgical instrument. Other aspects of the present disclosure focus on the robotic arm system, including the pair of articulation arms coupled to the end effector and guided by independent motors, e.g., motors 2504*d* and 2504*e*. The two articulation arms are designed to exert antagonistic forces competing against one another and whose magnitudes are apportioned according to a ratio specified in the control algorithm. The ratio of the antagonistic forces may be used to determine the articulation angle of the head or end effector of the robotic surgical arm. In one aspect the present disclosure provides control algorithms to reliably govern the movements of two or more of these components when there is an interrelationship.

Figure 44:
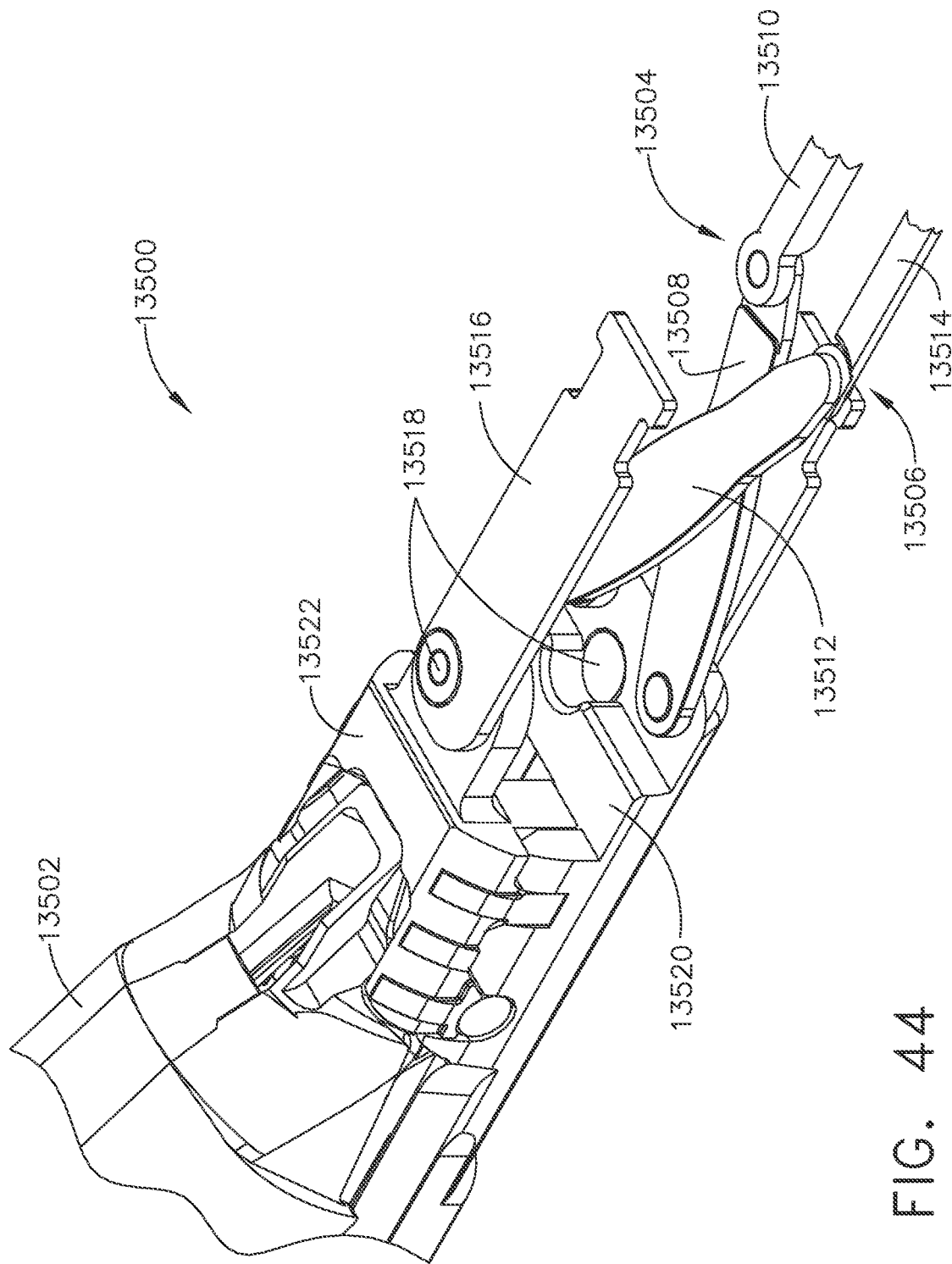
FIG. 44 shows an example structural portion of a robotic surgical arm including two articulation arms connected to an end effector, according to some aspects of the present disclosure.

Referring to FIG. 44, illustration 13500 shows an example structural portion of a robotic surgical arm including two articulation arms connected to an end effector, according to some aspects of the present disclosure. Here, the end effector includes an anvil 13502 connected to right articulation arm 13504 and left articulation arm 13506. The right articulation arm 13504 includes a right articulation link 13508 and a right articulation bar 13510. These two components are connected via a hinge as shown. Similarly, the left articulation arm 13506 includes a left articulation link 13512 and a left articulation bar 13514. As shown, the left and right articulation arms cross and are connected to the end effector via hinges next to the channel 13520. Pulling or pushing forces of the left and right articulation arms can cause the end effector to articulate about the articulation pivots 13518. The off-center pivot link 13516 helps to stabilize the end effector as it articulates, due to the off-center pivot link 13516 being stably positioned into the shaft where the articulation arms reside, which is not shown here for illustration purposes. The anvil 13502 is coupled to the articulation joints via the anvil retainer 13522.

Referring to FIGS. 45-47, examples are shown of how movements of the articulation arms cause the end effector to articulate, according to some aspects. In FIG. 45, the anvil 13502 is in a neutral or straight position relative to the articulation arms 13504 and 13506. In FIG. 46, the left articulation arm 13506 is moved up along direction B, while simultaneously the right articulation arm 13504 is moved down along direction C. Because the hinges of the articulation arms that connect to the end effector are positioned on opposite sides of the articulation pivot 13518, these described motions cause the anvil 13502 to articulate in the counterclockwise direction A, as shown. This is consistent when noticing the fact that the hinge of the left articulation arm 13506 is to the right of the pivot 13518, and therefore an upward movement in direction B is consistent with causing a counterclockwise motion. Similarly, because the hinge connecting the right articulation arm 13504 is positioned to the left of the pivot 13518, a downward movement in direction C is consistent with causing a counterclockwise motion. In contrast, as shown in FIG. 47, reverse movements by the articulation arms cause the anvil 13502 to move in the reverse, i.e., clockwise, direction. That is, a movement by the right articulation arm 13504 in the upward direction B, and any simultaneous movement by the left articulation arm 13506 in the downward direction C, create a clockwise motion of the anvil 13502 about the pivot 13518.

Figure 48:
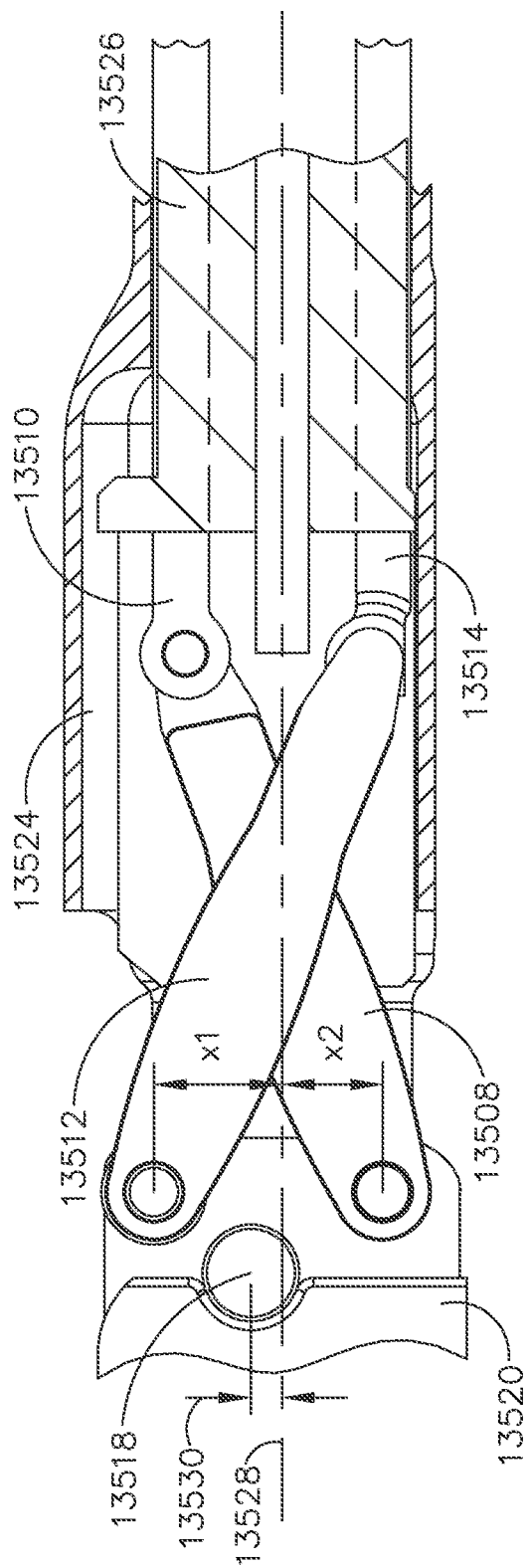
FIG. 48 shows, according to some aspects, the pivot moment of the end effector is actually off from the centerline of the shaft structure.

Referring to FIG. 48, according to some aspects, the pivot moment of the end effector is actually off from the centerline of the shaft structure. Shown here is the centerline 13528 of the shaft 13524, which represents the point equidistant to opposite sides of the channel retainer 13526. The left and right articulation bars 13514 and 13510 are positioned within the channel retainer 13526 at spacing equidistant to the centerline 13528. However, the articulation pivot 13518 is positioned slightly off-center, such as at a distance 13530 from the centerline 13528.

This in turn has the left articulation link 13512 positioned further away from the centerline 13528 in order to connect to the channel 13520, compared to where the right articulation link 13508 is connected to the channel 13520. The asymmetry of this design may have several purposes. For example, the asymmetric design may create a more stable configuration when the articulation arms are oriented one on top of the other, e.g., the right articulation bar 13510 is above the left articulation bar 13514, as opposed to the shaft being rotated 90° such that the articulation arms are side-by-side to one another. The effects of gravity create a need for greater stability over the top of the end effector, suggesting an imbalance of forces needed to be applied to the articulation arms. Second, the asymmetric design also creates a control algorithm with asymmetric properties. This creates a set of forced ratios between the two articulation arms that is unique at every point, in that the ratio of forces between the two articulation arms is always going to be different. This design may help to diagnose problems and debug issues between the interplay of the two articulation arms because it is known that the force ratio profile is unique at every point.

Figure 49:
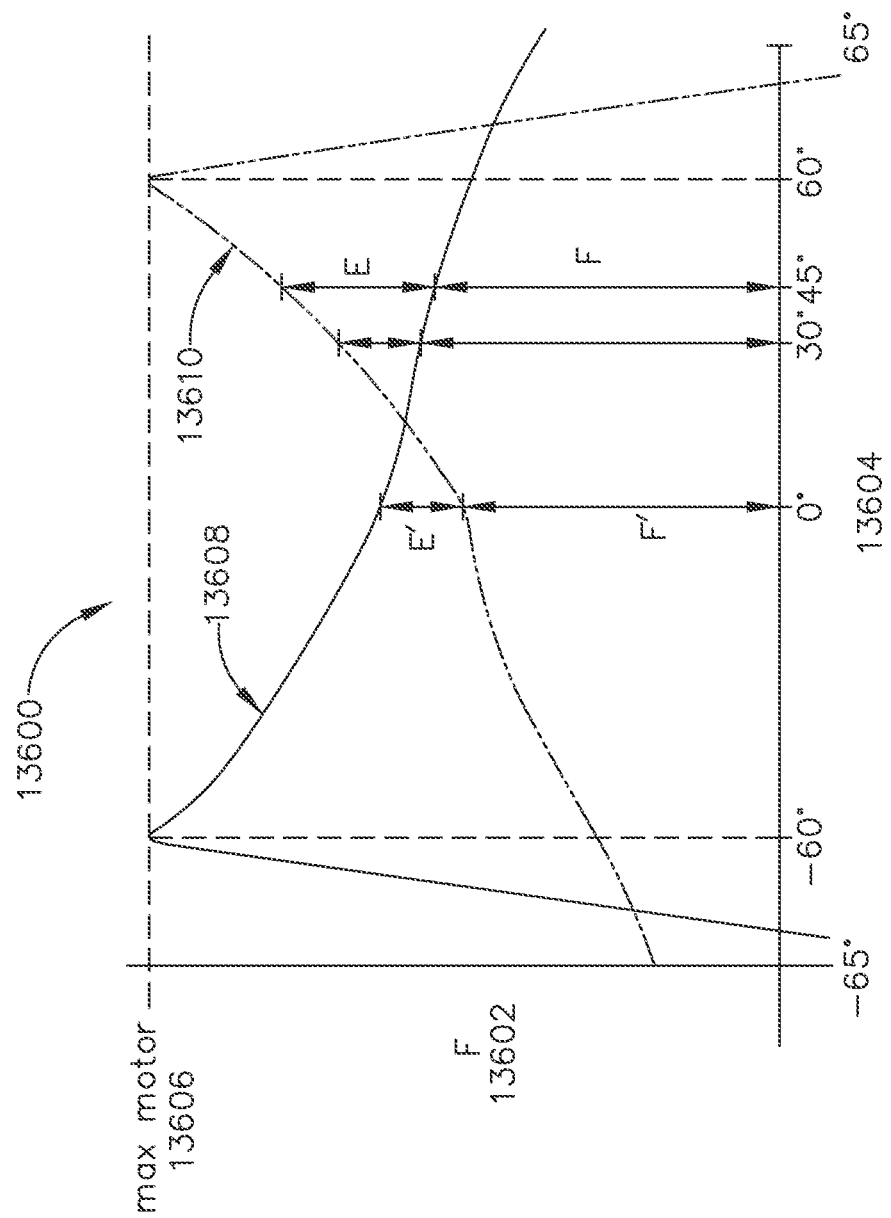
FIG. 49 shows an example graph representing an amount of force applied by both of the articulation arms as a function of a degree of articulation of the head from a horizontal centerline, according to some aspects.

Referring to FIG. 49, illustration 13600 shows an example graph representing an amount of force applied by both of the articulation arms as a function of a degree of articulation of the head from a horizontal centerline, according to some aspects. As shown, the graph 13600 shows force as the Y axis 13602, and a degree of articulation from a horizontal centerline represents the X axis 13604. A maximum value 13606 represents the maximum amount of force that the motors may apply to the articulation arms. In this example, the curve 13608 represents an amount of force that should be applied to the left articulation arm 13506 as a function of the desired articulation angle according to the X axis 13604, and the curve 13610 represents an amount of force that should be applied to the right articulation arm 13504 as a function of the same desired articulation angle. In this example, the maximum range of articulation is +/−60° from the centerline.

In some aspects, causing articulation of the head/end effector involves applying forces to both of the articulation arms in an antagonistic relationship. For example, each motor coupled to the articulation arms may exert pulling forces on both of the articulation arms at the same time. The ratio of the amount of pulling force between the two articulation arms may determine the angle at which the head/end effector articulates. This ratio of forces may be mapped or represented by the graph 13600.

For example, in order to cause the head/end effector to articulate 45° from the centerline, a pulling force in the magnitude of length E should be applied to the right articulation arm, according to the curve 13610. Simultaneously, a pulling force in the magnitude of length F should be applied to the left articulation arm, according to the curve 13608. In general, the ratio between the magnitudes E and F may dictate what articulation angle is achieved, rather than the absolute magnitude of the forces themselves.

As another example, because the articulation pivot 13518 is located off-center, the amount of counterbalancing or antagonistic forces required to stabilize the head/end effector at an even 0° is not equal between the two articulation arms. This is exemplified by the forces E' and F', which are different amounts of force applied to the two articulation arms at the 0° point in the graph 13600.

Figure 50:
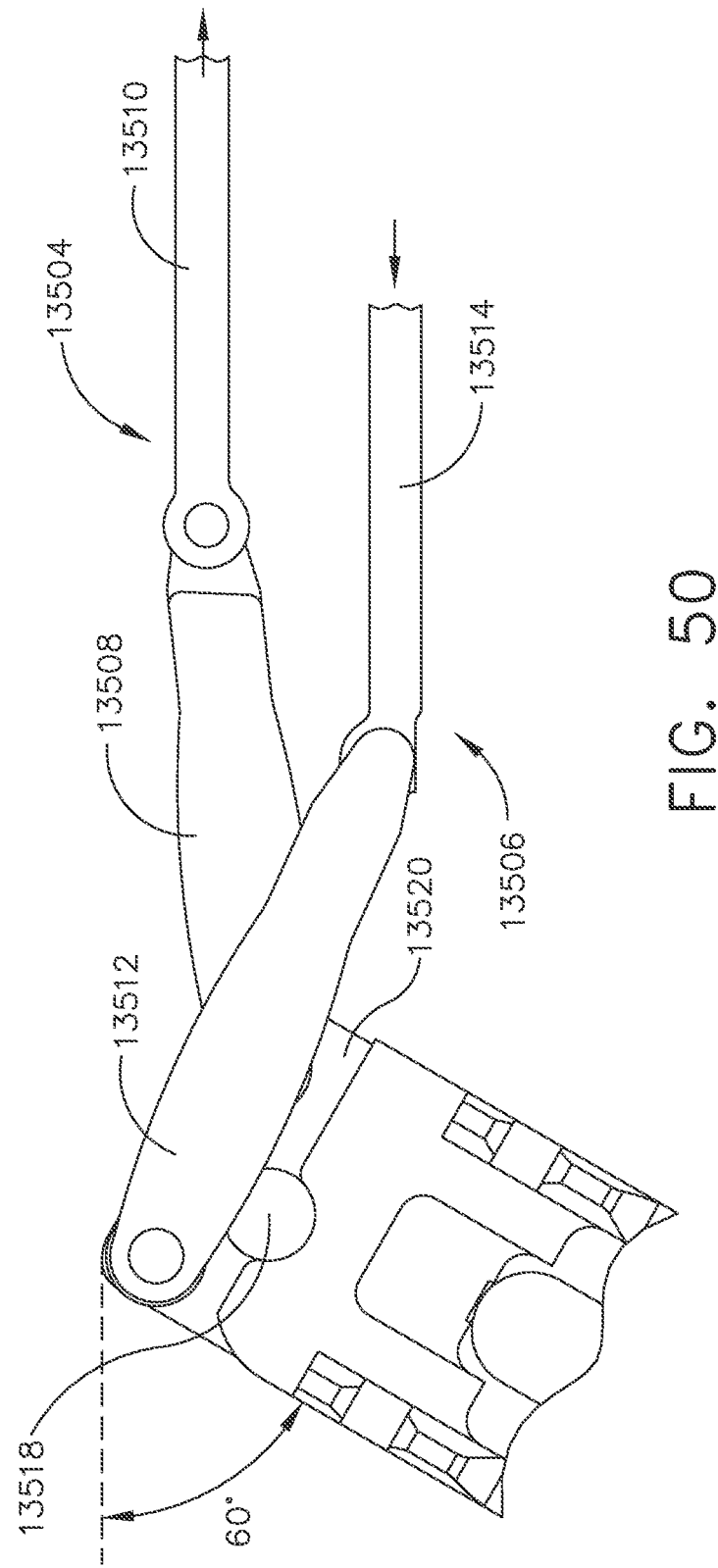
FIG. 50 shows an example of how forces may be applied to the two articulation arms in order to cause the head/end effector to articulate 60° from the centerline, according to some aspects.

Referring to FIG. 50, shown is an example of how antagonistic forces may be applied to the two articulation arms in order to cause the head/end effector to articulate 60° from the centerline, according to some aspects. Here, a motor coupled to the right articulation arm 13504 may apply a pulling force substantially greater than a pulling force applied by a second motor to the left articulation arm 13506. The exact ratio of forces between the two articulation arms may be determined by the example control algorithm graph 13600 in FIG. 49, according to the amounts of forces illustrated at the 60° line in the graph. The larger amount of pulling force applied to the right articulation arm 13504 in comparison to the left articulation arm 13506 results in the right articulation arm 13504 being pulled to the right in FIG. 50. Accordingly, this ratio of forces results in the left articulation arm 13506 moving to the left or being pushed toward the head/end effector. However, because there is still some amount of pulling force being applied to the left articulation arm 13506, the antagonistic forces effectively balance out or equilibrate at a point such that the head/end effector articulates 60° from the centerline, as shown.

Figure 51:
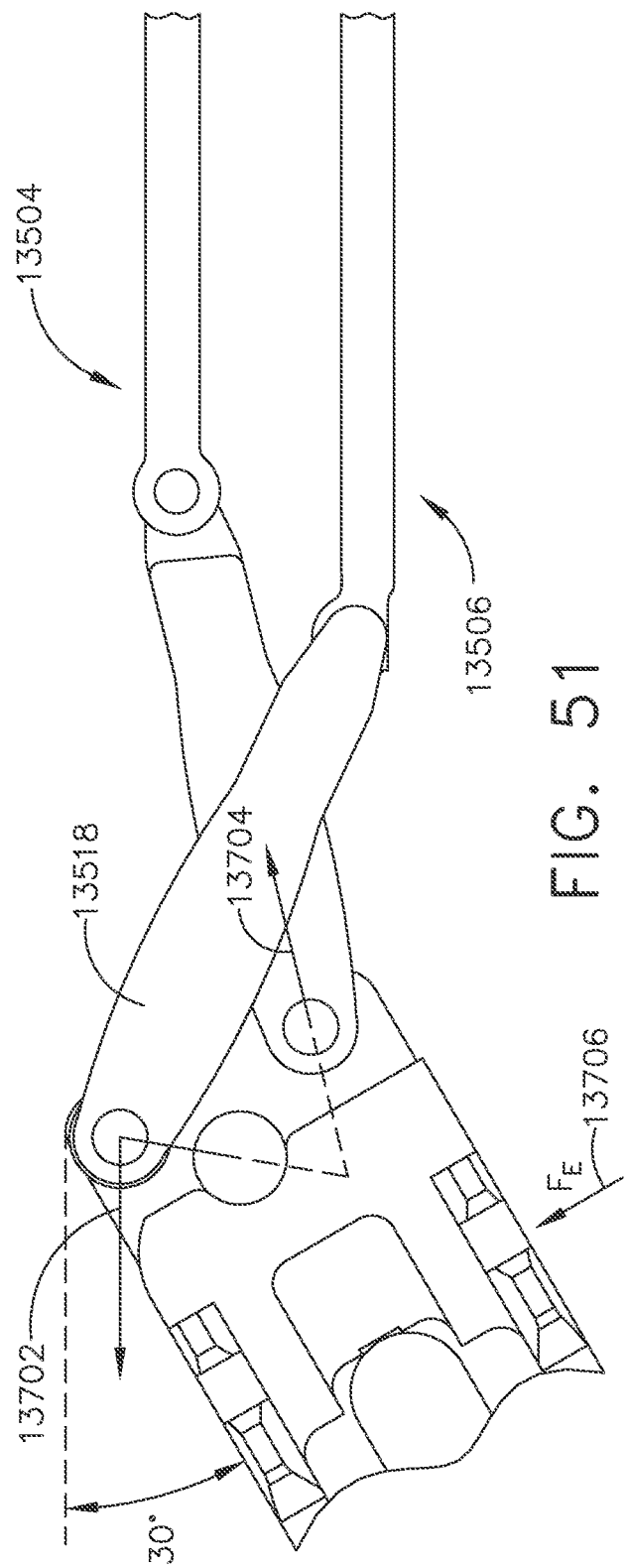
FIG. 51 shows another example of how forces may be applied to the two articulation arms in order to cause the head/end effector to articulate 30° from the centerline, according to some aspects.

Referring to FIG. 51, shown is another example of how forces may be applied to the two articulation arms in order to cause the head/end effector to articulate 30° from the centerline, according to some aspects. Here, the motor coupled to the right articulation arm 13504 may apply a pulling force greater than the pulling force applied to the left articulation arm 13506 by the second motor. In this case, the difference in the forces is not as substantial as the ones described in FIG. 50. As an example, the exact ratio of forces between the two articulation arms may be determined by the example control algorithm graph 13600 in FIG. 49, according to the amount of forces illustrated at the 30° point in the graph. It can be seen therefore that the ratio of the two forces is smaller, meaning the smaller, countervailing force applied to the left articulation arm 13506 is closer in magnitude to the prevailing force applied to the right articulation arm 13504. Starting from the position of articulation in the illustration of FIG. 50, the change in forces applied to the two articulation arms in FIG. 51 results in an effective force F E 13706 applied to the head/end effector in FIG. 51. The arrows 13702 and 13704 represent the changes in force applied to their respective articulation arms relative to the forces illustrated in previous FIG. 50.

Figure 52:
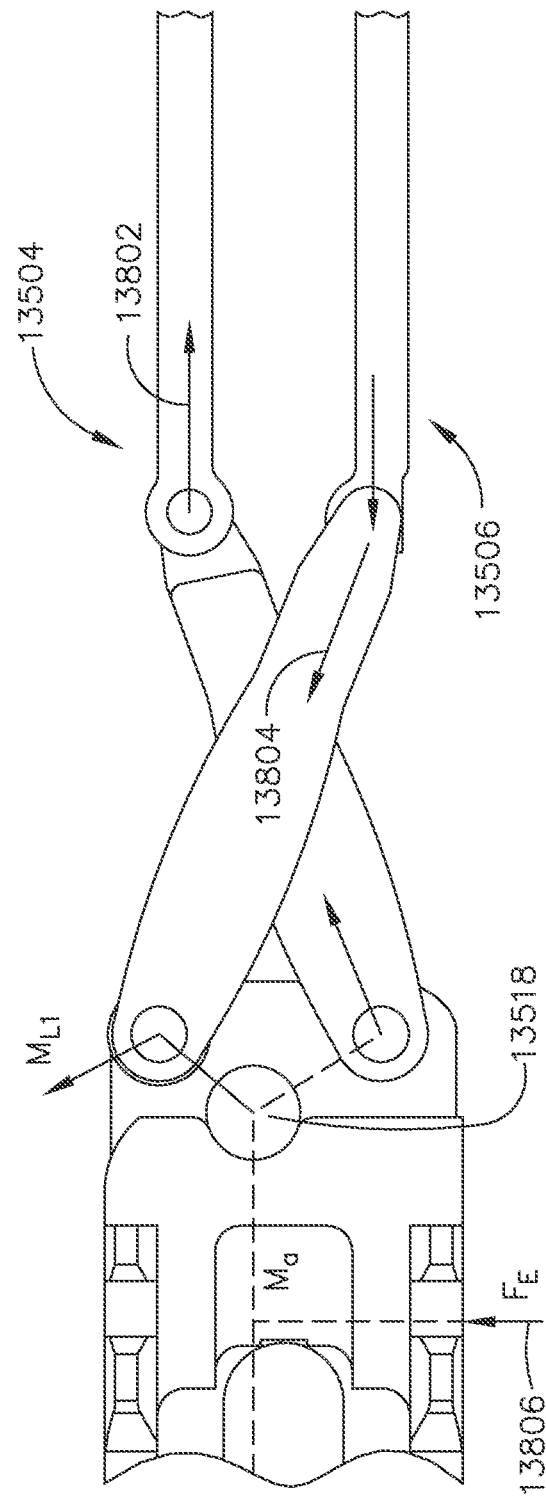
FIG. 52 shows a third example of how forces may be applied to the two articulation arms in order to cause the head/end effector to articulate back to the center or neutral position, according to some aspects.

Referring to FIG. 52, shown is a third example of how forces may be applied to the two articulation arms in order to cause the head/end effector to articulate back to the center or neutral position, according to some aspects. Here, the motor coupled to the right articulation arm 13504 may apply a pulling force less than a pulling force applied to the left articulation arm 13506 by the second motor. As shown in the graph 13600 of FIG. 49, the antagonistic pulling force of the left articulation arm 13506 is actually greater then the force applied to the right articulation arm 13504 at the 0° point. This makes sense when considering that the articulation pivot 13518 is off-center and closer to the hinge of the left articulation arm 13506. This requires the left articulation arm 13506 to deliver more torque relative to the right articulation arm 13504 in order to balance the forces. In this example, the change in the amount of forces applied to both of the articulation arms compared to FIG. 51 results in an effective force F E 13806 being applied to the center of mass of the head/end effector.

Figure 53:
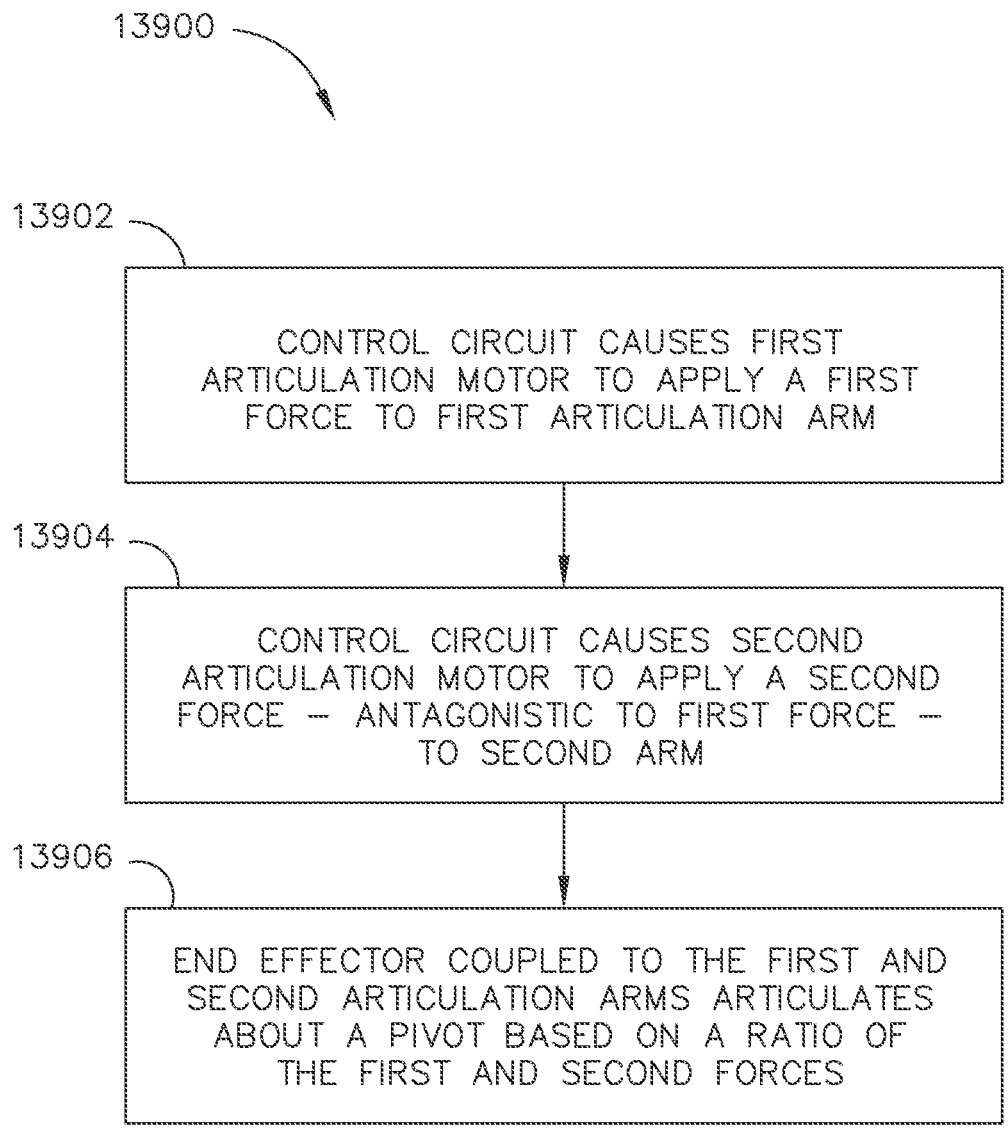
FIG. 53 illustrates a logic flow diagram depicting a process of a control program or a logic configuration for causing articulation of an end effector of a robotic surgical system based on controlling two independent articulation arms, according to some aspects.

Referring to FIG. 53, a logic flow diagram depicting a process 13900 of a control program or a logic configuration for causing articulation of an end effector of a robotic surgical system based on controlling two independent articulation arms, according to some aspects. As shown in FIG. 30, the control circuit 2510 may be configured to command motor control 2508*d* and motor control 2508*e*. These may be coupled to respective motors 2504*d* and 2504*e*. These motors may ultimately respectively create a pulling or pushing force applied to the articulation arms 13504 and 13506. The independent nature of the two motors, while ultimately being used to control the articulation of a single end effector, allows for a clean design that is easier to program in a precise manner and also diagnose for problems and replacement parts.

The control circuit, e.g., control circuit 2510, may be configured to cause 13902 the first articulation motor, e.g., motor 2504*d*, to apply first force to the first articulation arm, e.g., articulation arm 2542*a* or either of articulation arms 13504 and 13506. In some aspects, the first force may be a pulling force configured to draw the first articulation arm proximally toward the motor, while in other cases the force may be a pushing force in the opposite direction relative to the end effector.

The control circuit may be configured to cause 13904 a second articulation motor, e.g., motor 2504*e*, to apply a second force to a second articulation arm, e.g., articulation arm 2542*b* or the other of articulation arms 13504 and 13506. The second force applied is antagonistic to the first force, meaning the second force results in a counterbalancing or countervailing force in the opposite direction of the first force. As shown in the previous figures, this antagonistic force may be a pulling force that causes a torque to be applied in the opposite direction about the articulation pivot of the end effector. In other aspects, if the first force is a pushing force, then the second force may also be a pushing force but applied in an opposite direction relative to the end effector.

The end effector that is coupled to the first and second articulation arms articulates 13906 about a pivot, where the degree of articulation is based on a ratio of the first and second forces. If the pivot about which the end effector articulates is positioned in between the hinges that link the end effector to the two articulation arms, then the antagonistic second force should be the same type of force as the first force, e.g., both are pulling forces, or both are pushing forces. On the other hand, if both of the hinges connecting the two articulation arms to the end effector are located on the same side of the articulation pivot, then the antagonistic second force should be of the opposite type of force as the first force, e.g., one is a pulling force and the other is a pushing force. As shown in the previous examples, the articulation pivot may be located off-center from the centerline, allowing for a unique ratio of forces at all articulation angles.

The functions or processes 13900 described herein may be executed by any of the processing circuits described herein, such as the control circuit 961 (FIG. 22), 800 (FIG. 23), 810 (FIG. 24), 820 (FIG. 25), 4420 (FIG. 26), and/or control circuit 2510 (FIG. 30). Aspects of the motorized surgical instrument may be practiced without the specific details disclosed herein. Some aspects have been shown as block diagrams rather than detail.

Various aspects of the subject matter described herein are set out in the following examples:

1. A system for a robotic surgical instrument, the system comprising: a control circuit; a first motor and a second motor, both communicatively coupled to the control circuit; a first articulation arm communicatively coupled to the first motor; a second articulation arm communicatively coupled to the second motor; and an end effector coupled to the first articulation arm via a first hinge and the second articulation arm via a second hinge; wherein: the control circuit is configured to cause the first motor to apply a first force to the first articulation arm; the control circuit is configured to cause the second motor to apply a second force to the second articulation arm, wherein the second force is antagonistic to the first force such that the first and second forces apply counteracting forces at the end effector; and the first and second forces cause the end effector to articulate via the first and second hinges.

2. The system of Example 1, wherein the end effector is configured to articulate to a prescribed angle based on a ratio of magnitudes between the first force and the second force.

3. The system of one or more of Example 1 through Example 2, further comprising an articulation pivot coupled to the end effector, wherein the end effector is further configured to articulate about the articulation pivot.

4. The system of Example 3, wherein the articulation pivot is positioned off of a center axis running longitudinally in between and equidistant from at least a portion of the first and second articulation arms.

5. The system of one or more of Example 3 through Example 4, further comprising a shaft encapsulating the first and second articulation arms.

6. The system of Example 5, further comprising a pivot link coupled to the articulation pivot and stably positioned within the shaft, wherein the pivot link is configured to stabilize the end effector while the end effector articulates about the articulation pivot.

7. The system of Example 6, wherein the pivot link and the articulation pivot are positioned off of a center axis running longitudinally in between and equidistant from at least a portion of the first and second articulation arms.

8. The system of Example 7, wherein the first force is greater than the second force when the end effector is articulated to a zero degree angle from a center position.

9. The system of one or more of Example 1 through Example 8, wherein the control circuit is configured to operate the first motor independent of the second motor.

10. The system of one or more of Example 1 through Example 9, wherein the first and second forces are pulling forces applied to the first and second articulation arms, respectively.

11. The system of one or more of Example 1 through Example 10, wherein the first and second forces are pushing forces applied to the first and second articulation arms, respectively.

12. A method of a robotic surgical instrument comprising a control circuit, a first motor, a second motor, a first articulation arm, a second articulation arm, and an end effector, the method comprising: instructing, by the control circuit, the first motor to apply a first force to the first articulation arm; instructing, by the control circuit, the second motor to apply a second force to the second articulation arm, wherein the second force is antagonistic to the first force such that the first and second forces apply counteracting forces at the end effector; and causing the end effector to articulate via first and second hinges based on the first and second forces applied to the first and second articulation arms, respectively.

13. The method of Example 12, further comprising causing the end effector to articulate to a prescribed angle based on a ratio of magnitudes between the first force and the second force.

14. The method of one or more of Example 12 through Example 13, wherein the robotic surgical instrument further comprises an articulation pivot coupled to the end effector, wherein the end effector further articulates about the articulation pivot.

15. The method of Example 14, wherein the articulation pivot is positioned off of a center axis running longitudinally in between and equidistant from at least a portion of the first and second articulation arms.

16. The method of one or more of Example 14 through Example 15, wherein the robotic surgical instrument further comprises a shaft encapsulating the first and second articulation arms.

17. The method of one or more of Example 15 through Example 16, wherein the first force is greater than the second force when the end effector is articulated to a zero degree angle from a center position.

18. The method of one or more of Example 12 through Example 17, wherein applying the first force to the first motor is independent of applying the second force to the second motor.

19. The method of one or more of Example 1 through Example 18, wherein the first and second forces are pulling forces applied to the first and second articulation arms, respectively.

20. The method of one or more of Example 12 through Example 19, wherein the first and second forces are pushing forces applied to the first and second articulation arms, respectively.

Parts of this disclosure may be presented in terms of instructions that operate on data stored in a computer memory. An algorithm refers to a self-consistent sequence of steps leading to a desired result, where a "step" refers to a manipulation of physical quantities which may take the form of electrical or magnetic signals capable of being stored, transferred, combined, compared, and otherwise manipulated. These signals may be referred to as bits, values, elements, symbols, characters, terms, numbers. These and similar terms may be associated with the appropriate physical quantities and are merely convenient labels applied to these quantities.

Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program which at least partially carries out processes and/or devices described herein, electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components. logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Various aspects of the subject matter described herein are set out in the following examples:

Example 1. A method of controlling velocity of a firing member in a robotic surgical system, the method comprising: detecting, by a control circuit, a condition at an end effector during a closure phase; setting, by the control circuit, command velocity of a motor coupled to a displacement member coupled to the end effector based on the detected condition at the end effector during the closure phase; firing, by the control circuit, the displacement member at the set command velocity; detecting, by the control circuit, a condition at the end effector during a firing phase; and setting, by the control circuit, command velocity of the motor based on the condition detected at the end effector during the firing phase.

Example 2. The method of Example 1, wherein the condition during the closure phase or the firing phase is tissue thickness and the method further comprises: detecting, by the control circuit, a gap defined between an anvil and a staple cartridge portion of the end effector; and adjusting, by the control circuit, the command velocity based on the gap and the command velocity at the time the gap is detected.

Example 3. The method of one or more of Example 1 through Example 2, wherein the condition during the closure phase is closure force applied to an anvil toward a staple cartridge and the method further comprises: detecting, by the control circuit, a closure force defined as the force experienced by the anvil and the staple cartridge portion of the end effector closed on tissue located therebetween; and adjusting, by the control circuit, the command velocity based on the closure force and the command velocity at the time the force is detected.

Example 4. The method of one or more of Example 1 through Example 3, wherein the condition during the firing phase is firing force to displace the displacement member and method further comprises: detecting, by the control circuit, a firing force to displace the displacement member; and adjusting, by the control circuit, the command velocity based on the firing force and the command velocity at the time the force is detected.

Example 5. The method of one or more of Example 1 through Example 4, wherein the condition during the closure phase or the firing phase is electrical impedance of tissue located between an anvil and a cartridge in the end effector and the method further comprises: detecting, by the control circuit, the electrical impedance of the tissue located between the anvil and the staple cartridge of the end effector; and adjusting, by the control circuit, the command velocity based on the electrical impedance and the command velocity at the time the impedance is detected.

Example 6. The method of one or more of Example 1 through Example 5, wherein the condition during the closure phase or the firing phase is coverage of tissue in the end effector and the method further comprises: detecting, by the control circuit, the coverage of tissue located between an anvil and a staple cartridge portion of the end effector and adjust the command velocity based on the coverage and the command velocity at the time the coverage is detected.

Example 7. The method of one or more of Example 1 through Example 6, further comprising adjusting, by the control circuit, the command velocity during the firing phase to adjust the velocity of the displacement member while firing.

Example 8. A method of controlling velocity of a firing member in a robotic surgical system, the method comprising: receiving, by a control circuit, actual closure force of a closure member from a force sensor coupled to the closure member and the control circuit; comparing, by the control circuit, the actual closure force to a threshold closure force; determining, by the control circuit, a set point velocity to displace the closure member based on the comparison; and controlling, by the control circuit, the actual velocity of the closure member based on the set point velocity.

Example 9. The method of Example 8, wherein the control circuit comprises a proportional, integral, and derivative (PID) feedback control system and wherein the PID feedback control system comprises a primary PID feedback loop and a secondary PID feedback loop, the method further comprising: determining, by the primary feedback loop, a first error between the actual closure force of the closure member and a threshold closure force and set the set point velocity based on the first error; and determining, by the secondary feedback loop, a second error between the actual velocity of the closure member and the set point velocity and control the actual velocity of the closure member based on the second error.

Example 10. The method of one or more of Example 8 through Example 9, wherein the threshold closure force comprises an upper threshold and a lower threshold, the method further comprising: advancing, by the control circuit, the closure member distally when the actual closure force is less than the lower threshold; and retracting, by the control circuit, the closure member proximally when the actual closure force is greater than the lower threshold.

Example 11. The method of Example 10, further comprising holding, by the control circuit, the closure member in place when the actual closure force is between the upper and lower thresholds.

Example 12. The method of one or more of Example 8 through Example 11, wherein receiving, by the control circuit, closure force from a force sensor coupled to the control circuit comprises receiving, by the control circuit, closure force from a torque sensor coupled to an output shaft of a motor coupled to the closure member, wherein the torque sensor is configured to measure the closure force.

Example 13. The method of one or more of Example 8 through Example 12 wherein receiving, by the control circuit, closure force from a force sensor coupled to the control circuit comprises receiving, by the control circuit, closure force from a strain gauge coupled to the closure member, wherein the strain gauge is configured to measure the closure force.

Example 14. The method of Example 8, wherein receiving, by the control circuit, closure force from a force sensor coupled to the control circuit comprises receiving, by the control circuit, closure force from a load cell coupled to the closure member, wherein the load cell is configured to measure the closure force.

Example 15. The method of one or more of Example 8 through Example 14, further comprising a position sensor coupled to the closure member and to the control circuit, the method further comprising receiving, by the control circuit, a position of the closure member from the position sensor.

Example 16. The method control of one or more of Example 8 through Example 15, further comprising advancing, by the control circuit, the closure member during at least a portion of a firing stroke.

Example 17. A method of controlling velocity of a firing member in a robotic surgical system, the method comprising: receiving, by a control circuit, actual closure force of a closure member from a force sensor coupled to the closure member and the control circuit; receiving, by the control circuit, actual position of a firing member from a position sensor coupled to the firing member and the control circuit; and setting, by the control circuit, a new closure force based on the actual closure force applied to the closure member and the actual position of the firing member.

Example 18. The method of Example 17, wherein receiving, by a control circuit, the actual closure force of the closure member from the force sensor comprises receiving, by the control circuit, the actual closure force of the closure member from a torque sensor coupled to an output shaft of a motor coupled to the closure member, wherein the torque sensor is configured to measure closure force.

Example 19. The method of one or more of Example 17 through Example 18, wherein receiving, by a control circuit, the actual closure force of the closure member from the force sensor comprises receiving, by the control circuit, the actual closure force of the closure member from a strain gauge coupled to the closure member, wherein the strain gauge is configured to measure closure force.

Example 20. The method of one or more of Example 17 through Example 18, wherein receiving, by a control circuit, the actual closure force of the closure member from the force sensor comprises receiving, by the control circuit, the actual closure force of the closure member from a load cell coupled to the closure member, wherein the load cell is configured to measure closure force.

Example 21. The method of one or more of Example 17 through Example 18, further comprising advancing, by the control circuit, the closure member during at least a portion of the firing stroke.

The invention claimed is:

1. A surgical system, comprising:
    an end effector, comprising:
        a first jaw; and
        a second jaw rotatable relative to the first jaw between an open position and a closed position;
    a closure driver configured to apply a closure force to the second jaw to rotate the second jaw toward the closed position;
    a force sensor to measure a parameter indicative of the closure force; and
    a control circuit, to:
        receive an output of the force sensor indicative of the parameter; and
        set a velocity of the closure driver based on the received output and a force threshold.

2. The surgical system of claim 1, wherein the closure driver is movable between a proximal position and a distal position, and wherein the control circuit is further to select between driving the closure driver toward the proximal position and driving the closure driver toward the distal position based on the received output and the force threshold.

3. The surgical system of claim 1, further comprising a firing driver movable through the end effector during a firing stroke, and wherein the control circuit is to displace the closure driver at the velocity during a portion of the firing stroke.

4. The surgical system of claim 1, further comprising a motor to drive the closure driver.

5. The surgical system of claim 4, wherein the force sensor comprises a torque sensor coupled to the motor.

6. The surgical system of claim 1, wherein the force sensor comprises a strain gauge coupled to the closure driver.

7. The surgical system of claim 1, wherein the force sensor comprises a load cell coupled to the closure driver.

8. A surgical system, comprising:
    an end effector, comprising:
        a first jaw; and
        a second jaw rotatable relative to the first jaw between an open position and a closed position;
    a closure tube configured to apply a closure force to the second jaw to rotate the second jaw toward the closed position;
    a force sensor to measure a closure force; and
    a control circuit, to:
        receive an output from the force sensor indicative of the closure force; and
        selectively displace the closure tube based on the received output and a force threshold.

9. The surgical system of claim 8, wherein the closure tube is movable between a proximal position and a distal position, and wherein control circuit is to selectively displace the closure tube by selecting between displacing the closure tube toward the proximal position and displacing the closure tube toward the distal position based on the received output and the force threshold.

10. The surgical system of claim 8, further comprising a knife movable through the end effector during a firing stroke, and wherein the control circuit is to select the displacement the closure tube during a portion of the firing stroke.

11. The surgical system of claim 8, further comprising a motor to drive the closure tube.

12. The surgical system of claim 11, wherein the force sensor comprises a torque sensor coupled to the motor.

13. The surgical system of claim 8, wherein the force sensor comprises a strain gauge coupled to the closure tube.

14. The surgical system of claim 8, wherein the force sensor comprises a load cell coupled to the closure tube.

15. A surgical system, comprising:
    an end effector, comprising:
        a first jaw; and
        a second jaw movable relative to the first jaw between an open position and a closed position;
    a closure driver movable between a proximal position and a distal position, wherein the closure driver is configured to apply a closure force to the second jaw to rotate the second jaw toward the closed position based on the closure driver moving toward the distal position, and wherein the second jaw is rotatable toward the open position based on the closure driver moving toward the proximal position;
    a force sensor to measure a parameter indicative of the closure force; and
    a control circuit, to:
        receive an output of the force sensor indicative of the parameter; and
        select between displacing the closure driver toward the proximal position, displacing the closure driver toward the distal position, and maintaining a position of the closure driver based on the received output and a force threshold.

16. The surgical system of claim 15, further comprising a firing driver movable through the end effector during a firing stroke, and wherein the control circuit is to select the displacement of the closure driver during a portion of the firing stroke.

17. The surgical system of claim 15, further comprising a motor to drive the closure driver.

18. The surgical system of claim 17, wherein the force sensor comprises a torque sensor coupled to the motor.

19. The surgical system of claim 15, wherein the force sensor comprises a strain gauge coupled to the closure driver.

20. The surgical system of claim 15, wherein the force sensor comprises a load cell coupled to the closure driver.

* * * * *